United States Patent [19]

Barnwell et al.

[11] Patent Number: 5,646,247

[45] Date of Patent: Jul. 8, 1997

[54] MEROZOITE ANTIGENS LOCALIZED AT THE APICAL END OF THE PARASITE

[75] Inventors: John W. Barnwell; Mary R. Galinski, both of New York, N.Y.

[73] Assignee: New York University, New York, N.Y.

[21] Appl. No.: 792,865

[22] Filed: Oct. 4, 1991

Related U.S. Application Data

[63] Continuation of PCT/US90/01849, Apr. 3, 1990, which is a continuation-in-part of Ser. No. 334,270, Apr. 6, 1989, abandoned, and Ser. No. 608,639, Nov. 2, 1990, abandoned, which is a continuation of Ser. No. 334,041, Apr. 5, 1989, abandoned.

[51] Int. Cl.⁶ .......................... C07K 14/44; C12N 15/30; A61K 39/005; A61K 39/00
[52] U.S. Cl. .................. 530/350; 424/191.1; 424/192.1; 435/69.3; 536/23.5
[58] Field of Search .......................... 530/350; 424/88, 424/92, 191, 191.2; 435/69.3; 536/23.5

[56] References Cited

U.S. PATENT DOCUMENTS

| | | | |
|---|---|---|---|
| 4,735,799 | 4/1988 | Patarroyo | 424/88 |
| 4,767,622 | 8/1988 | Ristic et al. | 424/88 |

OTHER PUBLICATIONS

Miller et al., Monoclonal Antibodies to a 140,000-m.w. Protein on *Plasmodium knowlesi* Merozoites Inhibit Their Invasion of Rhesus Erythrocytes, J. Immunol. 132: 438–442, 1984.

Haynes et al., Receptor–like Specificity of a *Plasmodium knowlesi* Malarial Protein that Binds to Duffy Antigen Ligands on Erythrocytes, J. Exp. Medicine 167: 1873–1881, 1988.

Epstein et al., Monoclonal Antibodies Against a Specific Surface Determinant on Malarial (*Plasmodium knowlesi*) Merozoites Block Erythrocyte Invasion, J. Immunol. 127: 212–217, 1981.

Burns et al., The 3' Portion of the Gene for a *Plasmodium yoelii* Merozoite Surface Antigen Encodes the Epitope Recognized by a Protective Monoclonal Antibody, Proc. Natl. Sci. USA 85: 602–602, 1988.

Miller et al., Indentification of *Plasmodium knowlesi* Erythrocyte Binding Proteins, Molec. Biochem. Parasitol. 31:217–222, 1988.

Hadley et al., Invasion of Erythrocytes by Malaria Parasites: Erythrocyte Ligands and Parasite Receptors, Prog. Allergy 41: 49–71, 1988.

David et al., *Plasmodium vivax* Malaria: Parasite Biology Defines Potential Targets for Vaccine Developement, Biol. of the Cell, 64: 251–260, 1988.

Aikawa et al., Structural Alteration of the Erythrocyte Membrane During Malarial Parasite Invasion and Intraery–throcytic Development, *Ciba Foundation Symposium* 94: 45–63, 1983.

Wanidworanun et al., Cross–Reacting Antigens to Pc96: A Protective Antigen of *P. chabaudi* in *P. Falciparum*, *P. Vivax* and *P. Cynomolgi*, Am J. Trop. Med. Hyg. 40: 579–584, 1989.

(List continued on next page.)

*Primary Examiner*—Robert A. Wax
*Assistant Examiner*—William W. Moore
*Attorney, Agent, or Firm*—Darby & Darby, P.C.

[57] ABSTRACT

Disclosed are compounds comprising an amino acid sequence selected from the group consisting of malarial merozoite proteins located at the apical end of merozoites and peptides the peptides comprising synthetic versions, derivatives, analogs and fragments of the merozoite proteins. Certain of these compounds have the property of binding to a Duffy blood group antigen from primate red blood cells. Disclosed are also nucleic acids comprising a nucleotide sequence encoding such peptides or proteins and nucleic acids hybridizing therewith. The compounds and antibodies recognizing these compounds are useful in inhibiting invasion of susceptible primate red blood cells by malarial merozoites.

4 Claims, 42 Drawing Sheets

OTHER PUBLICATIONS

Nichols et al., A New Human Duffy Blood Group Specificity Defined by a Muring Monoclonal Antibody, J. Exp. Med. 166: 776–785, 1987.

Haynes et al., A 135 Kilodalton Receptor Molecule from Malaria Parasites Binds to a Human Erythrocyte Ligand Associated with Duffy Antigens and Correlates with Invasion, ABSTRACT,Clin. Res. 35: 615A, 1987.

Barnwell et al., In vitro Evaluation of the Role of the Duffy Group in Erythrocyte Invasion by *P. Vivax*, J. Exp. Med. 169: 1795–1802, 1989.

Galinski et al. (1989) J. Cell Biochem Suppl. 13E, 104.

Galinski et al. (1992) Cell 69, 1213–1226.

Collins, W.E., et al., 1986, Nature, 323: 259–262.

Bockenstedt, L.K., et al., 1993, Journal of Immunology, 151: 900–902.

Barnwell, J.W., et al., 1989, Progress in Clinical and Biological Research, 313 : 1–11.

Marakami, K., et al., 1985, Journal of Cell Science, 73: 311–320.

Sim, B.K.L., et al., 1990, The Journal of Cell Biology, 111:1877–1884.

Waters, A.P., et al., 1990, The Journal of Biological Chemistry, 265(29): 17974–17979.

FIG. 1A

```
  1                       5                             10                            15
TTC GAT AAA GAA AAA GTT AAA GAT ACA AGT TTT GAT GAA AAA AAG AAA                          48
AAG CTA TTT CTT TTT CAA TTT CTA TGT TCA AAA CTT TTT TTC TTT
Phe Asp Lys Glu Lys Val Lys Asp Thr Ser Phe Asp Glu Lys Lys Lys 20                            25                            30
AGC ATA GAA AAA GCT TAT GAA AAA ATG GGA AAT ACG CTT AAA GAA TTA                          96
TCG TAT CTT TTT CGA ATA CTT TTT TAC CCT TTA TGC GAA TTT CTT AAT
Ser Ile Glu Lys Ala Tyr Glu Lys Met Gly Asn Thr Leu Lys Glu Leu 35                            40                            45
GAA AAA ATG GAT GAC CTG GAA AAA ATA AAC TTT CTT GAA GTA GAA GCT                         144
CTT TTT TAC CTA CTG GAC CTT TTT TAT TTG AAA GAA CTT CAT CTT CGA
Glu Lys Met Asp Asp Leu Glu Lys Ile Asn Phe Leu Glu Val Glu Ala 50                            55                            60
CAA ATA CAA TAC AAA AGA ATT TTT GAT CAT GAT GTT AAT TTG ATG                             192
GTT TAT GTT ATG TTT TCT TAA AAA CTA GTA CAA TTA AAC TAC
Gln Ile Gln Tyr Lys Arg Ile Phe Ile Asp His Asp Val Asn Leu Met 65                            70                            75                    80
AAT GAT GAA GTT GAA AAG TCC AAA ATT GTG ATG GAA AAA ATC GAA TTA                         240
TTA CTA CTT CAA CTT TTC AGG TTT TAA CAC TAC CTT TTT TAG CTT AAT
```

FIG. 1B

```
Asn Asp Glu Val Glu Lys Ser Lys Ile Val Met Glu Lys Ile Glu Leu
                         85                  90                  95
TAT AAA GAA ATT GAC GAA ATT AAA CAG AAA ACG AAT GAG TAT AAG        288
ATA TTT CTT TAA CTG CTT TAA TTT GTC TTT TGC TTA CTC ATA TTC

Tyr Lys Glu Ile Asp Glu Ile Lys Gln Lys Thr Asn Glu Tyr Lys
                     100                 105                 110
CAA GGT GAT ACA TCT AAT TTT TAT ACA GAA CAA TAC GTT TCA GCT        336
GTT CCA CTA TGT AGA TTA AAA ATA TGT CTT GTT ATG CAA AGT CGA

Gly Asp Thr Ser Asn Phe Tyr Tyr Thr Glu Gln Tyr Asn Ser Ala
                 115                 120                 125
ACA CAG AGT AAA GCT AAA ATA GAA CAA TTT ATT AAT ATT GCT ACG ACA    384
TGT GTC TCA TTT CGA TTT TAT CTT GTT AAA TAA TTA TAA CGA TGC TGT

Thr Gln Ser Lys Ala Lys Ile Glu Gln Phe Ile Asn Ile Ala Thr Thr
             130                 135                 140
AAA GGA ACG TCT GAC ACA AGC CAA GAT ATA AAC GAA TTA GAA AGC        432
TTT CCT TGC AGA CTG TGT TCG GTT CTA TAT TTG CTT AAT CTT TCG

Lys Lys Gly Thr Ser Asp Thr Ser Gln Asp Ile Asn Glu Leu Glu Ser
```

FIG. 1C

```
145                     150                     155                     160
ATT AAA GAG GTG CAT AAA AAT TTA CAA CTA GTC AAA CAA GAA AGT      480
TAA TTT CTC CAC GTA TTT TTA AAT GTT GAT CAG TTT GTT CTT TCA
Ile Lys Glu Val His Lys Asn Leu Gln Leu Val Lys Gln Glu Ser 165                     170                     175
AAT TCT ATG GAG GAA ATG CGA AAA CAA ATT CTA AGC ATG AAG GAT TTG   528
TTA AGA TAC CTC CTT TAC GCT TTT GTT TAA GAT TCG TAC TTC CTA AAC
Asn Ser Met Glu Glu Met Arg Lys Gln Ile Leu Ser Met Lys Asp Leu 180                     185                     190
CTA ATT TTG AAC AAT TCC GAA ACT ATA GCT AAA GAA ATA TCA AAT AAT   576
GAT TAA AAC TTG TTA AGG CTT TGA TAT CGA TTT CTT TAT AGT TTA TTA
Leu Ile Leu Asn Asn Ser Glu Thr Ile Ala Lys Glu Ile Ser Asn Asn 195                     200                     205
ACT CAA AAC GCA TTA GGT TTT AGG GAG AAT GCA AAA ACA AAA CTT AAT   624
TGA GTT TTG CGT AAT CCA AAA TCC CTC TTA CGT TTT TGT TTT GAA TTA
Thr Gln Asn Ala Leu Gly Phe Arg Glu Asn Ala Lys Thr Lys Leu Asn 210                     215                     220
AAA ACA GAT GAA CTA TTG CAA AGA GTG GCA GCT ATG ATA GAA GAG GCA   672
TTT TGT CTA CTT GAT AAC GTT TCT CAC CGT CGA TAC TAT CTT CTC CGT
Lys Thr Asp Glu Leu Leu Gln Arg Val Ala Ala Met Ile Glu Glu Ala
```

FIG. ID

```
        225
Lys Thr Asp Glu Leu Leu Gln Arg Val Ala Ala Met Ile Glu Glu Ala
                            230                     235                     240
AAG GCA CAT AAG AAC AAT ATT GAC ATA GCT TTA GAA GAT GCA CAA ATA   720
TTC CGT GTA TTC TTG TTA TAA CTG TAT CGA AAT CTT CTA CGT GTT TAT

Lys Ala His Lys Asn Asn Ile Asp Ile Ala Leu Glu Asp Ala Gln Ile
                            245                     250                     255
GAT ACG GAG GTA AGC AAA ATT GAA CAA ATT AAT CGT GAA ATT ATG AAT   768
CTA TGC CTC CAT TCG TTT CTT AAG GTT TAA TTA GCA CTT TAA TAC TTA

Asp Thr Glu Val Ser Lys Ile Glu Gln Ile Asn Arg Glu Ile Met Asn
                            260                     265                     270
AAA AAA GAT GAA ATT AAA TCC TAT TTA AGT GAA ATA TAT AAA GAA TAT AAA   816
TTT TTT CTA CTT TAA TTT AGG ATA AAT TCA CTT TAT ATA TTT CTT ATA TTT

Lys Lys Asp Glu Ile Lys Ser Tyr Leu Ser Glu Ile Lys Glu Tyr Lys
                            275                     280                     285
GAC AAA TGC ACA ACC GAA ATC AGT AAT TCA AAA AGA GGA AAA GAT AAA   864
CTG TTT ACG TGT TGG CTT TAG TCA TTA AGT TTT TCT CCT TTT CTA TTT

Asp Lys Cys Thr Thr Glu Ile Ser Asn Ser Lys Arg Gly Lys Asp Lys
```

FIG. 1E

```
                290              295              300
ATT GAG TTC TTG GAA AAA TTT AAG CCT AAT GAG GAA AGC AAT TCG AAT    912
TAA CTC AAG AAC CTT TTT AAA TTC GGA TTA CTC CTT TCG TTA AGC TTA
Ile Glu Phe Leu Glu Lys Phe Lys Pro Asn Glu Glu Ser Asn Ser Asn 305              310              315              320
AAG GTT AAC ATT AAT GAA ATA AGA AAT GAA TCT GAA CAA             960
TTC CAA TTG TAA TTA CTT TAT TCT TTA CTT AGA CTT GTT
Lys Val Asn Ile Asn Glu Ile Arg Asn Glu Ser Glu Gln 325              330              335
TAC TTA AAA GAT ATA GAA GAC GCA GAA ACA GCT AGT ACA TGT AAA GTA
ATG AAT TTT CTA TAT CTT CTG CGT CTT TGT CGA TCA TGT ACA TTT CAT   1008
Tyr Leu Lys Asp Ile Glu Asp Ala Glu Lys Gln Ala Ser Thr Lys Val 340              345              350
GAA CTA TTC CAT AAA CAT GAA ACA ACT ATC AGT AAT ATT TTC AAG GAA
CTT GAT AAG GTA TTT GTA CTT TGT TGA TAG TCA TTA TAA AAG TTC CTT   1056
Glu Leu Phe His Lys His Glu Thr Thr Ile Ser Asn Ile Phe Lys Glu 355              360              365
TCT GAA ATT TTA GGA GTG GAA ACT AAA TCC CAA AAA ATT AAT AAA
AGA CTT TAA AAT CCT CAC CTT TGA TTT AGG GTT TTT TAA TTA TTT       1104
Ser Glu Ile Leu Gly Val Glu Thr Lys Ser Gln Lys Ile Asn Lys
```

FIG. IF

```
    Ser Glu Ile Leu Gly Val Glu Thr Lys Ser Gln Lys Lys Ile Asn Lys
                          370                     375                     380
    GCA GAA GAC ATA ATG AAA GAA ATT GAG CGT CAC AAT TCT GAA ATT CAA
    CGT CTT CTG TAT TAC TTT CTT TAA CTC GCA GTG TTA AGA CTT TAA GTT    1152
    Ala Glu Asp Ile Met Lys Glu Ile Glu Arg His Asn Ser Glu Ile Gln
              385                     390                     395                     400
    ACA CAG GTG AAA GGT TTC CAA GAA AAT CTA AAT AAA CTG AAC GAG CCC
    TGT GTC CAC TTT CCA AAG GTT CTT TTA GAT TTT GAC TTG CTC GGG       1200
    Thr Gln Val Lys Gly Phe Gln Glu Asn Leu Asn Lys Leu Asn Glu Pro
                          405                     410                     415
    CAT AAT TAT GAC AAC GCA GAA GAT GAA CTT GAA AAT AAT GAT AAA TCT ACG
    GTA TTA ATA CTG TTG CGT CTT CTA CTT GAA CTT TTA TTA CTA TTT AGA TGC  1248
    His Asn Tyr Asp Asn Ala Glu Asp Glu Leu Glu Asn Asn Asp Lys Ser Thr
              420                     425                     430
    AAT GCA AAG GTA CTT ATA GAA ACT AAC CTA GAA AGT GTA AAA CAT AAT
    TTA CGT TTC CAT GAA TAT CTT TGA TTG GAT CTT TCA CAT TTT GTA TTA    1296
    Asn Ala Lys Val Leu Ile Glu Thr Asn Leu Glu Ser Val Lys His Asn
```

FIG. 1G

```
                          435                    440                              445
TTA TCA GAA ATT ACT AAT ATT ACT AAA TTT CAG GGA GAA CTT AAA ATA TAC AGT
AAT AGT CTT TAA TGA TTA TAA TTT GTC CCT CTT TTT TAT ATG TCA          1344
Leu Ser Glu Ile Thr Asn Ile Lys Gln Gly Gly Glu Lys Ile Tyr Ser 450                              455                    460
AAA GCT AAA GAT ATC ATG CAA AAA ATA TTT ACT TCA GAA AAT ACT
TTT CGA TTT CTA TAG TAC GTT TTT TAT TTT TGA AGT CTT TTA TGA          1392
Lys Ala Lys Asp Ile Met Gln Lys Ile Lys Ala Thr Ser Glu Asn Thr 465                              470                    475                    480
GCA GAG AAA ACT TTA GAG AAG GTG AAA GAC CAA GAC CTG TCT AAT TAT GTT
CGT CTC TTT TGA AAT CTC TTC CAC TTT CTG GTT CTG GAC AGA TTA ATA CAA  1440
Ala Glu Lys Thr Leu Glu Lys Val Lys Asp Gln Asp Leu Ser Asn Tyr Val 485                    490                    495
AAT TAT TTA AAT CAA ATA ACC ACA GAA AGA AAT CTT ATC GTT ACG GAA
TTA ATA AAT TTA GTT TAT TGG TGT CTT TCT TTA GAA TAG CAA TGC CTT      1488
Asn Tyr Leu Asn Gln Ile Thr Thr Glu Arg Asn Leu Ile Val Thr Glu
```

FIG. 1H

```
     500                    505                    510
AAA AAT AGA CTA AAT GGT ATA GAT TCC ACT ATT ACA AAT ATA GAA GGG    1536
TTT TTA TCT GAT TTA CCA TAT CTA AGG TGA TAA TGT TTA TAT CTT CCC
Lys Asn Arg Leu Asn Gly Ile Asp Ser Thr Ile Thr Asn Ile Glu Gly 515                    520                    525
GCA CTT AAA GAA TCC AAG GGA AAT TAT GAA ATT GGA TTT TTG GAA AAG    1575
CGT GAA TTT CTT AGG TTC CCT TTA ATA CTT TAA CCT AAA AAC CTT TTC
Ala Leu Lys Glu Ser Lys Gly Asn Tyr Glu Ile Gly Phe Leu Glu Lys 530                    535                    540
TTA GAA GAA ATA GGT AAA AAT AGA AAA TTA AAG GTT GAC ATA ACC AAA    1623
AAT CTT CTT TAT CCA TTT TTA TCT AAT TTC CAA CTG TAT TGG TTT
Leu Glu Glu Ile Gly Lys Asn Arg Lys Leu Lys Val Asp Ile Thr Lys 545                         550                    555              600
AAA TCA ATA AAT TCA ACA GTG GGA AAC TTT TCT TCC CTC TTC AAC AAT    1671
TTT AGT TAT TTA AGT TGT CAC CCT TTG AAA AGA GAG GAG AAG TTG TTA
Lys Ser Ile Asn Ser Thr Val Gly Asn Phe Ser Ser Leu Phe Asn Asn 605                    610              615
TTT GAT TTA AAT CAA TAT GAC TTT AAT AAA AAT ATA AAT GAT TAT GAA    1719
AAA CTA AAT TTA GTT ATA CTG AAA TTA TTT TTA TAT TTA CTA ATA CTT
```

FIG. 1I

```
Phe Asp Leu Asn Gln Tyr Asp Phe Asn Lys Asn Ile Asn Asp Tyr Glu
                          620                 625                 630
AAT AAA ATG GGA GAA ATA TAT CCT CTT GAA AAC GAA TTT AAA GGA TCA CCT AGT AAT TTA AAA    1767
TTA TTT TAC CCT CTT TAT ATA GGA GAA CTT TTG CTT AAA TTT CCT AGT AAT TTA TTT

Asn Lys Met Gly Glu Ile Tyr Asn Glu Phe Glu Gly Ser Leu Asn Lys
                          635                 640                 645
ATT AGT GAA AAT TTA AGA AAT GCT TCG GAA AAC ACT TCA GAC TAT AAC    1815
TAA TCA CTT TTA AAT TCT TTA CGA AGC CTT TTG AGT CTG ATA TTG

Ile Ser Glu Asn Leu Arg Asn Ala Ser Glu Asn Thr Ser Asp Tyr Asn
                          650                 655                 660
TCA GCA AAA ACA CTG AGG CTA GAG GCA CAG AAA GAA GTT AAT CTA    1863
AGT CGT TTT TGT GAC TCC GAT CTC CGT GTC TTT CTT CAA TTA GAT

Ser Ala Lys Thr Leu Arg Leu Glu Ala Gln Lys Glu Lys Val Asn Leu
                          665                 670                 675                 680
TTA AAT AAA GAA GAA GCA AAT AAA TAT TTA AGA GAT GTT AAA AAA    1911
AAT TTA CTT CTT CGT TTA TTT ATA AAT TCT CTA CAA TTT TTT

Leu Asn Lys Glu Glu Ala Asn Lys Tyr Leu Arg Asp Val Lys Lys
```

FIG. IJ

```
                         685                     690                    695
GTG GAA TCA TTC AGA TTT ATA TTT AAT ATG AAA GAA AGC TTA GAT AAG        1959
CAC CTT AGT AAG TCT AAA TAT TTA TAC TTT CTT TCG AAT CTA TTC

Val Glu Ser Phe Arg Phe Ile Phe Asn Met Lys Glu Ser Leu Asp Lys
                     700                     705                    710
ATT AAT GAG ATG ATT AAA GAA CAA CTA ACA GTC AAT GAA GGA CAC            2007
TAA TTA CTC TAC TAA TTT CTT GTT GAT TGT CAG TTA CTT CCT GTG

Ile Asn Glu Met Ile Lys Lys Glu Gln Leu Thr Val Asn Glu Gly His
                 715                     720                    725
GGT AAC GTT AAA CAA CTA GTT GAA AAT ATT AAA GAG TTA GTT GAT GAA        2055
CCA TTG CAA TTT GTT GAT CAA CTT TTA TAA TTT CTC AAT CAA CTA CTT

Gly Asn Val Lys Gln Leu Val Glu Asn Ile Lys Glu Leu Val Asp Glu
             730                    735                    740
AAC AAC TTA TCA GAT ATA TAT TTA AAA CAA GCG ACG AAA AAT GAG GAA        2103
TTG TTG AAT AGT CTA TAT ATA AAT TTT GTT CGC TGC TTT TTA CTC CTT

Asn Asn Leu Ser Asp Ile Tyr Leu Lys Gln Ala Thr Gly Lys Asn Glu Glu
```

FIG. IK

```
745                         750                                   760
ATA CAG AAA ATA ACG CAC TCT ACG CTT AAA AAT AAA GCA AAA ACT ATT
TAT GTC TTT TAT TGC GTG AGA TGC GAA TTT TTA TTT CGT TTT TGA TAA  2151
Ile Gln Lys Ile Thr His Ser Thr Leu Lys Asn Lys Ala Lys Thr Ile 765                         770                   775
TTA GGA CAC GTA GAT ACT TCT GCA AAA TAT GTA GGC ATT AAA ATA ACA
AAT CCT GTG CAT CTA TGA AGA CGT TTT ATA CAT CCG TAA TTT TAT TGT  2199
Leu Gly His Val Asp Thr Ser Ala Lys Tyr Val Gly Ile Lys Ile Thr 780                         785                   790
CCT GAG TTG GCA CTA ACA GAA TTG AAC GGA GAT GCA AAA TTG AAA ACT
GGA CTC AAC CGT GAT TGT CTT AAC TTG CCT CTA CGT TTT AAC TTT TGA  2247
Pro Glu Leu Ala Leu Thr Glu Leu Asn Gly Asp Ala Lys Leu Lys Thr 795                         800                   805
GCA CAG GAA TTA AAA TTT GAG TCA AAA AAT AAT GTA GTA CTA GAA ACA
CGT GTC CTT AAT TTT AAA CTC AGT TTT TTA TTA CAT CAT GAT CTT TGT  2295
Ala Gln Glu Leu Lys Phe Glu Ser Lys Asn Asn Val Val Leu Glu Thr 810                         815                   820
GAA AAT ATG TCA AAG AAT ACA AAC GAA TTG GAT GTT CAT AAA AAT ATA
CTT TTA TAC AGT TTC TTA TGT TTG CTT AAC CTA CAA GTA TTT TTA TAT  2343
Glu Asn Met Ser Lys Asn Thr Asn Glu Leu Asp Val His Lys Asn Ile
```

FIG. 1L

```
     Glu Asn Met Ser Lys Asn Thr Asn Glu Leu Asp Val His Lys Asn Ile
     825                 830                 835                 840
     CAG GAT GCT TAC AAG AAT GTT GCA CTG GAA ATA CTT GCC CAC TCA GAC GAA
     GTC CTA CGA ATG TTC CAA CGT GAC CTT TAT GAA CGG AGT CTG CTT       2391

Gln Asp Ala Tyr Lys Val Ala Leu Glu Ile Leu Ala His Ser Asp Glu
                     845                 850                 855
     ATA GAT ACA AAA CAA AAA GAC AGT TCT AAA TTA ATA GAA ATG GGA AAC
     TAT CTA TGT TTT GTT TTT CTG TCA AGA TAT AAT CTT TAC CCT TTG       2439

Ile Asp Thr Lys Gln Lys Asp Ser Ser Lys Leu Ile Glu Met Gly Asn
                         860                 865                 870
     CAA ATA TAT ATA CTT AAA GTT GTG CTA AAT CAA TAC AAA AAT ATA
     GTT TAT ATA GAA TTT CAA CAC GAT TAT ATT GTT ATG TTT TTA TAT       2487

Gln Ile Tyr Leu Lys Val Val Leu Ile Asn Gln Tyr Lys Asn Lys Ile
                             875                 880                 885
     AGC TCT ATA AAA AGT AAG GAA GCT GTT TCA GTC AAA ATA GGT AAT
     TCG AGA TAT TTT TCA TTC CTT CGA CAA AGT CAG TAT CCA TTA       2535

Ser Ser Ile Lys Ser Lys Glu Ala Val Ser Val Lys Ile Gly Asn
```

FIG. IM

```
            890                       895                        900
GTT TCC AAG AAA CAT AGT GAG TTA AGC AAA ATT ACA TGC AGC GAT AAA
CAA AGG TTC TTT GTA TCA CTC AAT TCG TTT TAA TGT ACG TCG CTA TTT    2583
Val Ser Lys Lys His Ser Glu Leu Ser Lys Ile Thr Cys Ser Asp Lys 905                       910                       915                  920
AGT TAC GAT AAC ATC ATA GCG TTA GAG AAA CAA ACT GAA TTA CAA AAT
TCA ATG CTA TTG TAG TAT CGC AAT CTC TTT GTT TGA CTT AAT GTT TTA    2631
Ser Tyr Asp Asn Ile Ile Ala Leu Glu Lys Gln Thr Glu Leu Gln Asn 925                       930                       935
CTA CGC AAT TCT TTC ACT CAA GAA AAG ACT AAC ACG AAT AGC GAT TCG
GAT GCG TTA AGA AAG TGA GTT CTT TTC TGA TTG TGC TTA TCG CTA AGC    2679
Leu Arg Asn Ser Phe Thr Gln Glu Lys Thr Asn Thr Asn Ser Asp Ser 940                       945                       950
AAG TTG GAA AAA ATT AAA ACA GAT TTC GAA AGT TTG AAA TTT GCA TTA
TTC AAC CTT TTT TAA TTT TGT CTA AAG CTT TCA AAC TTT AAA CGT AAT    2727
Lys Leu Glu Lys Ile Lys Thr Asp Phe Glu Ser Leu Lys Asn Ala Leu 955                       960                       965
AAA ACA CTA GAA GGA GAA GTA AAT GCT CTA AAG GCA AGC TCG GAC AAT
TTT TGT GAT CTT CCT CTT CAT TTA CGA GAT TTC CGT TCG AGC CTG TTA    2775
Lys Leu Glu Lys Thr Asp Phe Glu Ser Leu Lys Asn Ala Leu
```

FIG. 1N

```
Lys Thr Leu Glu Gly Glu Val Asn Ala Leu Lys Ala Ser Ser Asp Asn
             970                 975                 980
CAT GAA CAT GTA CAA AGT GAA CCA GTA AAT CCT GCG CTA TCC
GTA CTT GTA CAT GTT TCA CTT GGT CAT TTA GGA CGC GAT AGG  2823

His Glu His Val Gln Ser Lys Ser Glu Pro Val Asn Pro Ala Leu Ser
 985                 990                 995                1000
GAA ATT GAA AAA GAA ACG GAC ATA GAT AGT CTT AAT ACG GCC CTT
CTT TAA CTT TTT CTT TGC CTG TAT CTA TCA GAA TTA TGC CGG GAA  2871

Glu Ile Glu Lys Glu Thr Asp Ile Asp Ser Leu Asn Thr Ala Leu
                    1005                1010                1015
GAT GAG TTA TTA AAA GGA AGG ACA TGC GAA GTA TCT AGG TAC AAA
CTA CTC AAT AAT TTT CCT TCC TGT ACG CTT CAT AGA TCC ATG TTT  2919

Asp Glu Leu Leu Lys Lys Gly Arg Thr Cys Glu Val Ser Arg Tyr Lys
                    1020                1025                1030
CTG ATA AAG GAT ACC GTT ACC AAA GAA ATA AGT GAT GAC ACC GAA TTA
GAC TAT TTC CTA TGG CAA TGG TTT CTT TAT TCA CTA CTG CTT AAT  2967

Leu Ile Lys Asp Thr Val Thr Lys Glu Ile Ser Asp Asp Thr Glu Leu
```

FIG. 10

```
          1035                         1040                             1045
ATC AAC ACT ATA GAG AAG AAT GTT AAA GCA TAC TTG GCA TAT ATT AAA    3015
TAG TTG TGA TAT CTC TTC TTA CAA TTT CGT ATG AAC CGT ATA TAA TTT
Ile Asn Thr Ile Glu Lys Asn Val Lys Ala Tyr Leu Ala Tyr Ile Lys 1050                         1055                             1060
AAA AAT TAT GAA GAC ACA GTG CAA GAT GTT CTT ACA TTA AAT GAG CAT    3063
TTT TTA ATA CTT CTG TGT CAC GTT CTA CAA GAA TGT AAT TTA CTC GTA
Lys Asn Tyr Glu Asp Thr Val Gln Asp Val Leu Thr Leu Asn Glu His 1065                         1070                             1075                         1080
TTC AAT ACA AAA CAG GTA AGT AAT CAC GAG CCA ACT AAT TTT GAT AAA    3111
AAG TTA TGT TTT GTC CAT TCA TTA GTG CTC GGT TGA TTA AAA CTA TTT
Phe Asn Thr Lys Gln Val Ser Asn His Glu Pro Thr Asn Phe Asp Lys 1085                         1090                             1095
TCA AAT AAG TCA TCC GAA GAG TTA ACT AAA GCT GTT ACT GAC TCA AAA    3159
AGT TTA TTC AGT AGG CTT CTC AAT TGA TTT CGA CAA CTG AGT TTT
Ser Asn Lys Ser Ser Glu Glu Leu Thr Lys Ala Val Thr Asp Ser Lys 1100                         1105                             1110
ACA ATA ATA AGT AAA CTA AAA GGT GTA ATT ATA GAA GTT AAC GAA AAC    3207
TGT TAT TAT TCA TTT GAT TTT CCA CAT TAA TAT CTT CAA TTG CTT TTG
```

FIG. 1P

```
    Thr Ile Ile Ser Lys Leu Lys Gly Val Ile Ile Glu Val Asn Glu Asn
                        1115                1120                1125
    ACT GAA ATG AAC ACT ATA GAA AGC AGT GCA AAA GAA ATT GAA GCT CTC    3255
    TGA CTT TAC TTG TGA TAT CTT TCG TCA CGT TTT CTT TAA CTT CGA GAG

Thr Glu Met Asn Thr Ile Glu Ser Ser Ala Lys Glu Ile Glu Ala Leu
            1130                1135                1140
    TAT AAC GAA TTA AAA AAT ACA TCA TTA AAC GAA ATT TAT CAA            3303
    ATA TTG CTT AAT TTT TTA TGT AGT AAT TTG CTT TAA ATA GTT

Tyr Asn Glu Leu Lys Asn Lys Lys Thr Ser Leu Asn Glu Ile Tyr Gln
    1145                1150                1155                1160
    ACA TCA AAT GAA GTT AAA TTG CAA GAA ATG TAC AAA TCA AAT GCT GAT AAA    3351
    TGT AGT TTA CTT CAA TTT AAC GTT CTT TAC ATG TTT AGT TTA CGA CTA TTT

Thr Ser Asn Glu Val Lys Leu Gln Glu Met Lys Ser Asn Ala Asp Lys
                        1165                1170                1175
    TAC ATC GAT GTA TCT AAA ATA TTT AAC ACT GTA TTA GAC ACT CAA AAG    3399
    ATG TAG CTA CAT AGA TTT TAT AAA TTG TGA CAT AAT CTG TGA GTT TTC

Tyr Ile Asp Val Ser Lys Ile Phe Asn Thr Val Leu Asp Thr Gln Lys
```

FIG. 1Q

```
                1180                   1185                   1190
TCA AAT ATA GTA ACT AAT CAA CAT AGC ATA AAC AAT GTT AAA GAC AAA    3447
Ser Asn Ile Val Thr Asn Gln His Ser Ile Asn Asn Val Lys Asp Lys
                1195                   1200                   1205
TTA AAA GGA AAG CTA CAG GAA TTA GAT GCT GAC AGT TCA TTT ACA        3495
AAT CTC AGG TTT CCT TTC AAA CTT GTC CGA CTG TCA AGT AAA TGT
Leu Lys Gly Lys Leu Gln Glu Leu Ile Asp Ala Asp Ser Ser Phe Thr
        1210                   1215                   1220
TTA GAG TCC ATT AAA AAG TTT AAC GAA ATA TAT AGT CAT ATT AAG ACT    3543
AAT CTC AGG TAA TTT TTC AAA TTG CTT TAT ATA TCA GTA TAA TTC TGA
Leu Glu Ser Ile Lys Lys Phe Asn Glu Ile Tyr Ser His Ile Lys Thr
                                       1235                   1240
AAT ATA GGT GAA CTA GAA CAG TTA CAA CAA ACT AAT AAA AGT GAA CAT    3591
TTA TAT CCA CTT GAT CTT GTC AAT GTT TGA TTA TTT TCA CTT GTA
Asn Ile Gly Glu Leu Glu Gln Leu Gln Gln Thr Asn Lys Ser Glu His
        1245                                          1255
GAT AAT GTC GCA AAG CAC AAA GAA AAA ATT GTA CAT TTA ATA AAC AGG    3639
CTA TTA CAG CGT TTC GTG TTT CTT TTT TAA CAT GTA AAT TAT TTG TCC
```

FIG. IR

```
Asp Asn Val Ala Lys His Lys Glu Lys Ile Val His Leu Ile Asn Arg
                              1260                    1265                           1270
GTA GAA AGT TTG AAA GGT GAT GTG AAA AAT CAT GAT GAT GAC CAA TAT  3687
CAT CTT TCA AAC TTT CCA CTA CAC TTT TTA GTA CTA CTG GTT ATA

Val Glu Ser Leu Lys Gly Asp Val Lys Asn His Asp Asp Gln Tyr
         1275                      1280                         1285
ATG AAA AAA TTA AAT GCT AGT CTA TTA AAT GAT AAT ATT AAA AAT ACA  3735
TAC TTT TTT AAT TTA CGA TCA GAT AAT TTA CTA TTA TAA TTT TTA TGT

Met Lys Lys Leu Asn Ala Ser Leu Leu Asn Asp Asn Ile Lys Asn Thr
           1290
ACG AAT TCC TGC AGC CCG G                                         3754
TGC TTA AGG ACG TCG GGC C

Thr Asn Ser Cys Ser Pro
```

FIG. 2A

```
1                                               15
CTC AAA ACT AAA ATT GAA AAA TTG ATA CAG GAA ACA AGT GAT TCA    48
GAG TTT TGA TTT TAA CTT TTT AAC TAT GTC CTT TGT TCA CTA AGT
Leu Lys Thr Lys Ile Glu Lys Leu Ile Gln Glu Thr Ser Asp Asp Ser 20                      25                  30
CAA AAT GAA TTA GTC ACA ACG AGT ATT ACA AAA CAT TTA GAG AAT GCA    96
GTT TTA CTT CAG TGT TGC TCA TAA TGT TTT GTA AAT CTC TTA CGT
Gln Asn Glu Leu Val Thr Thr Ser Ile Thr Lys His Leu Glu Asn Ala 35                       40                   45
AAG GGG TAT GAG GAT GTA ATA AAA CGA AAT GAA GAA GAT TCA ATT CAG   144
TTC CCC ATA CTC CTA CAT TAT TTT GCT TTA CTT CTT CTA AGT TAA GTC
Lys Gly Tyr Glu Asp Val Ile Lys Arg Asn Glu Glu Asp Ser Ile Gln 55                   60
TTG AGG GAG AAG GCG AAA AGT CTG GAG ACA TTG GAT GAA ATG AAA AAA   192
AAC TCC CTC TTC CGC TTT TCA GAC CTC TGT AAC CTA CTT TAC TTT TTT
Lys Arg Glu Lys Ala Lys Ser Leu Glu Thr Leu Asp Glu Met Lys Lys 65                      70                     75                80
CTA GTT CAG CAG GTT AAC ATG AAT TTG CAA AGT GCT ATA CAA GGC AAT   240
GAT CAA GTC GTC CAA TTG TAC TTA AAC GTT TCA CGA TAT GTT CCG TTA
Leu Arg Glu Lys Ala Lys Ser Leu Glu Thr Leu Asp Glu Met Lys Lys
```

FIG. 2B

```
Leu Val Gln Gln Val Asn Met Asn Leu Gln Ser Ala Ile Gln Gly Asn
                        85                      90                      95
GCT GGT ATA AGC AAA GAG CTG AAT GAG CTT AAA GGC GTT ATC GAA TTG      288
CGA CCA TAT TCG TTT CTC GAC TTA CTC GAA TTT CCG CAA TAG CTT AAC

Ala Gly Ile Ser Lys Glu Leu Asn Glu Leu Lys Gly Val Ile Glu Leu
                100                     105                     110
TTG ATA TCA ACG AAT TAT AGC AGC ATT TTA GAA TAT GTA AAG AAA AAT      336
AAC TAT AGT TGC TTA ATA TCG TCG TAA AAT CTT ATA CAT TTC TTT TTA

Leu Ile Ser Thr Asn Tyr Ser Ser Ile Leu Glu Tyr Val Lys Lys Asn
                115                     120                     125
TCC AGC GAG TCT GTC CGT TTT AGT CAG CTA GCC AAT GGG GAA TTT ACA      384
AGG TCG CTC AGA CAG GCA AAA TCA GTC GAT CGG TTA CCC CTT AAA TGT

Ser Ser Glu Ser Val Arg Phe Ser Gln Leu Ala Asn Gly Glu Phe Thr
                130                     135                     140
AAG GCT GAA GGT GAA GAG AAA AAC GCA AGT GCC AGA TTA GCG GAG GCA      432
TTC CGA CTT CCA CTT CTC TTT TTG CGT TCA CGG TCT AAT CGC CTC CGT

Lys Ala Glu Gly Glu Lys Asn Ala Ser Ala Arg Leu Ala Glu Ala
```

FIG. 2C

```
145                     150                     155                     160
GAG AAG TTA AAG GAA CAA ATT GTC AAA GAT TTA GAC TAC AGT GAC ATA
CTC TTC AAT TTC CTT GTT TAA CAG ATT CTA AAT CTG ATG TCA TAT        480
Glu Lys Leu Lys Glu Gln Ile Val Lys Asp Leu Asp Tyr Ser Asp Ile 165                     170                     175
GAT GAT AAG GTA AAA ATT GAG GGA ATC CTC CCT TCT CTT TAA AAT TTC
CTA CTA TTC CAT TTT CTA CTC CCT TAG GAG GGA AGA GAA ATT TTA AAG    528
Asp Asp Lys Val Lys Ile Glu Gly Ile Leu Arg Glu Ile Leu Lys 180                     185                     190
ATG AAA GAA AGT GCA CTA ACA TTT AAA GAG TCA GAG TCA GAG TTT AAA
TAC TTT CTT TCA CGT GAT TGT AAA TTT CTC AGT CTC AGT CTC AAA TTT   576
Met Lys Glu Ser Ala Leu Thr Phe Trp Glu Ser Glu Lys Phe Lys 195                     200                     205
CAA ATG TGC TCT TCA CAT ATG GAA AAT GCT TTA CGA AAG GGG AAG AAA
GTT TAC ACG AGA AGT GTA TAC CTT TTA CGA AAT GCT TTC CCC TTC TTT   624
Gln Met Cys Ser Ser His Met Glu Asn Ala Lys Glu Gly Lys Lys 210                     215                     220
ATT GAG TAT TTA AAA AAT GGG GAT GGA GGA AAG GCC AAC ATA ACG
TAA CTC ATA AAT TTT TTA CCC CTA CCT CCT TTC CGG TTG TAT TGC       672
```

FIG. 2D

```
     Ile Glu Tyr Leu Lys Asn Asn Gly Asp Gly Gly Lys Ala Asn Ile Thr
     225                         230                         235                         240
     GAT AGC CAA ATG GAG GAG GTA GGT AAC TAT GTT AGC AAA GCT GAG CAC
     CTA TCG GTT TAC CTC CTC CAT CCA TTG ATA CAA TCG TTT CGA CTC GTG   720

Asp Ser Gln Met Glu Glu Val Gly Asn Tyr Val Ser Lys Ala Glu His
                             245                         250                         255
     GCC TTT CAC ACA GAA GCA CAG GTA GAC AAA ACT AAA GCC TTT TGC
     CGG AAA GTG TGT CTT CGT GTC CAT CTG TTT TGA TTT CGG AAA ACG       768

Ala Phe His Thr Val Glu Ala Gln Val Asp Lys Thr Lys Ala Phe Cys
                                         260                         265                         270
     GAA TCC ATC GTA GCT TAT GTA ACG AAG ATG GAC AAC CTG TTT AAC GAA
     CTT AGG TAG CAT CGA ATA CAT TGC TTC TAC CTG TTG GAC AAA TTG CTT   816

Glu Ser Ile Val Ala Tyr Val Thr Lys Met Asp Asn Leu Phe Asn Glu
                 275                         280                         285
     TCG TTA ATG AAA GAA GTG AAA GTG AAG TGT GAA CTT TTT TTA CTA CTT
     AGC AAT TAC CTT CAC TTC ACA TTC ACT CTT GAA AAA AAT GAT CTA CTT   864

Ser Leu Met Lys Glu Val Lys Val Lys Cys Glu Lys Lys Asn Asp Glu
```

FIG. 2E

```
                      290                     295                     300
                GCG GAG AAA TAT TCG GCC AAA TTA AAT TTT GGC ATG CCG TAC GAT GGT AGA ATT AAA        912
                CGC CTC TTT ATA AGC CGG TTT AAT TTA AAA CCG TAC CTA CCA TCT TAA TTT
                Ala Glu Lys Tyr Ser Ala Lys Leu Lys Pro Tyr Asp Gly Arg Ile Lys
                305                     310                     315                     320
                GCG CGA GTG AGT GAG AAT GAA AGA AAA ATA AGC GAA TTG AAG GAA AAA        960
                CGC GCT CAC TCA CTC TTA CTT TCT TAT TCG CTT AAC TTC CTT TTT
                Ala Arg Val Ser Glu Asn Glu Arg Lys Ile Ser Glu Leu Lys Glu Lys
                                        325                     330                     335
                GCC AAA GTT GAG AAG GAA TCC CAA CTT AAC GAT GTT TCC ACG        1008
                CGG TTT CAA CTC TTC CTT AGG AGC GTT GAA CTA CAA AGG TGC
                Ala Lys Val Glu Lys Lys Glu Ser Gln Leu Asn Asp Val Ser Thr
                                        340                     345                     350
                AAG TCG TTA CAA ATA GAT AAT TGC AGA CAA CAG CTT GAC AGC GTT        1056
                TTC AGC AAT GTT TAT CTA TTA ACG TCT GTC GAA CTG TCG CAA
                Lys Ser Leu Leu Gln Ile Asp Asn Cys Arg Gln Gln Leu Asp Ser Val
                355                     360                     365
                TTG TCA AAC ATT GGA AGG GTG AAA CAA AAT GCA CTT GAA TAT TTC GAT        1104
                AAC AGT TTG TAA CCT TCC CAC TTT GTT TTA CGT GAA CTT ATA AAG CTA
```

FIG. 2F

Leu Ser Asn Ile Gly Arg Val Lys Gln Asn Ala Leu Gln Tyr Phe Asp
                 370                         380
TCG GCT GAT AAA TCG ATG AAG TCC GTT TTG CCT ATA AGC GAA TTG GAT        1152
AGC CGA CTA TTT AGC TAC TTC AGG CAA AAC GGA TAT TCG CTT AAC CCA

Ser Ala Asp Lys Ser Met Lys Ser Val Leu Pro Ile Ser Glu Leu Gly
385                         390                         400
GCC GAA AAA TCG CTA GAC AAA GTA AAA GCG GCT AAG GAA AGT TAT GAG        1200
CGG CTT TTT AGC GAT CTG TTT CAT TTT CGC CGA TTC CTT TCA ATA CTC

Ala Glu Lys Ser Leu Asp Lys Val Lys Ala Ala Lys Glu Ser Tyr Glu
                     405                         415
AAA AAT TTG GAA ACC GTT CAA AAT GAA ATG AGT CGT ATT AAT GTG GAA        1248
TTT TTA AAC CTT TGG CAA GTT TTA CTT TAC TCA GCA TAA TTA CAC CTT

Lys Asn Leu Glu Thr Val Gln Asn Glu Met Ser Arg Ile Asn Val Glu
                 420                         425     430
GAA GGA AGT CCT ACC GAC ATA GAC AAA ATA ACT GAC ATA GAA AAT            1296
CTT CCT TCA GGA CTG CTG TAT TTT TAT TGA CTG TAT CTT TTA

Glu Gly Ser Leu Thr Asp Ile Asp Lys Lys Ile Thr Asp Ile Glu Asn

FIG. 2G

```
          435                       440                       445
GAC TTG CTA AAA ATG AAG AAA TAT GAA GAA GGG TTA CTA CAA AAG       1344
CTG AAC GAT TTT TAC TTC TTT GTT ATA CTT CCC AAT GAT GTT TTC
Asp Leu Leu Lys Met Lys Lys Gln Tyr Glu Glu Gly Leu Leu Gln Lys 450                       455                       460
ATT AAA GAA ATA AAT GCG GAT AAG AGG AAG AGT AAT TTC GAA TTA GTA GGA  1392
TAA TTT CTT TAT TTA CGC CTA TTC TCC TTC TCA TTA AAG CTT CAT CCT
Ile Lys Glu Asn Ala Asp Lys Arg Lys Ser Asn Phe Glu Leu Val Gly 465                       470                       475                       480
AGC GAA ATA AAC GCC TTG CTG GAT CCA AGC ACG TCT ATT TTT ATT AAA      1440
TCG CTT TAT TTG CGG GAC CTA GGT TCG TGC AGA TAA AAA TAA TTT
Ser Glu Ile Asn Ala Leu Leu Asp Pro Ser Thr Ser Ile Phe Ile Lys 485                       490                       495
TTA AAA TTA AAG GAA TAT GAC ATG ACC GGC GAT TTA AAA AAT TAC GGT       1488
AAT TTT AAT TTC CTT ATA CTG TAC TGG CCG CTA AAT TTT TTA ATG CCA
Leu Lys Leu Lys Glu Tyr Asp Met Thr Gly Asp Leu Lys Asn Tyr Gly 500                       505                       510
GTT AAA ATG AAT GAA ATT CAT GGT GAA TTT ACC AAA TCG TAC AAT TTG     1536
CAA TTT TAC TTA CTT TAA GTA CCA CTT AAA TGG TTT AGC ATG TTA AAC
```

FIG. 2H

```
         Val Lys Met Asn Glu Ile His Gly Glu Phe Thr Lys Ser Tyr Asn Leu
                                 520                 525
         ATA GAA ACC CAT TTG TCC AAT GCT ACA GAT TAT TCT GTG ACG TTT GAG
         TAT CTT TGG GTA AAC AGG TTA CGA TGT CTA ATA AGA CAC TGC AAA CTC  1575

Ile Glu Thr His Leu Ser Asn Ala Thr Asp Tyr Ser Val Thr Phe Glu
              530                         535                 540
         AAG GCC CAA AGT TTA AGG GAA CTA GCA GAG AAG CTC TTC GAA CAT CTC
         TTC CGG GTT TCA AAT TCC CTT GAT CGT CTC TTC GAG AAG CTT GTA GAG  1623

Lys Ala Gln Ser Leu Arg Glu Leu Ala Glu Lys Leu Phe Glu His Leu
              545                         550                 555                     560
         AGA AGA GAG GAG CTC CTC GCG ATC TTT CTG AAT GAT ATT AAA AAG
         TCT TCT CTC GAG GAG CGC TAG AAA GAC TTA CTA TAA TTT TTC  1671

Arg Arg Glu Glu Ala Ile Phe Leu Asn Asp Ile Lys Lys
                              565                     570                 575
         GTG GAA TCG TTA AAA CTG CTA AAA GAA ATG ATG AAA AAG GTG AGT GCC
         CAC CTT AGC AAT TTT GAC GAT TTT CTT TAC TAC TTT TTC CAC TCA CGG  1719

Val Glu Ser Leu Lys Leu Leu Lys Glu Met Met Lys Lys Val Ser Ala
```

FIG. 2I

```
GAA TAT GAA GGT ATG AAA AGA GAC CAT ACG AGT GTT AGT CAG CTT GTA    1767
CTT ATA CTT CCA TAC TTT TCT CTG GTA TGC TCA CAA TCA GTC GAA CAT
Glu Tyr Glu Gly Met Lys Arg Asp His Thr Ser Val Ser Gln Leu Val
         580              585              590

CAG GAT ATG AAG ACA ATT GTT GAT GAG CTG AAA ACA CTG AAT GAT ATA    1815
GTC CTA TAC TTC TGT TAA CAA CTA CTC GAC TTT TGT GAC TTA CTA TAT
Gln Asp Met Lys Thr Ile Val Asp Glu Leu Lys Thr Leu Asn Asp Ile
         595              600              605

AGC GAA TGT TCG AGC GTG CTA AAC AAT GTA GTT ATA GTT AAA AAG    1863
TCG CTT ACA AGC TCG CAC GAT TTG TTA CAT CAA TAT CAA TTT TTC
Ser Glu Cys Ser Ser Val Leu Asn Asn Val Val Ser Ile Val Lys Lys
         610              615              620

GTT AAA GAG TCG AAA CAT GCA GAC TAT AGG TCC CTG CGC TTA TCG TAC    1911
CAA TTT CTC AGC TTT GTA CGT CTG ATA AGG AGA GCG AAT AGC ATG
Val Lys Glu Ser Lys His Ala Asp Tyr Arg Arg Asp Ala Asn Ser Met
         625              630              635              640

TAT GAA AGT ATG GTA ACT CTG GCA AAT TAT CTA AGC GAT GAG GCT    1959
ATA CTT TCA TAC CAT TGA GAC CGT TTA ATA AAG GAT TCG CTA CTC CGA
Tyr Glu Ser Met Val Thr Leu Ala Asn Tyr Leu Ser Asp Glu Ala
              645              650              655
```

FIG. 2J

```
                                                                      2007
Tyr Glu Ser Met Val Thr Leu Ala Asn Tyr Phe Leu Ser Asp Glu Ala
         660
AAA ATT TCA TCA GGA AT
TTT TAA AGT AGT CCT TA
Lys Ile Ser Ser Gly Xxx
```

FIG. 3
FIG. 4
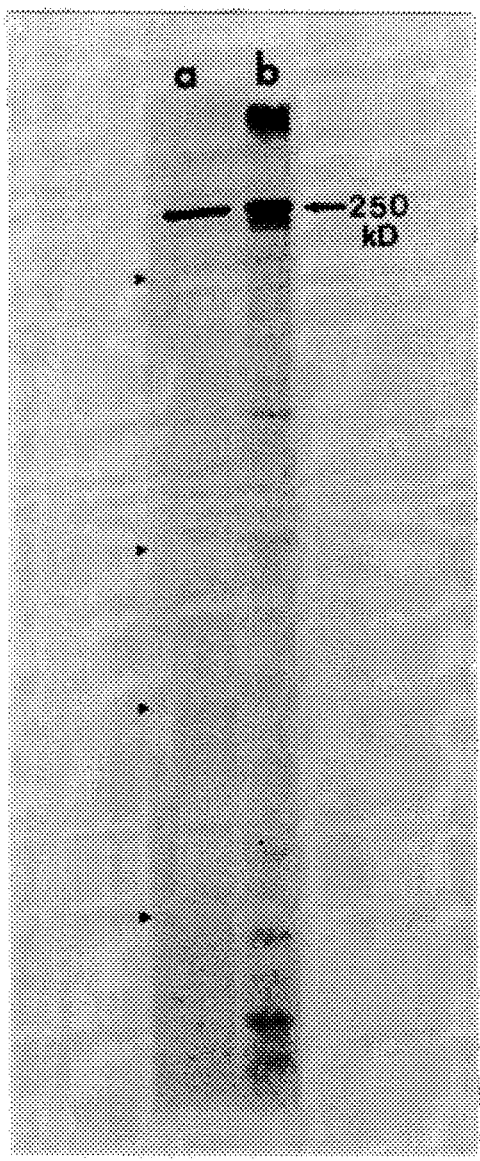
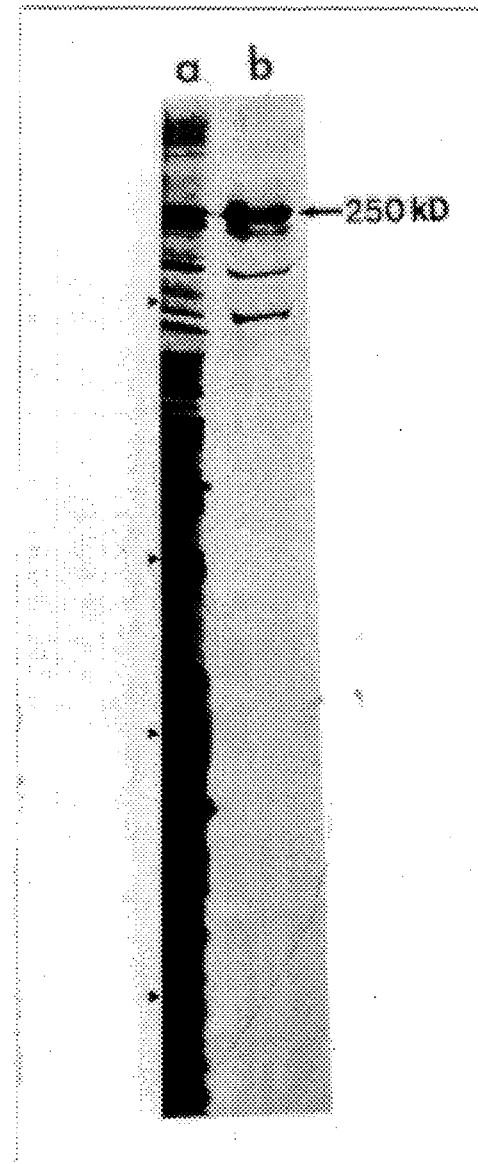

FIG. 13A

```
1                    5                                        10                                       15
TCC GTG CAA CCT TTA CTT GGA TCG AAA TCT CGA CAA GGG GAT TAC CAA            48
AGG CAC GTT GGA AAT GAA CCT AGC TTT AGA GCT AGC GTT CCC CTA ATG GTT
Ser Val Gln Pro Leu Leu Gly Ser Lys Ser Arg Gln Gly Asp Tyr Gln 20                                       25                                       30
ACG GGC GCA TTC ACA AAT GGA TAT GCA CAA ATG GAT ATG CAC ATG            96
TGC CCA CCG CGT AAG TGT TTA CCT ATA CGT GTT TAC CTA TAC GTG TAC
Thr Gly Ala Phe Thr Asn Gly Tyr Ala Gln Met Asp Met His Met 35                                       40                                       45
GAA GAC GAC GAG GAT GAT CTA CTA GGT GGA GGA GAG CCC AAA GAC TTA AAT            144
CTT CTG CTG CTC CTA CTA GAT CCA CCT CCT CTC GGG TTT CTG AAT TTA
Glu Asp Asp Glu Asp Asp Leu Leu Gly Gly Gly Glu Pro Lys Asp Leu Asn 50                                       55                                       60
TTC CCG GGC ATG ATA CGA AAT CGA AAT GAT TTT AAA AAT TTA ACA            192
AAG GGC CCG TAC TAT GCT TTA GCT TTA CTA AAA TTT TTA AAT TGT
Phe Pro Gly Met Ile Arg Asn Arg Asn Asp Phe Lys Asn Leu Thr 65                                       70                                       75                                       80
CCT ATC ATG AAT GAA AAC GGA GAA CCA ATT ATC ACG AAC AAG TGT TTG            240
GGA TAG TAC TTA CTT TTG CCT CTT GGT TAA TAG TGC TTG TTC ACA AAC
Pro Ile Met Asn Glu Asn Gly Glu Pro Ile Ile Thr Asn Lys Cys Leu
```

FIG. 13B

```
                    85                         90                         95
AAC GAA ACG AGG AAA GTA GTT CCC CTT AAT GAA CCT AAT GAA TCG TTC TCG AGT
TTG CTT TGC TCC TTT CAT CAA GGG GAA TTA CTT AGC AAG AGC TCA        288
Asn Glu Thr Arg Lys Val Val Pro Leu Pro Asn Glu Ser Phe Ser Ser 100                        105                        110
CAT CAG GTC GAC ATG GGA GAG CAC GTG AAG CAC TTA CTT GTG AAG GAC ACG AGC
GTA GTC CAG CTG TAC CCT CTC GTG CAC TTA GAA CAC TTC CTG TGC TCG        336
His Gln Val Asp Met Gly Glu His Val Lys His Leu Leu Val Lys Asp Thr Ser 115                        120                        125
AAA ACG AAC GCA ACC TCC ACA AAC GAC TTT CAT CAA CCT
TTT TGC TTG CGT TGG AGG TGT GTG CTG AAA GTA GTT GGA        384
Lys Thr Asn Ala Thr Ser Thr Asn Asp Phe His Gln Pro 130                        135                        140
CAC ATG AAC GCA GAA ATA AGT TCA AAA GAG GTG AAG GAA GAG CGA TGG
GTG TAC TTG CGT CTT TAT ATA AGT TCA CTC CAC CTT CTC GCT ACC        432
His Met Asn Ala Glu Ile Ser Ser Lys Glu Val Lys Glu Glu Arg Trp 145                        150                        155                        160
ATA AAA TGT AAT TCC TTC ATT TAT GAG CCT AGT GCT AAT TAT GCG CAA
TAT TTT ACA TTA AGG AAG TAA ATA CTC GGA TCA CGA TTA ATA CGC GTT        480
Ile Lys Cys Asn Ser Phe Ile Tyr Glu Pro Ser Ala Asn Tyr Ala Gln
```

FIG. 13C

```
                    165                          175
AAA AAT ATG AGG GAG GAT CAT CCT TGT GAA GTT CCA AAT GAT CCA TGT
TTT TTA TAC TCC CTC CTA GTA GGA ACA CTT CAA GGT TTA CTA GGT ACA   528
Lys Asn Met Arg Glu Asp His Pro Cys Glu Val Pro Asn Asp Pro Cys
              180                          190
AAG AAT GAA GAA AAT TGT CTC CAC GGA GTT CTC CAC CAC TCC
TTC CTT CTT ACA GAG GTG CCT TTA CAA GAG GTG GTG AGG                576
Lys Asn Glu Glu Asn Cys Leu His Gly Val Leu His His Ser
          195                          205
AGT GAA CAG AAC GAT TCG GTT GCC CAT TCA CAA GTT CAC GAC TGT TAC
TCA CTT GTC TTG AGC CAA CGG GTA AGT GTT CAA GTG CTG ACA ATG       624
Ser Glu Gln Asn Asp Ser Val Ala His Ser Gln Val His Asp Cys Tyr
      210                          220
AAC TAT AGG TTC ATT AAG AAT TAC GTA GAT GAA ATG ACG AAC AAG CCA
TTG ATA TCC AAG TAA TTC TTA ATG CAT CTA CTT TAC TGC TTG TTC GGT   672
Asn Tyr Arg Phe Ile Lys Asn Tyr Val Asp Glu Met Thr Asn Lys Pro
  225                          235                          240
AGA AGC AAA AAG AAC GAG GAA CTC ACT TTG GGT GAT AAA TCA TTT
TCT TCG TTT TTC TTG CTC CTT GAG TGA AAC CCA CTA TTT AGT AAA       720
Arg Ser Lys Lys Asn Glu Glu Leu Thr Leu Gly Asp Lys Ser Phe
```

FIG. 13D

```
                    245
GAT GTG GAA AGG TAT TTG AAA AAG TTC CCC CTT CCG AAG GAT GAT ACA    768
CTA CAC CTT TCC ATA AAC TTT CTT GAA GGC CTT CTA CTA TGT
Asp Val Glu Arg Tyr Leu Lys Lys Phe Pro Leu Pro Lys Asp Asp Thr
           260                            255
CTG CGG GGT GAT TCT TAT GGT ATA CCC GTG TTC GCA ACT GGG GAA GGA    816
GAC GCC CCA AGA ATA TGC AAG CAC CGT TGA CCC CTT CCT
Leu Arg Gly Asp Ser Tyr Gly Ile Pro Val Phe Ala Thr Gly Glu Gly
       275                    265                270
TCA ACC GAT CAA ACG AAT GTA CAG GTG AAT GCG GCG AAT GCG CTT        864
AGT TGG CTA GTT TGC TTA CAT GTC CAC CGC GTC CGC GAA
Ser Thr Asp Gln Thr Asn Val Gln Val His Gln Val Asn Ala Leu
   290                            285
ATG CCT GTG CAG AGT CAT CTT CAG GGA GGA GTA AAC CCA GAG CCT        912
TAC GGA CAC GTC TCA GTA GAA GTC CCT CAT GGT CTC GGA
Met Pro Val Gln Ser His Leu Gln Gly Gly Val Glu Asn Pro Glu Pro
305                            295                    300
CTC CCC AAT GGT GAC AAT CAC AAG AAG AGT TCC ACC CTC TGT GGC CAA    960
GAG GGG TTA CCA CTG TTA GTG TTC TCA AGG TGG GAG ACA CCG GTT
Leu Pro Asn Gly Asp Asn His Lys Lys Ser Ser Thr Leu Cys Gly Gln
                                      315                  320
                            310
```

FIG. 13E

```
      325                     330                     335
TTG AAT AAT TAC GGC AAC GTT AGC AAT GAA GAA CTT TCC GCA AAT GAG GTA    1008
AAC TTA TTA ATG CCG TTG CAA TCG CTT CTT AGG CGT TTA CTC CAT
Leu Asn Asn Tyr Gly Asn Val Ser Asn Glu Glu Leu Ser Ala Asn Glu Val 340                     345                     350
TTG AAC AAG GGA GTC GAA AGA TGT ATT GAT AAC CTA TGT AAA TTT ATG TTA    1056
AAC TTG TTC CCT CAG CTT TCT ACA CTA TTG GAT ACA TTT ATG CTA AAT
Leu Asn Lys Gly Val Glu Arg Cys Ile Asp Asn Leu Cys Lys Tyr Asp Leu 355                     360                     365
GCT AGC CAT TCA CAA AGT ATA AAT ATT CTG CGA AAT GAG GAT TCT AAC        1104
CGA TCG GTA AGT TCA TAT TTA TAA GAC GCT TTA CTC CTA AGA TTG
Ala Ser His Ser Gln Ser Ile Asn Ile Leu Arg Asn Glu Asp Ser Asn 370                     375                     380
CAA TTG TCT CTA CAG ACT TGA GAA AAT GAA TCC AAG GGT GAG GAA CAG AAC    1152
GTT AAC AGA GAT GTC TGA CTT TTA CTT AGG TTC CCA CTC CTT GTC TTG
Gln Leu Ser Leu Gln Thr Glu Asn Glu Ser Lys Gly Glu Glu Gln Asn 385                     390                     395              400
GCA GAT CAA GTC TTT AAA TTT GCA ATG AAG TAC TTC TAT ATA CAA AAC TAT TTA    1200
CGT CTA GTT CAG AAA TTT CAG GTC ACG TAC TTG AAG ATA TAT GTT TTG ATA AAT
Ala Asp Gln Val Phe Lys Asn Ile Ala Met Lys Tyr Ile Gln Asn Tyr Leu
```

FIG. 13F

```
                    405                    410                    415
AGA AAT TAC AGA AAG ATG ATT ATC GAG GGA AAG CAT CTT AAT            1248
TCT TTA ATG TCT TTC TAC TAA TAG CTC CCT TTC GTA GAA TTA
Arg Asn Tyr Arg Lys Met Ile Ile Glu Gly Lys His Leu Asn 420                    425                    430
GTT GGT CCG ATT CAT GGC GTA GCA AGG GAG TGT CCA CCA CAC GCT        1296
CAA CCA GGC TAA GTA CCG CAT CGT TCC CTC ACA GGT AGC GTG CGA
Val Gly Pro Ile His Gly Val Ala Arg Glu Cys Pro Pro His Ala 435                    440                    445
ATG GCT ACC ACC AGT GCG GGT AAT TAC ATG TCA ACT TGT CTT GGC TCC   1344
TAC CGA TGG TGG TCA CGC CCA TTA ATG TAC AGT TGA ACA GAA CCG AGG
Met Ala Thr Thr Ser Ala Gly Asn Tyr Met Ser Thr Cys Leu Gly Ser 450                    455                    460
CCC CTC AGC AAC CAT ATG CAC GTG TAC CCC GAC CAT ATG AAC AAC TCC   1392
GGG GAG TCG TTG GTA TAC GTG CAC ATG GGG CTG GTA TAC TTG TTG AGG
Pro Leu Ser Asn His Met His Val Tyr Pro Asp His Met Asn Asn Ser 465                    470             474                    480
TTC GCT ACT TGT TCT TTG AAG GAA AAC GCA AAC CTC AAG GGG AGT ATC   1440
AAG CGA TGA ACA AGA AAC TTC CTT TTG CGT TTG GAG TTC CCC TCA TAG
Phe Ala Thr Cys Ser Leu Lys Glu Asn Ala Asn Leu Lys Gly Ser Ile
```

FIG. 13G

```
AAA ATA ACT GTC CCG CTA TTT CTC CTG TAC ATA ACC AAT GCC TAT GCC
TTT TAT TGA CAG GGC GAT AAA GAG GAC ATG TAT TGG TTA CGG ATA CGG   1488
Lys Ile Thr Val Pro Leu Phe Leu Leu Tyr Ile Thr Asn Ala Tyr Ala
                    485                     490              495

ACT GTT GAT GTC AGT GGA AGC AAC ACC AAG AGT GCG CAT GCG ATG CGT
TGA CAA CTA CAG TCA CCT TCG TTG TGG TTC TCA CGC GTA CGC TAC GCA   1536
Thr Val Asp Val Ser Gly Ser Asn Thr Lys Ser Ala His Ala Met Arg
            500                     505                     510

TGG AAA AAG CTG AAA AAA ATT ATG AAC GAA ATA ATT TTT GGA TTT
ACC TTT TTC GAC TTT TTT TAA TAC TTG CTT TAT TAA AAA CCT AAA       1575
Trp Lys Lys Leu Lys Lys Ile Met Asn Glu Ile Ile Phe Gly Phe
                    515                     520         525

ACC TAT GCA GAT GCG GAT CTA TAC GTA GAG CAA CTT GAA CTA TGT AAT ATT
TGG ATA CGT CTA CGC CTA GAT CAT CTC GTT CTT GAA GAT ACA TTA TAA   1623
Thr Tyr Ala Asp Ala Asp Leu Tyr Val Glu Gln Leu Glu Leu Cys Asn Ile
                        530                     535         540

AAA AAG TGC TTC ATT CAA GTA TTG GAT TAC TTG AAG GAA TAT AAC CCT
TTT TTC ACG AAG TAA GTT CAT AAC CTA ATG AAC TTC CTT ATA TTG GGA   1671
Lys Lys Cys Phe Ile Gln Val Leu Asp Tyr Leu Lys Glu Tyr Asn Pro
545                     550                     555         560
```

FIG. 13H

```
                          565                    570                              575
CAA TGG GTC TGT AGC AAG CCT GGG GAT GCA TAC TTT AAA TAT CAT TTT CGG        1719
GTT ACC CAG ACA TCG TTC GGA CCC CTA CGT ATG ATA GTA AAA GCC
Gln Trp Val Cys Ser Lys Pro Gly Asp Ala Tyr Phe Tyr His Phe Arg 580                              585
AAA ATT ATG GCA ATC AAC AGC TCC TAC GTG GAT GTG AAT TC
TTT TAA TAC CGT TAG TTG TCG AGG ATG CAC CTA CTT AG
Lys Ile Met Ala Ile Asn Ser Ser Tyr Val Asp Val Asn Ser
```

MEROZOITE ANTIGENS LOCALIZED AT THE APICAL END OF THE PARASITE

This is a continuation of application Ser. No. PCT/US90/01849 filed Apr. 3, 1990, which is a continuation-in-part of application Ser. No. 07/608,639, filed Nov. 2, 1990, abandoned, which is a continuation of application Ser. No. 07/334,041, filed Apr. 5, 1989, abandoned. PCT/US90/01849 is also a continuation-in-part of application Ser. No. 334,270, filed Apr. 6, 1989, abandoned.

FIELD OF THE INVENTION

This invention relates to antigens of malarial merozoite origin localized at the apical end of the parasite; and to synthetic versions, fragments and derivatives of such antigens which (a) are immunochemically reactive with antibodies recognizing the native merozoite apical end protein, and/or (b) can be used to elicit monoclonal or polyclonal antibodies that recognize the native apical antigen, and/or (c) bind with receptor-like specificity to a Duffy blood group antigen present on the surface of red blood cells (said Duffy antigen serving as the ligand); and/or (d) recognize erythrocyte surface structures involved in parasite invasion of erythrocytes. The antigens of the invention are necessary in the process of invasion of red blood cells by the merozoites. This invention also relates to peptides and polypeptides comprising synthetic versions, fragments, derivatives or analogs of the native malarial polypeptides that have the foregoing properties. This invention also relates to nucleic acids encoding such antigens and to nucleic acids hybridizing therewith.

In another aspect, this invention also relates to compositions and methods for inhibiting invasion of susceptible primate (including simian) cells by malarial merozoites and inhibiting the propagation of a malarial organism in the red blood cells of a mammal. These compositions and methods employ the antigens of the invention or antibodies immunochemically reactive with these antigens.

The invention further relates to vaccine and drug compositions useful for inhibiting the propagation of a malarial organism in the red blood cells of a mammal.

BACKGROUND OF THE INVENTION

All the clinical and pathological features of malaria are attributed solely to the parasitic stages of the asexual erythrocytic cycle which occurs in the vertebrate host. The propagation of this cycle in a host is dependent upon extracellular merozoites attaching to and invading susceptible erythrocytes (red blood cells). This attachment and initiation of invasion by malaria merozoites is mediated through specific interactions between parasite receptors and ligand molecules on the erythrocyte plasma membrane. Butcher, G. A., et al, *Nature* 244:40, 1973; Miller, L. B., et al, *J. Exp. Med.* 138: 1597, 1983.

The invasion of host erythrocytes by parasite merozoites involves a defined series of events (Bannister, L. H., et al., *Parasitology* 71:483-491, 1975; Dvorak, J. A., et al., *Science*, 187:748-749, 1975; Aikawa, et al., *J. Cell Biol.*, 77:72-82, 1978) which include: 1) initial recognition and attachment of the merozoite to the erythrocyte membrane; 2) orientation of the merozoite so that its apical end is apposed to (i.e. oriented towards) the erythrocyte membrane; 3) formation of a junction between the apical end of the merozoite and the erythrocyte; 4) invagination of the erythrocyte membrane to form a vacuole; 5) movement of the merozoite into the vacuole by a moving Junction around the merozoite; 6) closure of the erythrocyte and vacuole membranes resulting in the parasite residing within a parasite-bearing vacuole in the host erythrocyte. This process must involve the complex interaction of numerous components of both parasite and host origin.

In principle, strategic interference with one or more of the foregoing invasion events could prevent invasion, thereby precluding the intra-erythrocytic propagation of the parasite, and eventually diminishing or abolishing infection. However, despite considerable research efforts worldwide, the complexity of the parasite and of its relationship with its host, it has not yet been possible to discover a satisfactory solution for prevention or abatement of the blood stage of malaria. Accordingly, there is a felt need in the field for materials and methods that could be used to accomplish such a goal (e.g. by directly interfering with invasion or by elucidating the mechanism of erythrocyte invasion and assisting in the identification of means for raising preventive and therapeutic barriers against such invasion).

The malarial species *P. vivax*, one of the four species infective to humans, is a particularly difficult target for such efforts. This parasite is in, short supply and cannot be cultured in vitro, as has been possible with *P. knowlesi* (a simian malaria parasite) and *P. falciparum* (another human malaria parasite). Although *P. vivax* bears substantial phylogenetic similarity to *P. knowlesi*, the two species are different in many important respects. For example, *P. vivax* is not infective at all to many simian species and infection is poorly established in others, whereas *P. knowlesi* is poorly infective to humans while readily infecting many simian species.

The preinvasion orientation of malarial merozoites (such that the epical end is apposite to the erythrocyte surface) indicates that the epical end plays an important role in the invasion process but this role is complex and is not yet clearly understood. Therefore, identification of proteins or other structural features specific to the epical end will provide a better understanding of the molecular mechanism of the invasion process.

Moreover, antigens specifically associated with the apical end are likely to play an important role in apical-end functions, including but not limited to the invasion process and particularly its substages (3) and (4) mentioned above, and therefore at least some such antigens may constitute targets for new antimalarial drugs and/or potential candidates for new vaccines against malaria.

Antibodies raised against an epical end-associated antigen would be useful in studies of parasite morphology and structure; could be used in diagnostic or other serological assays designed to determine infection and measure its extent; and could be also used to inhibit invasion by interfering with erythrocyte binding of the apical antigen or otherwise impeding the function of an apical antigen indispensable to the invasion process.

Human beings lacking the Duffy blood group (Marsh, W. L., *CRC Crit. Rev. Clin. Lab. Sci.* 5:387-412, 1975) on the surface of their erythrocytes are refractory to infection by *Plasmodium vivax* (Miller, L. H., et al, *N. Engl. J. Med.* 295: 302-304, 1976). These erythrocytes are not susceptible to invasion by either *P. vivax* (Barnwell, J. W., et al., *J. Exp. Med.* 169:1795, 1989 or the phylogenetically related, and more easily maintained, simian malaria, *P. knowlesi* (Miller, L. H., et al., *Science* 189:561-563, 1975; Mason, S. J., et al., *Br. J. Haematol.* 36:327-335, 1977), in vitro. *P. knowlesi* merozoites will attach to and orient their apical ends towards the Duffy-negative erythrocyte membrane but no junction is formed between the cells (Miller, L. H., et al., *J. Exp. Med.* 149: 172–185, 1979. These observations lead to the hypothesis that the 35–46 kilodalton (kD) Duffy blood group glycoprotein (Hadley, T. J., et al., *Science* 223:597–599, 1984) is an essential ligand in the invasion process of human erythrocytes by *P. vivax*. (A *P. falciparum* merozoite antigen has been identified but it binds to glycophorin.) This hypothesis was further supported by the ability of polyclonal antisera against Fy[a] Duffy determinant and proteolytic cleavage of the Duffy determinants from erythrocytes to inhibit *P. knowlesi* invasion of human erythrocytes (Miller, L. H., et al.; Mason, S. J., et al., supra). The specificity of this interaction has been demonstrated by blocking the ability of *P. vivax* merozoites to invade human erythrocytes with both intact and F(ab) fragments of an anti-Duffy monoclonal antibody (Barnwell, J. W., et al., supra) directed against the newly described Fy[6] determinant of the Duffy glycoprotein (Nichols, M. E., et al., *J. Exp. Med.* 166:776–785, 1987).

Accordingly, the present inventors sought to take advantage of this interaction between *P. vivax* or *P. knowlesi* merozoites and the erythrocyte surface (including, but not limited to, the Duffy glycoprotein) to elucidate the molecular nature of Plasmodium invasion of host erythrocytes and to devise means and methods useful against malaria.

SUMMARY OF THE INVENTION

In one aspect, the present invention is directed to antigens localized at the apical end of the malarial merozoite surface said antigens being involved in the invasion process and being immunochemically reactive with antibodies raised against malaria (particularly including *P. vivax*) blood stage parasites; and to synthetic proteins (including but not limited to fusion proteins) polypeptides and peptide fragments and analogs of such antigens that are themselves immunochemically reactive with antibodies raised against the apical-end localized malarial antigens. One particular subgroup of antigens within the invention concerns polypeptides of malarial merozoite origin that bind specifically to a Duffy blood group antigen (said antigen being present on the surface of susceptible mammalian red blood cells) and are necessary in the process of invasion of red blood cells by merozoites; and compounds comprising synthetic versions, fragments, derivatives or analogs of these polypeptides which maintain the ability to bind to the erythrocyte Duffy antigen.

In another aspect, the present invention is directed to nucleic acids encoding such antigens, proteins and peptides and to nucleic acids hybridizing therewith.

In yet another aspect, the present invention is directed to materials (including vaccines) and methods for inhibiting the intraerythrocytic propagation of malaria; and to materials (e.g. antibodies, including monoclonal antibodies) recognizing the immunochemically reactive compounds on the surface of *P. vivax* merozoites and useful inter alia in qualitative and quantitative diagnostic assays for assessing the presence and extent of malarial parasitemia.

This invention also provides a method for inhibiting invasion of susceptible mammalian blood cells by malarial merozoites which comprises exposing said merozoites to the presence of an invasion-inhibiting effective amount of antibodies recognizing a parasite polypeptide binding to a Duffy blood group antigen.

This invention also provides a method of inhibiting the propagation of a malarial organism in the red blood cells of a susceptible mammal in need of such treatment which comprises administering to said mammal an effective amount of an apical-end-derived peptide or polypeptide (capable of raising antibodies against the parasite antigen from which it was derived and/or inhibiting the binding between said parasite antigen and its erythrocyte receptor). One subgroup of this method involves use of a peptide capable of binding to a human Duffy blood group antigen, in an amount effective to inhibit the invasion of said red blood cells by said malarial organism.

The invention also provides a composition (such as a vaccine) useful for inhibiting the propagation of a malarial organism in the red blood cells of a susceptible meal, the composition comprising an effective amount of a peptide within the scope of this invention (e.g. a peptide capable of binding to a human Duffy blood group antigen) and optionally comprising a pharmaceutically acceptable carrier or diluent.

BRIEF DESCRIPTION OF THE DRAWINGS

FIGS. 1A through 1R and 2A through 2J depict the nucleotide and amino acid sequences of a merozoite apical-end-localized protein in accordance with the invention. These sequences correspond to two different portions of the native MAEP (insert 5.3:FIG. 1A; insert 7.2:FIG. 1B).

FIG. 3 shows SDS-PAGE gels; lane a, molecular weight markers; lane b, purified native MAEP antigen which was isolated by binding to rabbit erythrocytes; lane c, native MAEP antigen, as a 250 kD protein band, immunoprecipitated by hyperimmune monkey antibodies specifically recognizing the fusion protein from phage clone 5.3.

FIG. 4, lane b shows SDS-PAGE gels of native MAEP antigen (previously immunoprecipitated with specific antibody) binding to rabbit erythrocytes and compared with total culture supernatants from infected monkey erythrocytes (lane a).

FIG. 13A through 13H depicts the amino acid and encoding nucleotide sequences of a 1.8 kb cloned insert of the Pk DAP gene.

DETAILED DESCRIPTION OF THE INVENTION

Figure 5:
FIG. 5 also containing SDS-PAGE gels) shows that hyperimmune monkey antibody specifically recognizing the fusion protein from clone 7.2 also recognizes the native 250 kD MAEP (lane b); rabbit antibodies raised against the fusion protein from clone 5.3 also recognize the native MAEP (lane c) and immunoprecipitate native MAEP (lane d); native purified MAEP binds to human erythrocytes (lane e) and to rabbit erythrocytes (lane f) (lane a contains total supernatant samples).
Figure 6:
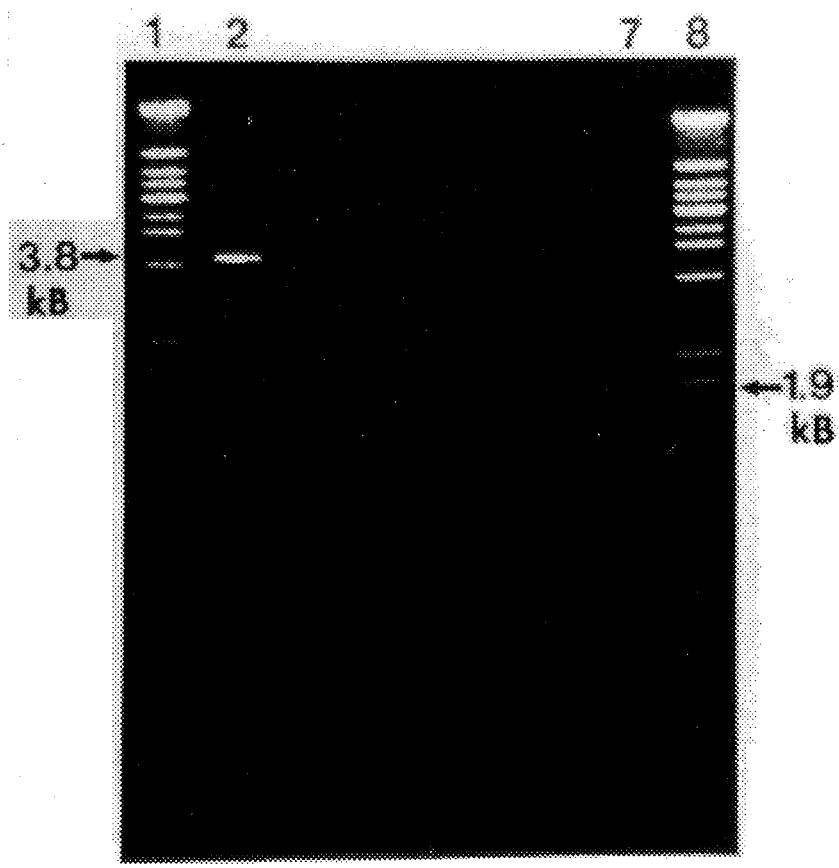
FIG. 6 shows an ethidium bromide-stained agarose gel containing parasite DNA (lanes 2 and 7) coding for portions of the native MAEP and DNA size markers (lanes 1 and 8).

As used herein, the following terms shall have the following meanings:

(a) "immunochemically reactive" refers to the ability of a peptide or protein to recognize (i.e. bind to) an antibody and vice versa (i.e. the ability of an antibody to recognize a peptide or protein);

(b) "antigen" means a peptide or protein that either elicits antibodies in meals or is "immunochemically reactive" (as defined above) with antibodies elicited by immunization with another antigen;

(c) "MAEP" or "merozoite epical-end protein" means any natural or synthetic peptide, protein or antigen which is immunochemically reactive with antibodies recognizing a native merozoite protein localized at the epical end of malarial parasites;

(d) "DAP" or "Duffy-associating protein" (PvDAP) means a particular malarial MAEP which specifically binds to the Duffy blood group antigen of primate erythrocytes such that in the absence of this protein invasion of the erythrocytes by the parasite cannot be accomplished.

(e) "MAEP-based peptide" means a peptide, polypeptide or antigen that comprises a synthetic version, or a derivative, fragment or analog of MAEP; accordingly a "DAP-based peptide" is a particular MAEP based peptide that binds to the Duffy blood group of primate erythrocytes;

(f) "compound comprising MAEP or a MAEP-based peptide" means a compound or conjugate or synthetic construct which is or comprises an amino acid sequence corresponding to MAEP or a MAEP-based peptide (both as defined above); and (g) "parasitemia" in malarial infection is defined as the presence of at least one parasite in 10,000 blood cells of the host.

In addition, the term "peptide" shall be deemed to include polypeptides, antigens or proteins except if the context requires otherwise; and the term "synthetic" shall be deemed to encompass substances synthesized by classical chemical techniques and substances synthesized by recombinant DNA techniques.

In one preferred embodiment, the invention is directed to a surface 250 kD protein isolated from P. vivax merozoites which is localized (on the merozoite surface) at the apical end of the parasite and has the property of binding to human reticulocytes (i.e. non-nucleated immature erythrocytes) and consequently is involved (and is potentially important) in erythrocyte invasion by P. vivax. (P. vivax is known to invade reticulocytes almost exclusively.) Another important property of this protein is that it is specifically recognized by antibodies elicited against whole blood stage parasites and in turn elicits antibodies recognizing the native protein on the merozoite surface. Furthermore, antibodies recognizing this protein have been shown to partially inhibit merozoite invasion of human erythrocytes in vitro. Therefore, the MAEP antigens of this invention constitute potential components for a malaria vaccine. (Other embodiments of this invention include synthetic versions of this protein as well as fragments, derivatives and analogs thereof having the same immunogenic, immunorecognition and/or inhibiting properties.)

Further characteristics of this protein include a molecular weight of about 250 kD; a highly hydrophilic, highly charged region which extends over at least 50% of its amino acid sequence; the total absence of repetitive sequences (in contrast to other known blood-stage and sporozoite-stage antigens); a probable largely alpha-helix secondary structure with beta turns as determined by algorithms for deducing protein secondary structure (Chou-Fasman and Robson-Garnier); and at least 15 potential N-linked glycosylation sites.

This MAEP protein binds to the surface of susceptible erythrocytes (reticulocytes) from *P. vivax* susceptible humans and primates and also binds to rabbit erythrocytes (despite the fact that rabbits are not susceptible to *P. vivax*).

No malarial protein having all of these characteristics has been described in the literature.

Based on the phylogenetic similarity between *P. vivax*, *P. cynomolgi*, and *P. knowlesi*, it is likely that a corresponding MAEP will be found to be present in *P. knowlesi* and *P. cynomolgi*. Whether such a *P. knowlesi* protein exists can be determined by the same methods described herein and variations thereof within the skill of the art. (For example, antibodies specifically recognizing *P. vivax* MAEP can be used to extract *P. knowlesi* MAEP based on the extensive cross-reactivity of antibodies against each of those species. Alternatively, antisera against *P. knowlesi* can be separated based on their ability to bind fusion proteins expressed from a genomic *P. knowlesi* DNA library and antibodies binding each *P. knowlesi* fusion protein can be used in immunofluorescence assays for localization of their antigenic determinants at the apical end of *P. knowlesi* merozoites.) Other malarial species, such as *P. falciparum*, may also possess MAEP's which can be identified and sequenced using no more than ordinary skill in the art in light of the present description, and hence the present invention is not limited to *P. vivax*. Whatever the plasmodial species of their derivation, MAEPs can be used as described in the Background section to design potential drugs and antigens for combatting malaria and to gain a better understanding of the biology and pathology of this disease.

As will be described below, a native *P. vivax* MAEP was identified by screening a lambda gt 11 genomic *P. vivax* DNA expression library with sera from *Saimiri aciureus* monkeys hyperimmunized with *P. vivax* schizonts, a procedure which yielded a restricted antibody response (directed against 12 antigens).

Monkey antibodies reacting specifically with expression products from two clones of the genomic library (the clones being designated 5.3 and 7.2, respectively) recognized this native MAEP by immunofluorescence and were used to immunoprecipitate it from *P. vivax* merozoite $^{35}$S-methionine labeled extracts.

DNA from the positive clones (5.3 and 7.2) was expressed to yield MAEP's as beta-galactosidase fusion proteins. Both fusion proteins elicited antibodies which also recognized the native MAEP. Accordingly, such fusion proteins are fully within the scope of this invention. Moreover the results of these experiments show that the native MAEP (or synthetic versions thereof) and antigenic fragments thereof are immunogenic and elicit antibodies which recognize the native MAEP on the merozoite apical surface. Hence, MAEPs which comprise less than the entire sequence of the native MAEP are antigenic and (as will be shown below) can be used to elicit antibodies that inhibit the binding of native MAEP to mammalian (including human) erythrocytes. It is therefore contemplated that synthetic antigens will be constructed containing one or more subsequences (optionally with further deletions or substitutions of one or more amino acids) of the native MAEP such that the synthetic constructs will bear one or preferably more antigenic determinants of the native MAEP and/or maintain the ability of eliciting antibodies that recognize the native MAEP. Of course, heterologous sequences can also be added or interposed in such constructs (as can amino acid or subsequence dilution or substitutions) to enhance their immunogenic ability (and/or activity of the resulting antibodies in inhibiting binding of the merozoite MAEP to erythrocytes and/or the invasion of erythrocytes by the parasite). Methods for accomplishing this are well-known in the art. Additionally, peptides based on these antigens and having desired immunochemical properties can be synthesized, e.g. as described in Merrifield, R. B. *Fed. Proc. Am. Soc. Ex. Biol.* 21: 412, 1962 and *J. Am. Chem. Soc.* 85: 2149, 1963; Mitchel, A. R. et al., *J. Am. Chem. Soc.* 98: 7357, 1976; Tam, J. et al., *J. Am. Chem. Soc.* 105: 6442, 1983.

Genomic library (phage) clone 5.3 contained approximately 3.8 kb of *P. vivax* DNA; phage clone 7.2 contained approximately 1.9 kb of *P. vivax* DNA; DNA from these clones did not cross-hybridize, indicating that essentially different portions of MAEP are encoded by each fragment.

The MAEP-encoding nucleotide sequence for *P. vivax* clone 5.3 (in which the sequence is present in an open reading frame) was determined and is set forth in FIG. 1A through 1R, along with the amino acid sequence it encodes. To obtain this DNA sequence the *P. vivax* DNA insert from the lambda gt 11 recombinant clone 5.3 was isolated and subcloned into the plasmid pBluescript (obtained from Stratagens) and a series of clones containing overlapping deletions of the 5.3 insert were created using the exonuclease-III/mung-bean-nuclease deletion kit obtained from Stratagens and the supplier's protocol slightly modified to use 1 microgram of DNA per deletion as opposed to 5 micrograms as suggested by the supplier. The inserts contained within the series of clones were sequenced using the well-known Sanger et al. technique (*Proc. Nat'l Acad. Sci.* 74:5463–5467, 1977), T3 and T7 primers provided by Stratagens, and sequencing reagents supplied in the well-known SEQUENASE™ Kit (U.S. Biochemical Co.). DNA sequences obtained were analyzed using Pustell DNA Sequence Analysis Software provided by IBL.

Elucidation of the remainder of the amino acid sequence of the native MAEP is well within the skill of the art. The *P. vivax* DNA insert of clone 7.2 also has been subcloned into pBluescript and its sequence elucidated (FIG. 1A). Overlapping clones containing deleted sequences are being created and sequenced using the same reagents and protocols used to obtain the sequence of the *P. vivax* 5.3 DNA insert.

Concurrently, the *P. vivax* DNA inserts from the 5.3 and 7.2 clones have been isolated, labelled with $^{32}$p dCTP using a random-primed labeling kit (Boeringer-Mannheim) and used to screen a nonexpression lambda-Fix/genomic *P. vivax* DNA library (lambda-Fix and other lambda replacement vectors suitable to clone fragments of DNA in the 9–23 kb range can be obtained from Stratagene) to identify the entire gene encoding this *P. vivax* MAEP. Hybridization of $^{32}$P-labeled 5.3 and 7.2 inserts to *P. vivax* Bam HI-restricted DNA reveals in both cases a single hybridizing band. Thus, in accordance with Stratagene's protocols for using lamBda-Fix, a lambda-Fix/*P. vivax* genomic library was made using Bam Hi-digested *P. vivax* DNA. The library was packaged using GIGAPACK II™ packaging extracts and accompanying protocols from Stratagens. Additionally, a portion of this library may be packaged using GIGAPACK XL™ extracts from Stratagens which preferentially package large DNA fragments, thus increasing the likelihood that the gene encoding the MAEP and contained in *P. vivax* DNA fragments of 20–23 kb will be cloned. The MAEP-encoding gene may alternatively be identified in other *P. vivax* libraries constructed according to known methods, or otherwise available, provided the inserted *P. vivax* DNA contains the MAEP gene in its entirety. Once identified, positive phage can be plaque-purified, prepared in large liquid lysate cultures (Kern, J., Brenner, S., and Barnett, H. L., *Meth. Enzymol.* 101:3–19, 1981) and purified using, e.g., LAMB-DASORB™ (Promega). The entire gene and its flanking sequences can then be characterized; initially a restriction map can be obtained in which inserts 5.3 and 7.2 can be placed accordingly and appropriate subclones can be placed accordingly and appropriate subclones can be prepared in order to obtain the remaining sequence of MAEP, i.e., the segment not encoded within the inserts of these two clones.

The MAEP's of the present invention can be extracted from merozoites by immunoprecipitation and other well-known techniques in the art including chromatographic techniques e.g., using a suitable polysaccharide as the adsorbent and ionic, nonionic and/or affinity chromatography conditions (including but not limited to high performance liquid chromatography). In addition, immunoaffinity chromatography (using as the adsorbent polyclonal or monoclonal antibodies to the MAEP protein bound to a suitable support, such as a polysaccharide support) could be used as part of the chromatographic purification scheme. A specific MAEP immunoaffinity purification protocol is the following:

Monoclonal antibodies specific for MAEP are immobilized on a cross-linked agarose support (such as a chromatography column), the MAEP-containing extracts or fluids (e.g. serum from an infected individual) are contacted with the immobilized antibody and the purified MAEP is thereafter eluted from the immune complex formed.

In addition to the foregoing immunoaffinity chromatography, ion-exchange chromatography e.g. anion-exchange chromatography on e.g. DEAE-Sepharose (Pharmacia Fine Chemicals, Piscataway, N.J.) or molecular sizing FPLC (high-performance liquid chromatography from Pharmacia) can be used alone or sequentially with (before or after) the immunoaffinity column.

The MAEP's of the present invention can also be produced by recombinant DNA techniques. For example, MAEP DNA can be expressed in any known expression system preferably in a glycosylation-providing expression system such as yeast (European Pat. Appln. Ser. No. $A_3$ 175261 of Chiron Corporation published Mar. 26, 1986 corresponding to U.S. patent application Ser. No. 650,323, filed Sep. 12, 1984) or in mammalian cells.

Analysis (by Pustell Sequence Analysis Programs, copyright J. Pustell, 1987, 1988 which were also used to elucidate the sequences of FIGS. 1A through 1R and 2A through 2J)) of the primary amino acid structure of FIG. 1A through 1R revealed 15 N-linked potential glycosylation sites; hence, use of a glycosylation-providing expression system, such as a yeast or mammalian cell culture (such as COS-1 cell available from the American Type Culture Collection (ATCC) under accession number ATCC CRL 1650 or WOP-32 cells also available from the ATCC under accession No. ATCC CRL 8806) is preferred. Use of DNA linkers to establish appropriate enzymatic cleavage sites may be desirable, but design and use of such linkers can be accomplished by methods well-known in the art (alternatively, appropriate linkers can be commercially obtained).

Inter alia, the MAEP's of the present invention are useful in understanding the mechanism of erythrocyte invasion by the blood stage of *P. vivax* (and possibly also by the blood stage of other malarial species). Also, monoclonal antibodies raised using synthetic or native MAEP's as the immunogen and recognizing the native MAEP can be used in sensitive serologic diagnostic assays, given that the native MAEP is localized in the apical region of the blood stage *P. vivax* parasite.

Monoclonal antibodies against MAEP's can be raised using e.g. the now classical Kohler, G. & Milstein, C. technique (*Nature* 256:495–497, 1975). Such monoclonal antibodies can then be used in diagnostic assays as follows:

Serum from infected or susceptible individuals can be screened for the presence of MAEP antigen or antibody to MAEP antigen, using well-known Enzyme-Linked Immunosolvent Assay (ELISA) or another assay system. For example, a first monoclonal anti-MAEP can be bound to a solid support; incubated with sera from the individual to be tested (unbound sera will be washed with PBS or another suitable buffer); and incubated with a second labelled monoclonal anti-MAEP directed to a different MAEP epitope. After washing to remove unbound second antibody, the complexes can be detected and counted. See McDougall, J. S. et al. *J. Immunol, Math.* 76:171–183, 1985.

Alternatively, antibody to MAEP circulating in the individual's serum can be detected by ELISA according to the method of Engevall, E., *Methods in Enzymology*, 70:419–439, 1981. Briefly, MAEP is bound to a solid support (e.g. on a microtiter plate) unbound antigen is removed; the plate is incubated with sera from the individual to be tested; unbound sera are removed; and an anti-immunoglobulin antibody (suitably labelled) (e.g. goat-anti-human IgG) is used to reveal the bound antigen-antibody complexes. These assays can also be performed using MAEPs from parasites infective to other species, e.g. monkeys.

Rabbit antibodies raised against fusion proteins from the phage clone 5.3 (described below) specifically inhibited the binding of native MAEP antigen to human red blood cells. Squirrel monkey antibodies affinity-purified on clone 7.2 fusion protein inhibited merozoite invasion of these cells in vitro to the extent of 48% (data not shown). This indicates that the MAEPs of the present invention constitute suitable candidates for a vaccine against propagation of malarial parasite in host red blood cells.

To be used in vaccine preparations, the MAEP's of the present invention will be used in immunogenically effective amounts alone or in combination with other vaccine components (in fact, MAEP's for this purpose can be made by recombinant DNA techniques and can be co-expressed with such other active vaccine components) with or without any suitable carrier, an adjuvant or a diluent all of which should be pharmaceutically acceptable. Repeat immunizations may be necessary to enable the host to mount an immune response. Both amounts of immunogen and immunization protocols can be determined experimentally, as is well-known in the art, using animal (e.g. primate) models followed by clinical testing in humans. Information on vaccine compositions and immunization is described for example in U.S. Pat. No. 4,767,622 of Ristic (Aug. 30, 1988); U.S. Pat. No. 4,735,799 of Patarroyo (Apr. 5, 1988) and Patarroyo, M. E., et al., *Nature* 332:158, 1988; and published European Application $A_1$ 250,261 (published Dec. 23, 1987) of the Wellcome Foundation.

In another preferred embodiment, this invention is directed to a purified DAP of malarial origin (or a synthetic version or fragment thereof) capable of binding to a Duffy blood group antigen with a receptor-like specificity (wherein the Duffy antigen serves as a ligand and DAP serves as a receptor).

Duffy blood group antigen is present in primate red blood cells, especially including human red blood cells, specifically the human red blood cells and other primate erythrocytes susceptible to *P. vivax* having the $Fy^6$ determinant or phenotype (Nichols, M. E. et al, *J. Exp. Med.* 366:776, 1987). Such an Fy$^6$ phenotype may comprise Fy(a⁻b⁺), Fy(a⁺b⁺) and Fy(a⁺b⁻) phenotypes of human erythrocytes but not Duffy negative human erythrocytes (Fya⁻b⁻). Duffy-positive red blood cells also include simian cells, e.g., Aotus monkey erythrocytes and erythrocytes of other simians and apes susceptible to *P. knowlesi* or *P. vivax* malaria. The Duffy glycoprotein human Duffy positive erythrocytes is present in approximately 13,000 copies per cell.

DAP of *P. vivax* origin has been designated *P. vivax* Duffy-associating protein (PvDAP) and has been determined to possess an apparent molecular weight (by SDS-PAGE) in the range from about 135,000 to about 140,000 daltons (135–140kD); DAP from *P. knowlesi* is designated herein PkDAP (or Pk135) and has a molecular weight (by SDS-PAGE) of about 135 kD. SDS-PAGE was performed by the method of Laemli, U. K., *Nature* 227:680–685, 1970, as a discontinuous buffer system and at a polyacrylamide concentration of 7.5%.

Other characteristics of DAP proteins include immunologic relatedness between PvDAP and PkDAP in that antibodies raised against one recognize (and bind to) the other; the possibility that the DAP proteins are products of proteolysis of higher-molecular weight parasite protein structures; the fact that the receptor-ligand interaction between DAP and the Duffy antigen is essential for erythrocyte invasion by merozoites; the inability of DAP to bind to erythrocytes from *P. vivax*-insusceptible host red blood cells; and the inability of PkDAP to bind to erythrocytes from *P. knowlesi*-insusceptible hosts.

PvDAP binds with equal affinity to all Duffy-positive human phenotypes and to Aotus erythrocytes but PkDAP binds with higher affinity to human Fy(a⁻b⁺) erythrocytes than to other Duffy positive human erythrocytes, yet all human Duffy-positive erythrecytes are equally susceptible to *P. vivax* invasion. PvDAP appears to interact with different determinants on the Duffy glycoprotein than PkDAP, which may account for the different erythrocyte host specificities of the two parasites. Also, the PvDAP and PkDAP bind to erythrocytes with different specificities (which can be only partially explained by known characteristics of Duffy antigens). Thus, the DAP proteins from the two malarial species are distinct although they both recognize and bind to Duffy antigen.

The DAP proteins may be isolated from natural sources, i.e. parasite material (preferably previously selected for ability to bind to erythrocytes) by immunoprecipitation with antibodies raised against *P. knowlesi* merozoites, regardless of the malarial species provenance of the DAP (since the *P. knowlesi* antisera recognizing PkDAP cross-react with PvDAP). Preferably, however, DAP may be isolated by chromatographic techniques, including affinity chromatography e.g., using purified Duffy antigen as the affinity adsorbent immobilized on a polysaccharide support as described above for MAEPs followed by immunoaffinity chromatography, e.g., using polyclonal anti-*P. knowlesi* recognizing DAP as the immunoadsorbent. Most preferably, purified DAP can be used to elicit monoclonal antibodies to DAP (e.g., according to the well-known technique of Kohler, G. and Milstein, C., *Nature* 256:495–497, 1975) and the monoclonal antibodies can be used as the immunoaffinity adsorbent (bound to a polysaccharide or cellulose support) in subsequent purification of DAP from natural sources. In addition (or alternatively), high-performance liquid chromatography (HPLC) including reverse-phase HPLC can be used.

Like other MAEPs, DAP and DAP-based peptides can also be prepared by synthetic techniques including chemical peptide synthesis and recombinant DNA techniques, as described further below.

DAP and DAP-based peptides may be used as immunogens to raise antibodies in the host (or in another host or in vitro, as in passive immunization) which will recognize and bind to the native DAP protein on the merozoite surface. Thus, immunogenic compounds comprising DAP and DAP-based peptides may be used in vaccine preparations to confer prophylactic immunity against the blood stage of malaria or to confer therapeutic immunity by preventing (totally or partially) further intraerythrocytic propagation of the disease in the host through interference with the binding of DAP with the Duffy antigen. The necessity of DAP binding to its ligand for invasion to occur can be shown in vitro. Pk DAP antisera inhibit in vitro invasion of human erythrocytes by *P. knowlesi* merozoites by at least 50% and anti-Duffy antigen antibodies inhibit *P. vivax* and *P. knowlesi* invasion by at least 90%. If a DAP-based peptide is not immunogenic, its structure may be altered to confer immunogenic properties to it such that the resulting construct will elicit antibodies recognizing native DAP.

It should be noted that 100% inhibition of merozoite-erythrocyte binding by a compound (or vaccine containing it, or antibody) according to the present invention is not necessary for these materials to be useful. Any substantial decrease in the extent of infection (as measured, e.g. by the extent of parasitemia would substantially attenuate the clinical symptoms and substantially increase the probability for survival and recovery of the host. For example, a 50% inhibition of erythrocyte-parasite binding would produce a substantial decrease in parasitemia.

Compounds comprising DAP-based peptides may be used in drug design to design antagonists to the DAP receptor (i.e. molecules that bind to but do not activate DAP) and thus prevent Duffy-native DAP ligand-receptor interactions or may be used as competitive inhibitors of the Duffy ligand-DAP receptor binding. In particular, DAP-based peptides preferably of relatively short length (e.g. molecular weight 5,000 or less) comprising fragments or derivatives of the amino acid sequence DAP protein and binding to the Duffy blood group antigen (preferably with at least substantially the same affinity as the native DAP on the merozoite surface) can be used to inhibit the receptor-ligand binding and thus prevent invasion of erythrocytes.

To prepare such DAP-based peptides of the competitive-inhibitor (i.e. not the antagonist) type, or of the immunogenic type, peptides corresponding to various fragments of DAP can be synthesized (optionally derivatized, e.g. incompletely deprotected peptides or peptides also containing non-DAP amino acid sequences or sequence-terminated, i.e. deletion, peptides) using, e.g., the well-known automated peptide-synthesis procedures based on Merrifield, R. B., *Fed. Proc. Fed. Am. Soc. Ex. Biol.* 21:412, 1962; *J. Chem. Soc.* 85:2149, 1963 or recombinant DNA methods, also well-known and widely used.

These peptides can be then tested for their ability to bind Duffy antigen or block DAP binding, e.g. by the erythocyte binding assay of Example 1, and/or by the erythrocyte invasion of Example 8. Also, competitive versions of these assays in microtiter plates can be used as follows: known quantities of native DAP or recombinant DAP (1.0–100 nanograms) are mixed with candidate peptides (1.0–100 ug) to determine if peptides inhibit binding of DAP to purified Duffy antigen (or Fy$^6$). The Duffy glycoprotein (or Fy$^6$) could be plated in microtiter wells or to native Duffy antigen on erythrocytes. Conversely, it may be seen if DAP inhibits peptide binding to Duffy antigen. Either DAP or peptides could be radiolabled ($^{125}$I or $^{35}$S) to provide a means of detecting functional activity.

Nonlimiting examples of recombinant DNA techniques that can be used include those disclosed in U.S. Pat. Nos. 4,419,450; 4,418,194; 4,414,150; 4,399,216; 4,394,443; 4,356,270; 4,351,901 and 4,237,224. In addition, synthetic DNA sequences may be prepared encoding the desired amino acid sequences, such DNA sequences can be inserted in suitable cloning vectors, and the vectors used to transform various organisms which will then express the desired product. See U.S. Pat. Nos. 4,273,875; 4,304,863; 4,332,901; 4,403,036; 4,363,877; and 4,349,629. See also European Application No. A$_2$ 166,410 published Jan. 1, 1986 and No. A$_1$ 192,626 published Aug. 27, 1986 (which specifically discloses recombinant DNA techniques for screening, sequencing and making malarial origin peptides); and PCT International Application W087/05607 published Sep. 24, 1987.

The DAP-based synthetic peptides can thus be tested using, e.g., the assay system of Example 1 for inhibition of the DAP-Duffy binding. Successful inhibitors can then be incorporated in drug and vaccine preparations using methods and formulations well-known in the art.

It should be noted that compounds, mixtures or compositions comprising DAP-peptide amino acid sequences as well as other components are within the scope of the invention. For example, DAP-peptide sequences can be co-expressed (e.g., in the manner of fusion proteins) with (or bound or ligated or conjugated to) other immunogenic or immune-response enhancing heterologous or malarial-derived peptides and proteins, or nonpeptide entities such as carriers, adjuvants, immunogens mimicking other parasite antigens etc. Alternatively, compositions in accordance with the present inventions can comprise mixtures of such ingredients as separate chemical species.

It will be understood that analogous uses, procedures and manipulations can be applied to other MAEPs within the scope of the invention and to their receptors. Such general procedures are exemplified in U.S. Pat. No. 4,835,259 issued May 30, 1989 (although this patent is directed to *P. falciparum* glycoproteins which apparently are not epical-localized).

Another aspect of this invention also provides nucleic acid comprising nucleotide sequences encoding DAP or DAP-based peptides described above and nucleic acid hybridizing therewith. This invention further provides cDNA, i.e., nucleic acid which is complementary to the nucleic acids described in the preceding sentence. Methods for preparing such nucleic acid molecules are well-known in the art and the references cited above for preparation of the instant compounds can be used to prepare the nucleic acids encoding for them.

Yet another aspect of this invention provides a method for inhibiting invasion of susceptible primate blood cells by malarial merozoites which comprises exposing said merozoites to the presence of an invasion-inhibiting effective amount of antibodies raised against a compound comprising DAP or a DAP-based peptide and binding to primate Duffy blood group antigen. The step of exposing the malarial merozoites to the presence of an invasion inhibiting effective amount of antibodies recognizing a DAP or a DAP-based peptide binding to primate Duffy blood group antigen can be carried out in vitro. Alternatively, this step is carried out in vivo by immunization (or passive immunization) of a susceptible (or infected) host with DAP, or with a DAP-based peptide or a compound comprising either.

This invention also provides a method of inhibiting the propagation of a malarial organism in the red blood cells of a susceptible mammal which comprises administering to the mammal an immunogenically effective amount of a compound or composition comprising DAP or DAP-based peptide (or another MAEP or MAEP-based peptide), such an amount being effective to elicit antibodies that inhibit invasion of the red blood cells by the malarial organism. In a further aspect, the compound or composition may be administered to a mammal which has been previously exposed to the malarial organism. In a still yet further aspect the polypeptide may be administered to a mammal prior to exposure of the mammal to the malarial organism.

Thus, contemplated are vaccines useful for inhibiting the propagation of a malarial organism in the red blood cells of a mammal comprising an effective amount of an immunogenic compound comprising DAP or DAP-based peptides capable of binding to a Duffy blood group antigen, and, optionally, a pharmaceutically acceptable carrier or diluent.

Vaccine preparations in accordance with the invention can be prepared as generally described in Voller, et al. (Ed) *New Trends and Developments in Vaccines,* University Park Press, Baltimore, Md., 1978. Conjugation of DAP-based peptides and DAP to macromolecules can be made as is well-known in the art, e.g. as disclosed in U.S. Pat. Nos. 4,372,945 or 4,474,757 and conjugation to multiple antigen peptide systems can be accomplished, e.g., as disclosed in Tam, J., *Proc. Nat'l. Acad. Sci.* (USA), 85:5409, 1988 using techniques described therein and in Mitchell, A. R. et al., *J. Am. Chem. Soc.* 98:7357, 1976. Finally, encapsulation in liposomes can be accomplished, e.g., as described in U.S. Pat. No. 4,235,877.

The DAP or DAP-based peptide compounds and constructs or mixtures thereof will be typically formulated in vaccine compositions comprising a pharmaceutically acceptable medium or diluent (e.g. an aqueous solution, preferably at physiological pH). Optionally, the immunogenic ingredient or ingredients can be admixed with or adsorbed to any known pharmaceutically acceptable carrier (e.g. a macromolecule) or adjuvant, such as killed Bordetella, tetanus toxoid, diphtheria toxoid, muramyl dipeptide, aluminum hydroxide, saponin, etc.

The amount of DAP or DAP-based peptide will vary depending upon the specific immunogen, the response it elicits in various subjects, and the presence or absence of heterologous carrier or adjuvant. Generally, amounts within the range from about 1 to about 1,000 micrograms of DAP or peptide are contemplated. Optimal amounts can be ascertained by routine experimentation involving measurement of antibody titers and other parameters of primate immune response, as is well-known in the art. Repeat immunizations are preferred. The foregoing vaccine discussion is also applicable to other MAEPs.

Additional information on vaccine preparations and protocols is well-known and readily available in the art. See, for example, European Application No. $A_1$ 191,748 of SmithKline Beckman published on Aug. 20, 1986; European Patent Application No. $A_1$ 192,626 of SmithKline Beckman et al. published Aug. 27, 1986; U.S. Pat. Nos. 4,693,994; 4,707,357; 4,735,799; and 4,767,622.

All cited patents, patent applications and literature are incorporated by reference in their entirety.

The present invention is further described below by reference to specific examples which are intended to illustrate it without limiting its scope.

The invention is further described below by reference to specific examples which are intended only to illustrate the invention without limiting its scope.

EXAMPLE 1

Screening of Genomic DNA Library

A lambda gt 11/*P. vivax* genomic DNA expression library was constructed simply by ligating *P. vivax* DNA predigested with Eco R1 into the Eco R1 cloning site of lambda gt 11 (Young, R. A., and Davis, R. W., *Proc. Nat'l Acad. Sci. USA* 80:1194, 1983) and packaging the resulting ligation mix using Packagene™ extracts purchased from Promega (lambda gt 11 was also purchased from Promega). However, another mode of construction of a genomic DNA library could have been used with optional suitable modification of the subsequent expression strategy.

A *Saimiri sciureus* monkey was hyperimmunized with *P. vivax* schizonts, by intravenous infection with schizont-infected erythrocytes from an infected Saimiri monkey. The injection was repeated three times.

Following this, the monkey was injected intramuscularly with inactivated schizonts twice in complete Freund's adjuvant and once in incomplete Freund's adjuvant.

A four- to six-week waiting period was interposed between successive injections. The resulting antisera contained a very restricted antibody response (directed against 12 antigens).

The antisera were used to screen the lambda gt 11/*P. vivax* genomic DNA library, expressed in *E. coli* cells Y1090 (obtained from Stratagens). Lambda gt 11 recombinant phage expressing proteins that reacted positively with this hyperimmune serum were individually reacted with the hyperimmune serum, and those antibodies that reacted specifically with each recombinant, protein-expressing phage were purified as is well known in the art using a plaque adsorption and elution methodology (Hall et al., *Nature* 311:374, London, 1984). Essentially, phage plaques expressing individual recombinant proteins were overlayed with a nitrocellulose filter that had been impregnated with Isopropyl beta-D-thiogalactopyranoside (Sigma Chemical Company) and incubated for 3 hours at 37° C. to allow the expression of the proteins and their adherence to the nitrocellulose filters. The specific-reacting monkey antibodies were purified by adsorption of the monkey immune sera to the protein of these filters, followed by extensive washes in a Tris Borate Saline/Tween solution and elution with 0.2M glycine, pH 2.5. These antibody preparations were dialyzed against phosphate buffered saline. Antibodies purified in this manner from the lambda gt 11 clones 5.3 and 7.2 recognized the apical end of *P. vivax* merozoites by immunofluorescence and immunoprecipitated the 250 kd MAEP antigen from $^{35}$S-methionine labeled parasite extracts (FIG. 3).

The 5.3 and 7.2 lambda gt 11 recombinant phage were used to infect Y1088 cells (obtained from Stratagene) to obtain lysogens suitable for the growth of large recombinant phage preparations. Phage were prepared from these lysogens essentially as described for the production of lambda gt 11 phage in *DNA Cloning 1: A Practical Approach*, Glover, D. M., Editor, IRL Press 1986, Vol. 1, Chapter 2, Huynh, T. V., Young, R. A., and Davis, R. W. and the phage and their DNAs were purified using Lambdasorb™ and accompanying protocols from Promega. The DNA was then restricted using Eco R1 to cleave the phage DNA and release the cloned *P. vivax* inserts. These DNA digests were run on 1% agarose gels and the inserts released were purified from the gel using standard methodology, and were subcloned into pBluescript plasmids (Stratagene) as described above. FIG. 5 shows an aliquot of both 5.3 and 7.2 purified insert DNAs run next to DNA markers and stained with ethidium bromide. Their insert sizes are estimated at 3.8 kb and 1.9 kb, respectively (FIG. 5).

In parallel, the fusion proteins corresponding to positive clones 5.3 and 7.2 were affinity purified on anti-beta-galactosidase columns and used to immunize rabbits. Antibodies from the immune sera elicited with each fusion protein were shown to recognize the native MAEP antigen (see FIG. 5 lanes B and C wherein lane B shows proteins (including the MAEP) recognized by the whole immune rabbit sera and lane C shows the result of immunoprecipitation of MAEP with purified anti-5.3 antibody from the rabbit immune sera). Immunoprecipitation was conducted as described below.

EXAMPLE 2

Immunoprecipitation of MAEP

Purified monkey antibodies reacting with the fusion proteins of clones 5.3 and 7.2 from the experiments of Example 1 were used to immunoprecipitate native MAEP from parasite extracts.

Parasite extracts were prepared from purified *P. vivax* trophozoite-infected erythrocytes that were washed in RPMI-1640 tissue culture medium and incubated in RPMI-1640 medium which was 90% methionine-deficient (as described in Trager, W. et al., *Science* 193: 673, 1976) but supplemented with $^{35}$S-methionine (100 microcurie/ml) and 10% human AB serum. The parasites were then allowed to mature to schizonts at 37° C. The cells were then extracted in 1% Triton X-100 at 4° C. preferably in the presence of protease inhibitors (50 micrograms/ml each chymostatin and leupeptin, both from Sigma Chemical Co., St. Louis, Miss.). The cells were extracted for 0.5 hr. with agitation. After extraction, the solution was centrifuged to remove any particulate material.

Figure 7:
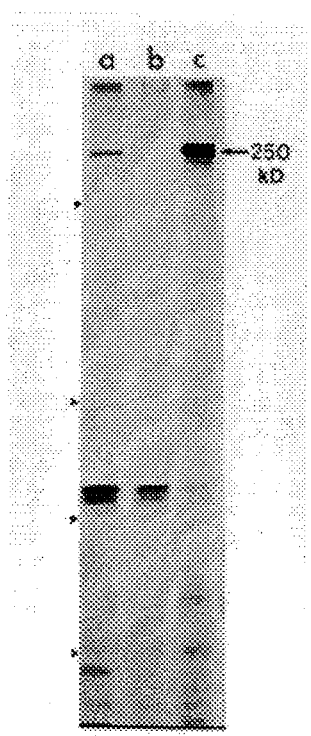
FIG. 7 (also containing SDS-PAGE gels) lane a, shows that hyperimmune monkey antibody specifically recognizes the 7.2 fusion protein and (lane c) monkey antibody specifically recognizes the 5.3 fusion protein and also recognizes native MAEP. Lane b is a control to show that these antibodies do not recognize phage proteins.

Specifically-reacting antibodies plaque-purified on clones 5.3 and 7.2 were incubated with labelled parasite proteins for 2 hours at 4° C. with rocking. Antigen-antibody complexes were precipitated, by adding Protein A Sepharose (Pharmacia Fine Chemicals, Piscataway, N.J.) and incubating for an additional two hours. The Sepharose was washed by centrifugation with Tris-buffered saline (containing 0.5% Triton X-100 and 5 mM EDTA and NETT (sodium chloride, ethylenediaminetetraacetate, Tris and Triton buffer) with 0.5 M NaCl). The complexes were dissociated by addition of an equal volume of SDS sample buffer containing mercaptoethanol, boiled and applied to a 7.5% SDS-PAGE (sodium dodecyl phosphate polyacrylamide gel electrophoresis). The results of the SDS-PAGE are shown in FIG. 7, lanes A and C and clearly show the presence of a single band 250 kD protein (indicated by the arrow at the same level). It is of course clear that any other method of identifying MAEP could have been used.

EXAMPLE 3

Immunofluorescence Studies

Antibodies specifically recognizing the fusion protein from clone 5.3 were incubated with smears of air-dried *P. vivax* schizonts and merozoites from an infected Saimiri monkey. Unbound antibody was washed with PBS. Anti-immunoglobulin antibodies were labelled with fluorescein isothiocyanate and were incubated with the smear-antibody complex. Unbound labelled antibody was again removed by washing. Fluorescence was detected using a Leitz epifluorescence microscope with a UV light source.

A unique fluorescing pattern was generated, which clearly showed that the specific antibody binds only to the apical end of the merozoite and hence the epical end localization of native MAEP was dramatically demonstrated.

It will be appreciated that Any other assay which detects the binding between antibody and native antigen on a cell surface could have been used.

EXAMPLE 4

Winding of MAEP to Rabbit Erythrocytes

MAEP-containing total culture supernatants (in which biosynthetically labeled infected erythrocytes were allowed to form merozoites which rupture naturally and release parasite proteins into the medium) were shown to bind to rabbit, as well as vivax-susceptible human and chimpanzee erythrocytes. In each case, erythrocytes ($1 \times 10^9$) were washed three times with PBS and then incubated with 300 microliters of labelled MAEP for 30 minutes at room temperature with rocking. The erythrocytes were then washed to remove unbound parasite proteins by centrifugation through silicone oil (550 Silicone oil, Dow Chemical Corp., Midland, Mich.) in an Eppendorf microlugs. The pellet was resuspended in 500 microliters RPMI-1640 and centrifuged through oil a second time. The erythrocyte pellet was then incubated with fifty microliters of 1M NaCl for 20 min., and centrifuged. The supernatant was mixed with an equal volume of SDS sample buffer containing mercaptoethanol. The samples were electrophoresed on a 7.5% SDS-PAGE and autoradiographed after impregnation with EnHance scintillation enhancer (MEN/Dupont, Wilmington, Del.). The result for rabbit erythrocytes is shown in FIG. 3, lane A. The 250 kD MAEP is clearly indicated by the arrow and is specifically immunoprecipitated by rabbit anti-5.3 fusion protein antibodies in lane B. The results of similar binding experiments using human erythrocytes were consistent: they are depicted in lane F of FIG. 5.

The binding experiment with the rabbit erythrocytes was repeated using immunoprecipitation-purified MAEP instead of total culture supernatants. The results are shown in FIG. 4 run on SDS-PAGE side-by-side with a gel containing total culture supernatants. The 250 kD MAEP is clearly present in both lane A (total supernatants) and lane B (rabbit erythrocytes).

EXAMPLE 5

Immunoprecipitation With Anti-Fusion Protein Antibodies

Polyclonal antibodies were raised against the fusion protein expressed from clone 5.3 (which were found to specifically react with antisera from *P. vivax* immunized Saimiri monkey. These antisera were then used to immunoprecipitate *P. vivax* protein bands from biosynthetically labeled ruptured erythrocyte culture supernatants. The results are shown in FIG. 5, with lane C evidencing specific precipitation of the 250 kD and showing that the anti-fusion protein antibodies recognize the same MAEP antigen as the antibodies from immune monkey antisera plaque-purified on clone 7.2

EXAMPLE 6

The Erythrocyte Binding Assay; Isolation of Native DAP Proteins

*P. vivax* (Belem strain) or *P. knowlesi* (H strain) infected blood drawn from Saimiri or Rhesus monkeys was purified and enriched as follows: *P. knowlesi* (H strain) parasites were cryopreserved in liquid nitrogen as ring-stage infected erythrocytes from Rhesus monkeys according to Barnwell, J. W., et al., *Infect. & Immun.* 40(3):985, 1983. Cryopreserved infected erythrocytes for use in invasion assays in vitro were thawed and cultured to the schizont stage in tissue culture medium RPMI-1640 supplemented with 30 mM HEPES, 2 gm/L D-glucose, hypoxanthine 50 mg/l, and 15% horse serum (Hyclone), or 15% human AB serum (complete medium) in an atmosphere of 5% $CO_2$/5% $O_2$/90% $N_2$ at 37° C. for 18–20 hours.

*P. vivax* (Belem) parasites were obtained from squirrel monkeys with synchronous infections when the majority of parasites were at the trophozoite stage. The heparinized blood with added ADP adenosine diphosphate (1 mg/ml) was passed sequentially over acid washed glass beads (0.11 mm diameter) and Whatman CF 11 cellulose columns to remove platelets and leukocytes and then centrifuged on 54% Percoll (Pharmacia Fine Chemicals, Piscataway, N.J.) to concentrate parasitized erythrocytes to >90% purity (Barnwell, J. W., et al., 1983, supra). Maturation of the parasites to mature schizonts was accomplished in RPMI-1640 supplemented with hypoxanthine (50 mg/l), D-glucose (2 mg/l) (Hyclone), BEPES or TES (35 mM), 10% human AB serum, and 10% fetal calf or horse serum (Hyclone) as above for *P. knowlesi*.

Late trophozoite to mid-schizont stage infected erythrocytes, with less than 5% uninfected cells, were cultured in RPMI-1640 (Trager, W., et al., *Science* 193:674–675, 1976) 90% methionine-deficient medium supplemented with $^{35}$S-methionine (100 uCi/ml) and 10% human antibody serum, 10% horse serum (Hyclone Laboratories, Logan, Utah) for *P. vivax* or 15% horse serum for *P. knowlesi*. The parasites were allowed to mature and rupture the infected erythrocytes. The culture supernatants were collected, centrifuged (500×g for 5 minutes, then 2700×g for 30 minutes at 4° C.) and stored at –70° C.

Figure 8:
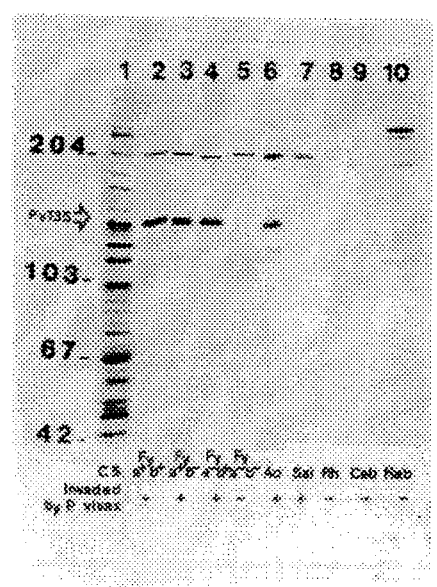
FIG. 8 is an autoradiograph of an SDS-PAGE gel of biosynthetically ($^{35}$S-methionine) labeled *P. vivax* proteins which bind to erythrocytes: Total culture supernatant diluted 1:20 with sample buffer (lane 1); proteins binding to human FY(a$^+$b$^+$6$^+$), Fy(a$^+$b$^-$6$^+$), Fy(a$^-$b$^+$6$^+$) and Fy(a$^-$b$^-$6$^-$) erythrocytes (lanes 2–5); Aotus, Saimiri, Rhesus and Cebus erythrocytes (lanes 6–9); and rabbit erythrocytes (lane 10). The 135 to 140 kilodalton (kD) *P. vivax* Duffy-associating protein, PvDAP, is indicated by the open arrow and molecular weight markers are indicated on the left.
Figure 9:
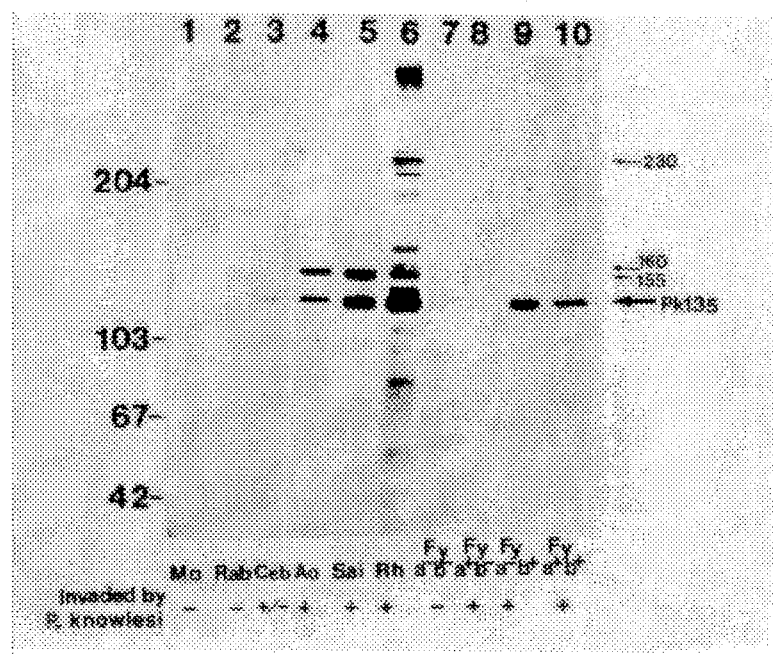
FIG. 9 an autoradiograph of an SDS-PAGE gel of metabolically labeled *P. knowlesi* proteins eluted from (i.e. binding to) mouse and rabbit erythrocytes (lanes 1 and 2); Cebus, Aotus, Saimiri and Rhesus erythrocytes (lanes 3–6); human Fy(a⁻b⁻6⁻), Fy(a⁺b⁻6⁺), Fy(a⁻b⁺6⁺) and Fy(a⁺b⁺6⁺) erythrocytes (lanes 7–10). The 135kD P. knowlesi Duffy-associating protein, Pk135, is indicated by the closed arrow on the right.

Erythrocytes ($1 \times 10^9$) from human or various simian origins (see FIGS. 8 and 9) were washed 3 times with phosphate buffered saline (PBS) and then incubated with 250 ul of culture supernatant for 30 minutes at room temperature with rocking. The erythrocytes were washed by centrifugation through silicone oil (550 Silicone oil, Dow Chemical Corp., Midland, Mich.) in an Eppendorf microfuge. The pellet was resuspended in 250 ul RPMI-1640 with 15% horse serum and centrifuged through oil a second time. The erythrocyte pellet was then incubated with 50 ul of 1M NaCl for 20 minutes, centrifuged and the supernatant mixed with an equal volume of 2×SDS sample buffer containing mercaptoethanol. The samples were electrophoresed on a 7.5% SDS polyacrylamide gel and autodiographed after impregnation with EnHance scintillation enhancer (NEN/Du Pont, Wilmington, Del.). The results for *P. vivax* DAP are shown in FIG. 8. Those for PkDAP are shown in FIG. 9.

Thus, the native DAP polypeptide from *P. vivax* was first identified using an assay in which biosynthetically labeled parasite proteins from culture supernatant were incubated with intact erythrocytes (Haynes, J. D., et al., *J. Exp. Med.* 167:1873–1881, 1988; Camus, D., et al., *Science* 230:553–556, 1985) PvDAP was eluted from these erythrocytes and isolated on SDS-PAGE (see FIG. 7). PvDAP has been determined to possess an apparent molecular weight in the range from about 135,000 to about 140,000 daltons, by sodium dodecyl sulfate polyacrylamide gel electrophoresis using biosynthetically ($^{35}$S-methionine) labelled *P. vivax* proteins released into culture supernatant after erythrocyte rupture. DAP is a minor component of the total parasite proteins present in the culture supernatant. PvDAP binds strongly to all three phenotypes of Duffy positive human erythrocytes, chimpanzee, and to Aotus (squirrel) monkey erythrocytes, which are also susceptible to P. vivax invasion. PvDAP does not, however, bind to erythrocytes from Duffy-negative humans or to simian erythrocytes from Rhesus and Cebus monkeys, which are not themselves susceptible to invasion by P. vivax. Erythrocytes from non-primates, such as mice and rabbits, also do not bind to PvDAP.

Applying the same technique of isolation to P. knowlesi culture supernatant instead of P. vivax, the existence of a 135 kD parasite protein (Pk135 or PkDAP) has been confirmed (Haynes, J. D., et al., supra). This P. knowlesi derived protein binds to Duffy-positive human erythrocytes but not to Duffy-negative erythrocytes. In contrast to PvDAP, PkDAP binds most intensely to $Fy(a^{-b+})$ human erythrocytes, less intensely to $Fy(a^+b^+)$ cells and poorly to $Fy(a^+b^-)$ cells (see FIG. 8). P. knowlesi-susceptible erythrocytes from Rhesus, Saimiri and Aotus monkeys also bind PkDAP. In addition, however, PkDAP (all of which have at least one Duffy determinant) bound to cells from Cebus monkeys which are not themselves susceptible to P. knowlesi invasion. The Pk135 protein does not bind to erythrocytes from other meals, such as mice or rabbits.

EXAMPLE 7

Purification of Human Duffy Glycoprotein

Figure 10:
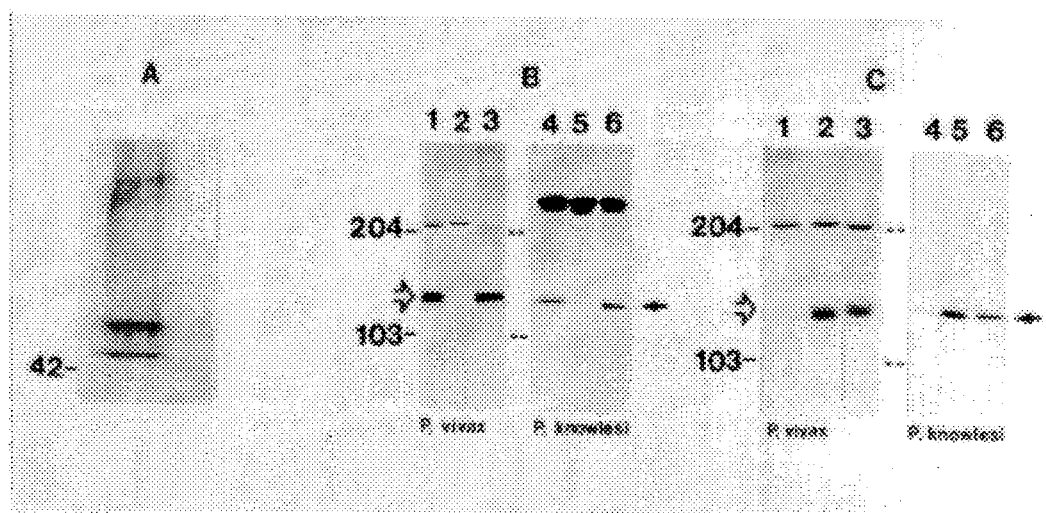
FIG. 10A depicts a gel of silver stained SDS-PAGE affinity-purified human Duffy glycoprotein (seen as the band closest to m.w. marker 42). Duffy glycoprotein aggregates appear as a smear and extra bands in immunoblots with the anti-Fy⁶ monoclonal antibody (mAb).
FIG. 10B is an autoradiograph of an SDS-PAGE gel showing inhibition of protein binding to Duffy-positive human erythrocytes by preincubating purified human Duffy glycoprotein erythrocyte binding assay culture supernatant from an erythrocyte binding assay: inhibition of PvDAP or Pk135 to either human Fy(a⁺b⁺6⁺) or Fy(a⁻b⁺6⁺) erythrocytes (lanes 2 and 5); controls with no protein added to the culture supernatants (lanes 1 and 4) or with addition of an unrelated sialo-glycoprotein, orosomucoid (lanes 3 and 6). PvDAP is indicated by the open arrow and Pk135 is indicated by the closed arrow.
FIG. 10C (also an SDS-PAGE gel autoradiograph) shows inhibition of protein binding to human Fy(a⁺b⁺6⁺) or Fy(a⁻b⁺6⁺) erythrocytes presensitized with the anti-Fy⁶ mAb before doing an erythrocyte binding assay with either P. vivax or P. knowlesi culture supernatants (lanes 1 and 4, respectively). Controls include withholding of the antibody (lanes 2 and 5) or use of an unrelated (anti-glycophorin) mAb (lanes 3 and 6). PvDAP is indicated by the open arrow and Pk135 is indicated by the closed arrow.

Duffy-positive human erythrocyte membrane ghosts (1 unit) were extracted with 1% NP-40. The extract was centrifuged and the supernatant passed over an anti-$Fy^6$ mAb (NYBC-BG6, Nichols, M. E., et al., J. Exp. Med 166:776–785, 1987) affinity column. The column was washed extensively and sequentially with 1% NP-40, 1% NP-40/0.5M NaCl and finally with PBS. Fractions, eluted with 0.2M glycine/3M urea pH 2.5, were collected and assayed for the presence of the Duffy glycoprotein using iodinated anti-$Fy^6$ mAb (Nichols, M. E., et al., J. Exp. Med. 166:776, 1987) in a solid phase radioimmune assay. Positive fractions were dialyzed against PBS at 4° C. and concentrated in an Amicon concentrator to an $OD_{280}$ of 0.5. An aliquot was added to an equal volume of double strength SDS sample buffer without mercaptoethanol and electrophoresed on an 8–25% SDS-PAGE Phast-Gel (Pharmacia-LKB, Piscataway, N.J.). The gel was stained with a silver stain kit (Bio-Rad, Richmond, Calif.) after oxidation with 1% periodic acid and 1% gluteraldehyde. (FIG. 10A)

EXAMPLE 8

Inhibition of the Binding of Duffy-Associating Proteins (DAPs) to Erythrocytes

To determine whether PvDAP and Pk135 were reacting specifically with the Duffy glycoprotein, or with another erythrocyte surface protein, purified human Duffy glycoprotein and the anti-$Fy^6$ mAb were used.

50 ul of purified Duffy glycoprotein or orosomucoid (1 mg/ml, Sigma Chemicals, St. Louis, Miss.) were incubated with 250 ul of parasite culture supernatant for i hour at room temperature. Human $Fy(a^+b^+)$ cells were incubated with anti-$Fy^6$ mAb purified from ascites (10 ug/ml) or with 500 ul of an anti-glycophorin ($En^a$) mAb culture supernatant (mAb 10–22, 20–25 ug/ml of antibody, Perkins, M. E., et al, J. Immunol. 141:3190–3196, 1988). F(ab) fragments of the anti-$Fy^6$ mAb were obtained by treating the affinity purified antibody with cystsine-activated papain conjugated to agarose (Sigma). After digestion, the papain was centrifuged away and the supernatant was passed over a protein A-affigel column (Bio-Rad, Richmond, Calif.) to remove the Fc portion. The purity of the F(ab) preparation was checked by SDS-PAGE and silver stain analysis.

Thus, incubation of purified Duffy glycoprotein (FIG. 10A) with the P. vivax culture supernatant, prior to the addition of erythrocytes has been found to completely inhibit the binding of PvDAP to Duffy-positive human erythrocytes (FIG. 10B, lane 2), while an unrelated human sialo-glycoprotein, orosomucoid, had no inhibitory effect (FIG. 10B, lane 3). The binding of PvDAP to Duffy-positive human erythrocytes may also be specifically inhibited by the anti-$Fy^6$ mAb or its F(ab) fragments (FIG. 10C, lane 1). Anti-$Fy^6$ antisera partially inhibited the binding of PvDAP to $Fy(a^+b^-)$ human erythrocytes while antibodies against a common glycophorin determinant ($En^a$, see, Darnbrough, J., et al., Vox. Sang. 17:241–255, 1969) unrelated to Duffy had no effect on the binding of PvDAP (FIG. 10C, lane 3). The binding of Pk135 to human erythrocytes is also specifically inhibited by both purified Duffy glycoprotein and the anti-$Fy^6$ mAb (FIG. 10B, lane 5 and FIG. 10C, lane 4, respectively).

The foregoing results demonstrate the receptor-like specificity with which DAP binds to Duffy antigens (the latter serving as the ligand in this interaction).

EXAMPLE 9

Effect of Protease Treatment of Erythrocytes on Binding

The importance of Duffy glycoprotein as a ligand in the invasion of human erythrocytes by P. vivax (Barnwell, J. W., et al, J. Exp. Med. (in press) supra) and P. knowlesi (Mason, S. J., et al, supra) has been demonstrated by the inhibition of invasion into erythrocytes treated with specific proteases. In addition, these experiments confirm the specificity of the binding between DAP and Duffy antigens.

$1 \times 10^9$ washed erythrocytes were treated with enzymes at 37° C. as follows: 0.5 ml trypsin (1 mg/ml, Sigma) for 0.5 hr; 0.5 ml chymotrypsin (1 mg/ml, Calbiochem-Behring, LaJolla, Calif.) and 0.5 ml V-8 protease (0.2 mg/ml. Boehringer Mannheim Biochemicals, Indianapolis, Ind.) in PBS, pH 7.2 for 2 hr. Reactions were stopped with 1 mM soybean trypsin inhibitor (Sigma), 0.05 mg chymostatin (Sigma) and 1 mM PMSF (Sigma), respectively. The cells were then washed 3 times with RPMI-1640. The effect of V-8 protease on either the $Fy^b$ or the $Fy^6$ determinant was measured by the inability to agglutinate Fy ($a^-b^+$) erythrocytes with an indirect hemagglutination assay using anti-$Fy^b$ sera or a change in specific counts per minute when iodinated anti-$Fy^6$ mAb was incubated with the cells. The binding of the parasite proteins, PvDAP and Pk135 to protease treated erythrocytes correlates with both the susceptibility of the Duffy glycoprotein to these proteases and the ability of P. vivax and P. knowlesi to invade the protease treated human erythrocytes. Treating Duffy-positive human erythrocytes with trypsin, which has no apparent effect on the antigenic determinant of the Duffy glycoprotein or invasion by P. vivax and P. knowlesi (Barnwell, J. W., et al, J.. Exp. Med. (in press) supra; Mason, S. J., et al, supra; Hadley, T. J., et al., supra and Nichols, M. E., et al., supra), had no effect on the binding of PvDAP (FIG. 11, lane 2) or Pk135 (Haynes, J. D., et al., supra). However, treating the cells with chymotrypsin, which removes the Duffy determinants ($Fy^a$, $Fy^b$ and $Fy^6$) (Hadley, T. J., et al., supra; Nichols, M. E., et al., supra) and prevents invasion (Barnwell, J. W., et al., *J. Exp. Med.* (in press) supra; Mason, S. J., et al., supra), abrogates the binding of PvDAP (FIG. 11, lane 3) and Pk135 (Haynes, J. D., et al, supra).

Figure 11:
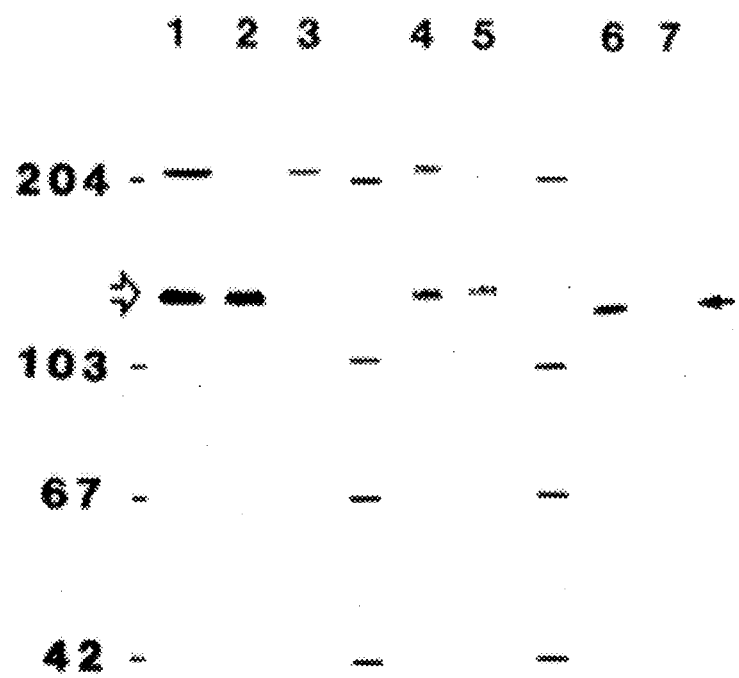
FIG. 11 is an SDS-PAGE autoradiograph showing the effect of protease treatment of erythrocytes on the ability of parasite proteins to bind: P. vivax proteins binding to human Fy(a⁺b⁺6⁺) erythrocytes treated with either no enzymes, trypsin, or chymotrypsin (lanes 1–3); human Fy(a⁻ᵇ⁺6⁺) erythrocytes treated with either no enzyme or V-8 protease (lanes 4 and 5); P. knowlesi proteins binding to human Fy(a⁻b⁺6⁺) erythrocytes treated with no enzymes or with V-8 protease (lanes 6 and 7). PvDAP and Pk135 are indicated by the open and closed arrows, respectively.

The $Fy^b$ determinant on intact human erythrocytes can be removed or disrupted by V-8 protease, however, this protease has no effect on the $Fy^6$ determinant. When human $Fy(a^-b^+)$ erythrocytes were treated with V-8 protease PvDAP still bound to these erythrocytes (FIG. 11, lane 5). However, V-8 protease treatment of human $Fy(a^-b^+)$ erythrocytes prevents the binding of Pk135 (FIG. 10, lane 7) indicating that, unlike PvDAP, PkDAP-Duffy interaction requires the involvement of the $Fy^b$ determinant of the Duffy protein.

EXAMPLE 10

Creating Anti-Pk135 Cross-Reactive Antiserum and Cross-Reactive Monospecific Polyclonal and Monoclonal Mouse Anti-DAP Antibodies To further characterize these parasite proteins and to purify them, a Saimiri monkey antiserum to the 135kD *P. knowlesi* protein was developed. Saimiri monkey Pk135 antiserum was produced by incubating Saimiri erythrocytes ($4\times10^{10}$) and non-radioactive *P. knowlesi* culture supernatant (40 ml). Half of these erythrocytes were then injected intravenously into the Saimiri monkey from which they had been drawn. The other half were eluted in 0.5M NaCl, the eluate was mixed in Freund's incomplete adjuvant and injected intramuscularly. This procedure was repeated three times over a period of five months before a positive response was detected. The thus developed antisera, which include antibodies that recognize PkDAP, could be used to isolate PvDAP by virtue of cross-reactivity with PvDAP.

Indirect immunofluorescence assays with this antiserum on both *P. knowlesi* and *P. vivax* air-dried non-fixed mature schizonts and free merozoites revealed specific fluorescence at the very apical end of the merozoites.

Figure 12:
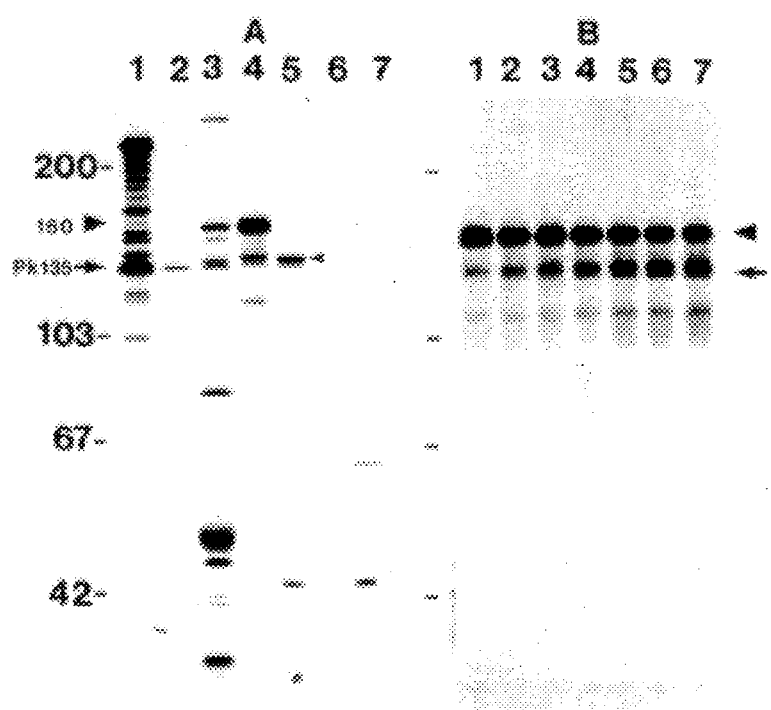
FIG. 12A represents the SDS-PAGE analysis of the Saimiri monkey antiserum: P. knowlesi proteins binding to Rhesus monkey erythrocytes (lane 1); P. knowlesi proteins eluted from Rhesus erythrocytes and immunoprecipitated with the Saimiri antiserum (lane 2); proteins immunoprecipitated from a P. knowlesi culture supernatant or a detergent extract (lanes 3 and 4); immunoprecipitation of a 135 to 140kD protein from a P. vivax detergent extract (lane 5). Pre-immune Saimiri serum used to immunoprecipitate proteins from detergent extracts of either P. knowlesi or P. vivax as controls (lanes 6 and 7, respectively).
FIG. 12B is an SDS-PAGE gel autoradiograph showing the results of immunoprecipitation using the Saimiri monkey antiserum of proteins from a P. knowlesi detergent extract incubated at 37° C. without protease inhibitors for 0, 2, 5, 10, 20, 40 and 60 minutes (lanes 1–7). The 160 kD protein and the 135 kD P. knowlesi proteins are indicates by the arrow head and the closed arrow, respectively.

To further define and characterize the specific 135 kD *P. vivax* and *P. knowlesi* DAPs, mice were immunized with purified native DAPs. DAP was purified by incubating human $Fya^-b^+$ erythrocytes ($5\times10^{10}$) with either *P. knowlesi* or *P. vivax* culture supernatants (50 ml). After passage of the erythrocytes twice through silicone oil, the bound proteins were eluted with 0.5M NaCl. The eluate was then mixed with SDS sample buffer and subjected to SDS-PAGE (7.5% polyacrylamide). The separated proteins were then electroblotted onto nitrocellulose sheet. Radioactive-labeled ($^{35}$S-methionine) eluted proteins were run in the end lanes to mark the exact position of DAP on the nitrocellulose which was revealed by autoradiography. A thin strip (2–3 mm) of the (unlabelled) nitrocellulose (from an otherwise identical procedure) was cut out at the position of the blotted and radioactively-labeled DAP proteins. Portions of the nitrocellulose strip were then implanted into the spleens and peritoneal cavities of mice. This procedure was repeated three times with the same mice to generate an antibody response. The antibodies react exclusively at the very apical end of both *P. vivax* and *P. knowlesi* merozoites. As described for the Saimiri anti-Pk 135 antisera (FIG. 12A), antibodies recognized 135 and 155 kD proteins by immunoprecipitation. Hybridomas secreting anti-DAP monoclonals are produced by established methods (Kohler and Milstein, C., *Nature*, 256:495–497, 1975). Essentially, spleen cells from mice immunized with the purified DAP are fused with FOX-NY (Hyclone, Ogden, Utah) myeloma cells, cultured, and cloned by limiting dilution. Culture supernatants are screened for positive clones secreting the appropriate antibodies by indirect immunofluorescence on air-dried *P. vivax* and *P. knowlesi* merozoites and immunoprecipitation of $^{35}$S-methionine labeled culture supernatants and detergent extracts of merozoites.

EXAMPLE 11

Extraction and Immunoprecipitation of Parasite Proteins

Biosynthetically labeled (with $^{35}$S-methionine, see Example 1) late schizont parasitized erythrocytes were washed 3 times with PBS. The cells were extracted in 1% Triton X-100 at 4° C. with the protease inhibitors (50 ug/ml) chymostatin and leupeptin (Sigma) added. The cells were extracted for 0.5 hr with agitation. After the extraction the solution was centrifuged to remove any particulate material. Parasites for the proteolytic degradation experiment were extracted in a similar manner without the addition of protease inhibitors. These extracts were used the day they were made.

Antisera from Example 5 were incubated with labeled parasite proteins, either culture supernatant or detergent extract, for 2 hours at 4° C. with rocking. Material eluted from an erythrocyte binding assay was diluted with an equal volume of PBS before the antisera were added. Antigen-antibody complexes were precipitated by adding Protein A Sepharose (Pharmacia) and incubating an additional 2 hours. The Sepharose was washed by centrifugation with Tris buffered saline containing 0.5% Triton X-100 and 5 mM EDTA (NETT) and NETT with 0.5M NaCl. The complexes were dissociated by the addition of an equal volume of double-strength SDS sample buffer containing mercaptoethanol, boiled and applied to a 7.5% SDS-PAGE.

Thus, when the Saimiri antiserum was used to precipitate proteins from either a *P. knowlesi* culture supernatant or a *P. knowlesi* schizont detergent extract, a major band of X60 kD, not 135 kD, was precipitated (FIG. 12A, lanes 3 and 4). However, this antiserum precipitated only the 135 kD protein from *P. knowlesi* culture supernatant proteins eluted from human $Fy(a^-b^+)$ or Rhesus erythrocytes (FIG. 12A, lane 2). When this antiserum was used to precipitate proteins from *P. vivax* detergent extracts a 135 to 140 kD protein was detected (FIG. 12A, lane 5) along with a minor band at 160 kD on some occasions.

It is thus possible that the *P. knowlesi* 135 kD protein is a proteolytic product of the 160 kD protein immunoprecipitated by the antiserum. To address this possible relationship an immunoprecipitation was performed with the anti-Pk135 antiserum and *P. knowlesi* schizonts which had been extracted in the absence of protease inhibitors. (FIG. 12B). Equal aliquots of this inhibitor-free extract were incubated at 37° C. for various times ranging from 0 to 60 minutes. Any proteolysis was stopped by the addition of protease inhibitors leupeptin and chymostatin and by placing the aliquots at 4° C. The anti-Pk135 antiserum was then used to precipitate proteins from these samples. At time 0 minutes (FIG. 12B, lane 1) there is a strong signal at 160 kD with minor bands at 135 and 120 kD. As the incubation continues, the intensity of the 160 kD band decreases with a corresponding increase in the intensity of the 135 kD band. The 120 kD band also increases in intensity and there is the appearance of bands at 95, 84 and 51 kD at the later time points. These bands most likely represent further proteolytic degradation of the 160 kD protein and have been noted in eluates of *P. knowlesi* proteins bound to Rhesus erythrocytes.

EXAMPLE 12

Inhibition of *P. knowlesi* Merozoite Invasion of Human Duffy Positive Erythrocytes by anti-Pk 135 Antiserum The antisera from Example 5 were used in an in-vitro invasion assay to determine the effect of such sera on merozoite invasion of human erythrocytes. *P. falciparum* late trophozoite- and early schizont-infected erythrocytes were concentrated to 80% parasitemia on plasmagel and adjusted to $10^8$/ml in medium. Target cells at $10^8$/ml were mixed with parasitized erythrocytes at a ratio of 10:1 and cultured in 0.5 ml volumes in 24-well tissue culture plates. *P. knowlesi* schizont-infected erythrocytes were concentrated to >95% parasitemia on a 54% Percoll cushion (Barnwell, J. W., et al, *Infect. Immun.* 40:985, 1983), adjusted to $5\times10^7$/ml, mixed with target cells ($5\times10^7$/ml) at a 1:10 ratio, and cultured in 0.5 ml medium volumes in 24-well tissue culture plates. *P. vivax* schizont-infected erythrocytes were mixed with target cells at 1:5 to 1:10 ratios at $5\times10^7$/ml and cultured as above. Antisera or control sera were incorporated into the tissue culture medium at a concentration of 10% volume/volume. Uninfected erythrocytes for use in *P. vivax* invasion assays were first processed on 62% Percoll cushions to increase the percentage of reticulocytes. The less dense erythrocytes at the Percoll interface were used as target cells in assays of invasion. *P. falciparum* cultures were harvested after 12 hours for blood film preparation. *P. knowlesi* and *P. vivax* cultures were harvested after 8–10 hours. After Giemsa staining of thin film smears, 1,000–2,000 erythrocytes were examined by light microscopy and the number of ring stage parasites was determined. Smears of the infected erythrocytes/target cell mixtures were also made at the start of the invasion assays and the number of ring stage parasites were determined. Any background invasion rates found in these wells were subtracted from the invasion rates determined in the test wells after 8–10 hours of incubation. The Pk 135 antiserum inhibited *P. knowlesi* merozoite invasion of human Duffy positive erythrocytes 40 to 60% in comparison to invasion in the presence of normal squirrel monkey serum. *P. falciparum* merozoite invasion was not affected by the anti-Pk 135 serum. *P. vivax* invasion was not significantly inhibited in comparison to control serum.

EXAMPLE 13

No Specificity for Duffy Glycoproteins by Other Malarial Proteins

The erythrocyte binding assay of Example 1 was used to determine whether other merozoite antigens recognize the Duffy blood group glycoprotein. The results are summarized in Table 1. A *P. vivax* protein of 205 kD bound to all human erythrocytes, regardless of their Duffy phenotype, and also to Aotus and Saimiri erythrocytes (FIG. 8). Similarly, a 220–230 kD *P. knowlesi* protein binds to Rhesus erythrocytes (FIG. 9) and on occasion to human erythrocytes. The erythrocyte proteins recognized by these parasite proteins or their role in the invasion process are not known. These proteins probably are not involved in the initial recognition and attachment of the merozoite to the host erythrocyte as their binding is prevented by trypsin treatment of erythrocytes which does not inhibit invasion.

A *P. knowlesi* protein of 155 kD that binds to Rhesus, Saimiri and Aotus monkey erythrocytes is also apparent in *P. knowlesi* culture supernatants (FIG. 9). Treating Rhesus or Saimiri erythrocytes with trypsin has no effect on the binding of this protein while, chymotrypsin treatment of these cells prevents binding (data not shown). This protein may be an unrelated erythrocyte-binding protein as has been suggested by adsorption studies (Miller, L. H., et al., *Molec. Biochem. Parasitol.* 31:217–222, 1988). Alternatively, it may be a proteolytic fragment related to Pk135. If the *P. knowlesi* Duffy-associating protein binds to erythrocytes as the 160 kD protein and then undergoes proteolytic degradation to the 135 kD protein, then the appearance of the 155 kD protein on some simian erythrocytes could reflect incomplete degradation that does not occur on human or Cebus erythrocytes.

EXAMPLE 14

Screening of *P. vivax* Genomic DNA Libraries

Lambda ZAP® (Stratagene, LaJolla, Calif.) genomic DNA expression libraries were constructed essentially as described for cDNA expression libraries in *DNA Cloning—A Practical Approach*, Glover, D. M., Editor, IRL Press, 1986, Vol. 1, Chapter 2, Huynh, T. V., Young, R. A., and Davis, R. W. (lambda gt 11 can be purchased from Stratagene, LaJolla, Calif.) or in Young, R. A., et al., *Proc. Nat'l. Acad. Sci.* 80:1194, 1983; and Young, R. A., et al., *Proc. Nat'l. Acad. Sci.* 82:2583, 1985. In brief, genomic DNA was sheared to obtain fragments averaging 2–7 kb in size or restricted with mung bean nuclease in 42.5% formamide. EcoR1 linkers (Biolabs) were added and the resulting fragments were ligated into the EcoR1 site of lambda rAP®. Recombinant DNA was packaged using commercial phage packaging extracts from Strategene with the accompanying manufacturer's protocols, and they were plated on XL1 BLUE cells (Stratagene) for immunoscreening. However, another mode of construction of a genomic DNA library could have been used with optional suitable modification of the subsequent expression strategy. Other variations or methods for constructing genomic libraries can be gleaned, e.g., from U.S. Pat. Nos. 4,693,994 or 4,707,357, but such methods are well-known.

The 1.8 Kb DNA inserts of the Pk DAP gene and the *P. knowlesi* Pk 135 antisera from Example 5 were used to screen the genomic libraries, which were expressed in Y1090 cells. Positive clones have been identified and confirmed by 3 rounds of plaque purification. These are being sequenced as follows (by way of nonlimiting example):

Phage will be prepared from these clones essentially as described for the production of lambda gt11 phage in DNA *Cloning* 1: *A Practical Approach,* Glover, D. M., Editor, IRL Press, 1986, Vol. 1, Chapter 2, Huynh, T. V., Young, R. A., and Davis, R. W. using protocols from the manufacturer (Strategene), and the phage and their DNAs were purified using LAMBDASORB™ phage adsorbent and accompanying protocols from Promega.

Phage DNA inserts can then be released by restricting the DNA with EcoR1 or KpnI and SacI, and cloned into and sequenced from the commercially available plasmid BLUESCRIPT™ (Stratagene) or pGEM® (Promega). XL1-Blue cells (obtained from Stratagene) will be transformed using the well-known procedures of Hanahan, D., 1983, *J. Mol. Biol.,* 166:557–580, and large preparations of plasmid DNA will be obtained using the standard alkaline lysis protocol and CsCl gradient purification (Maniatis, T., *Molecular Cloning,* A Laboratory Manual, p. 90–93, Cold Spring Harbor Laboratories, New York 1982). Clones comprising a set of nested deletions will be prepared using standard exonuclease III/mung bean nuclease digestion methodology in accordance with protocols supplied with Stratagene's endonuclease III/mung bean nuclease deletion kit. Subsequently generated clones will be sequenced using the technique of Sanger, F., et al., *Proc. Nat'l Acad. Sci.* 74:5463–5467, 1977, reagents supplied in U.S. Biochemical Corps. SEQUENASE™ sequencing kit and protocols modified to optimize sequencing reactions performed in double stranded DNA using the enzyme SEQUENASE™. Sequence information will be analyzed using IBI's Pustell DNA sequence analysis programs and Ganbank for comparative studies.

The protein expressed as a beta-galactosidase or other appropriate fusion protein can be purified and used to raise antisera in rabbits and/or mice. These antisera can be used to immunoprecipitate, or can otherwise be used to show specific reactivity with the native DAP antigen from P. vivax or P. knowlesi. Positive results will thus confirm that the appropriate DNA has been cloned and the appropriate product has been expressed. (Alternatively, polyclonal or preferably monoclonal antibodies to natural purified DAP can be raised (Example 10) and used to confirm the nature of the expressed protein).

Assuming that the parasite DNA inserts will contain only a fragment of the nucleic acid sequence of the DAP gene, elucidation of the remainder of the nucleic acid sequence of the entire PvDAP gene is well within the skill of the art.

For example, the entire recovered DNA insert can be used for screening a nonexpression genomic P. vivax library (e.g. in an appropriate lambda replacement vector available from Stratagens, LaJolla, Calif.) to identify the entire gene for P. vivax native DAP. Once identified, the entire gene can be extracted from the genomic DNA library, purified, sequenced and duplicated in accordance with known techniques.

In this manner, the entire DNA sequence for the native DAP can be elucidated and the corresponding amino acid sequence can be determined. Construction of fragments, derivatives or analogs and hybrid constructs (i.e. comprising moieties or sequences of non-malarial origin) can then proceed as discussed above.

EXAMPLE 15

Screening of cDNA Expression Libraries of *P. knowlesi*

A lambda gt11/*P. vivax* genomic DNA expression library was constructed from mRNA obtained from *P. knowlesi* mature schizonts essentially as described for cDNA expression libraries in *DNA Cloning—A Practical Approach*, Glover, D. M., Editor, IRL Press, 1986, Vol. 1, Chapter 2, Huynh, T. V., Young, R. A., and Davis, R. W. (lambda gt 11 can be purchased from Stratagens, LaJolla, Calif.) or in Young, R. A., et al., *Proc. Nat'l. Acad. Sci.* 80:1194, 1983; and Young, R. A., et al., *Proc. Nat'l. Acad. Sci.* 82:2583, 1985. In brief, poly-A tailed mRNA was reverse-transcribed and double-stranded cDNA was synthesized. EcoR1 linkers (Biolabs) were added and the resulting fragments were ligated into the EcoR1 site of lambda gt11 (purchased from Promega). Recombinant DNA was packaged using commercial phage packaging extracts from Promega with the accompanying manufacturer's protocols, and they were plated on Y1090 cells (Promega) for immunoscreening. However, another mode of construction of a DNA library could have been used with optional suitable modification of the subsequent expression strategy.

Also lysogens of recombinant phage were prepared using Y1090 cells (from which large preparations of phage and their DNAs were made) and Y1089 cells for the production of large quantities of beta-galactosidase fusion proteins. Fusion proteins were prepared from the Y1089 lysogens essentially as described in protocols available from Promega. Lysogens were prepared by first producing a large plaque of each recombinant on bacterial lawns of Y1090 and 1089 and then streaking cells from the center of each large plaque. Colonies which grew were tested for lysogeny by their ability to grow at 32° and 42° C.

*P. knowlesi* Pk 135 antisera from Example 5 were used to screen the cDNA library, which was expressed in Y1090 cells. A positive clone was identified and confirmed by 3 rounds of plaque purification. This clone was sequenced as follows (by way of nonlimiting example):

Phage were prepared from these clones essentially as described for the production of lambda gt11 phage in *DNA Cloning* 1: *A practical Approach*, Glover, D. M., Editor, IRL Press, 1986, Vol. 1, Chapter 2, Huynh, T. V., Young, R. A., and Davis, R. W., and the phage and their DNAs were purified using LAMBDASORB™ phage adsorbent and accompanying protocols from Promega.

The phage DNA insert was then released by restricting the DNA with EcoR1 or KpnI and SacI, and cloned into and sequenced from the commercially available plasmid BLUESCRIPT™ (Stratagene). XL1-Blue cells (obtained from Stratagene) were transformed using the well-known procedures of Hanahan, D., 1983, *J. Mol. Biol.*, 166:557–580, and large preparations of plasmid DNA were obtained using the standard alkaline lysis protocol and CsCl gradient purification (Maniatis, T., *Molecular Cloning, A Laboratory Manual*, p. 90–93, Cold Spring Harbor Laboratories, New York 1982). Clones comprising a set of nested deletions were prepared using standard exonuclease III/mung bean nuclease digestion methodology in accordance with protocols supplied with Stratagene's exonuclease III/mung bean nuclease deletion kit. Subsequently, generated clones were sequenced using the technique of Sanger, F., et al., *Proc. Nat'l. Acad. Sci.* 74:5463–5467, 1977, reagents supplied in U.S. Biochemical Corps. SEQUENASE™ sequencing kit and protocols modified to optimize sequencing reactions performed in double stranded DNA using the enzyme SEQUENASE™. Sequence information was analyzed using IBI's Pustell DNA sequence analysis programs and Ganbank for comparative studies. The nucleic and deduced amino acid sequences of the cloned 1.8 kD insert is depicted in FIG. 13A through 13H.

The lambda gt 11 phage beta-galactosidase fusion protein was purified by affinity chromatography on a rabbit anti-beta galactosidase-Sepharose 4B column and used to raise antisera in mice. The resulting antisera reacted exclusively with the apical end of *P. knowlesi* and *P. vivax* air-dried merozoites by indirect immunofluorescence and immunoprecipitated a 135 kD band from detergent extracts of *P. vivax* and *P. knowlesi* mature schizonts and merozoites radio-labeled biosynthetically with $^{35}$S-methionine (data not shown). These positive results confirm that the appropriate DNA for the PkDAP gene has been cloned and expressed. Monoclonal antibodies to natural purified Pk DAP are being raised and can be used to confirm the nature of the expressed protein.

Assuming that the parasite inserts will contain only a fragment of the nucleic acid sequence of the Pk DAP gene, elucidation of the remainder of the nucleic acid sequence of the entire PkDAP gene is well within the skill of the art.

For example, the entire recovered DNA insert can be used for screening a nonexpression genomic *P. knowlesi* library (e.g. in an appropriate lambda replacement vector available from Stratagens, LaJolla, Calif.) to identify the entire gene for *P. knowlesi* native DAP. Once identified, the entire gene can be extracted from the genomic DNA library, purified, sequenced and duplicated in accordance with known techniques.

In this manner, the entire DNA sequence for the native *P. knowlesi* DAP can be elucidated and the corresponding amino acid sequence can be determined. Construction of fragments, derivatives or analogs and hybrid constructs (i.e. comprising moieties or sequences of non-malarial origin) can then proceed as discussed above.

The present invention is not limited to the embodiments specifically described above. As those skilled in the art will appreciate, many modifications are possible, all within the scope of the present invention as claimed below.

TABLE 1

Correlation of erythrocyte binding proteins with Duffy phenotype and susceptibility of erythrocyte to invasion.

| Species (Common Name) | Duffy Phenotype[a] | | | | Binds | | Invasion[c] by P. vivax | Invasion[d] by P. knowlesi | P. knowlesi[e] Merozoite Attachment | Other Erythrocyte Binding Proteins | |
|---|---|---|---|---|---|---|---|---|---|---|---|
| | Fy[a] | Fy[b] | Fy[3] | Fy[6] | PvDAP | Pk135[b] | | | | P. vivax | P. knowlesi |
| *Homo sapiens* (men) | + | + | + | + | + | + | + | + | + | 205 | 220–230 |
| | + | 0 | + | + | + | + | + | + | + | 205 | 220–230 |
| | 0 | + | + | + | + | + | + | + | + | 205 | 220–230 |
| | 0 | 0 | 0 | 0 | 0 | 0 | 0 | 0 | + | 205 | 220–230 |
| *Aotus triviratus* (owl monkey) | 0 | + | + | + | + | + | + | + | + | 205 | 220–230, 155 |
| *Saimiri sciureus* (squirrel monkey) | 0 | 0 | + | + | 0 | + | + | + | + | 205 | 220–230, 155 |
| *Macaca mulatta* (rhesus monkey) | 0 | + | + | 0 | 0 | + | 0 | + | + (weak) | 205 | 220–230, 155–120 |
| *Cebus apella* (Capuchin monkey) | 0 | 0 | + | 0 | 0 | + | 0 | 0 | 0 | 0 | 0 |

[a]Marsh, 1975, supra; Nichols, et al., 1987, supra; and Palatnik, M., et at., J. Hum. Evol., 13:173, 1984.
[b]Pk135 binds to Fy (a⁻b⁺) >> Fy (a⁺b⁺) > Fy (a⁺b⁻) human erythrocytes.
[c]Miller, 1976, supra; Young, M. D., et al., Science 153:1006, 1966; and Coatny, G. R., et al., 1971, The Primate Malarias, U.S. Department of Health & Education, 330.
[d]Miller, 1975, supra.
[e]Miller, 1979, supra; and Miller, et al., Am. Trop. Med. Hyg. 26:204, 1977.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 3763 base pairs
        ( B ) TYPE: Nucleic acid
        ( C ) STRANDEDNESS: double
        ( D ) TOPOLOGY: linear ( i i ) MOLECULE TYPE: Genomic DNA
        ( A ) DESCRIPTION:

( i i i ) HYPOTHETICAL: No ( i v ) ANTI-SENSE: No ( v ) FRAGMENT TYPE:

( v i ) ORIGINAL SOURCE:
        ( A ) ORGANISM: P.vivax
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY: Lambda gt 11 native P.vivax DNA expression library
        ( B ) CLONE: 5.3

( v i i i ) POSITION IN GENOME:
        ( A ) CHROMOSOME/SEGMENT:
        ( B ) MAP POSITION:
        ( C ) UNITS:

( i x ) FEATURE:
    ( A ) NAME/KEY:
    ( B ) LOCATION:
    ( C ) IDENTIFICATION METHOD:
    ( D ) OTHER INFORMATION: This sequence corresponds to Figure 1A (sheets 1-4) in the application, as filed.

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:1:

```
TTC  GAT  AAA  GAA  AAA  GTT  AAA  GAT  ACA  AGT  TTT  GAT  GAA  AAA  AAG  AAA      48
Phe  Asp  Lys  Glu  Lys  Val  Lys  Asp  Thr  Ser  Phe  Asp  Glu  Lys  Lys  Lys
 1              5                        10                       15

AGC  ATA  GAA  AAA  GCT  TAT  GAA  AAA  ATG  GGA  AAT  ACG  CTT  AAA  GAA  TTA      96
Ser  Ile  Glu  Lys  Ala  Tyr  Glu  Lys  Met  Gly  Asn  Thr  Leu  Lys  Glu  Leu
                20                       25                       30

GAA  AAA  ATG  GAT  GAC  GAA  AAA  AAC  ATA  GAA  AAA  GAA  GTA  GAA  GAA  GCT     144
Glu  Lys  Met  Asp  Asp  Glu  Lys  Asn  Ile  Glu  Lys  Glu  Val  Glu  Glu  Ala
           35                        40                       45

CAA  ATA  CAA  TAC  AAA  AGA  ATT  TTT  ATT  GAT  CAT  GAT  GTT  AAT  TTG  ATG     192
Gln  Ile  Gln  Tyr  Lys  Arg  Ile  Phe  Ile  Asp  His  Asp  Val  Asn  Leu  Met
     50                       55                       60

AAT  GAT  GAA  GTT  GAA  AAG  TCC  AAA  ATT  GTG  ATG  GAA  AAA  ATC  GAA  TTA     240
Asn  Asp  Glu  Val  Glu  Lys  Ser  Lys  Ile  Val  Met  Glu  Lys  Ile  Glu  Leu
65                       70                       75                       80

TAT  AAA  AAA  GAA  ATT  GAC  GAA  ATT  AAA  CAG  AAA  ACG  AAT  GAG  TAT  AAG     288
Tyr  Lys  Lys  Glu  Ile  Asp  Glu  Ile  Lys  Gln  Lys  Thr  Asn  Glu  Tyr  Lys
                     85                       90                       95

CAA  GGT  GAT  ACA  TCT  AAT  TTT  TAT  TAT  ACA  GAA  CAA  TAC  AAC  AGT  GCT     336
Gln  Gly  Asp  Thr  Ser  Asn  Phe  Tyr  Tyr  Thr  Glu  Gln  Tyr  Asn  Ser  Ala
               100                      105                      110

ACA  CAG  AGT  AAA  GCT  AAA  ATA  GAA  CAA  TTT  ATT  AAT  ATT  GCT  ACG  ACA     384
Thr  Gln  Ser  Lys  Ala  Lys  Ile  Glu  Gln  Phe  Ile  Asn  Ile  Ala  Thr  Thr
          115                      120                      125

AAA  AAA  GGA  ACG  TCT  GAC  ACA  AGC  CAA  GAT  ATA  AAC  GAA  TTA  GAA  AGC     432
Lys  Lys  Gly  Thr  Ser  Asp  Thr  Ser  Gln  Asp  Ile  Asn  Glu  Leu  Glu  Ser
          130                      135                      140

ATT  AAA  GAA  GAG  GTG  CAT  AAA  AAT  TTA  CAA  CTA  GTC  AAA  CAA  GAA  AGT     480
Ile  Lys  Glu  Glu  Val  His  Lys  Asn  Leu  Gln  Leu  Val  Lys  Gln  Glu  Ser
145                      150                      155                      160

AAT  TCT  ATG  GAG  GAA  ATG  CGA  AAA  CAA  ATT  CTA  AGC  ATG  AAG  GAT  TTG     528
Asn  Ser  Met  Glu  Glu  Met  Arg  Lys  Gln  Ile  Leu  Ser  Met  Lys  Asp  Leu
                    165                      170                      175

CTA  ATT  TTG  AAC  AAT  TCC  GAA  ACT  ATA  GCT  AAA  GAA  ATA  TCA  AAT  AAT     576
Leu  Ile  Leu  Asn  Asn  Ser  Glu  Thr  Ile  Ala  Lys  Glu  Ile  Ser  Asn  Asn
               180                      185                      190

ACT  CAA  AAC  GCA  TTA  GGT  TTT  AGG  GAG  AAT  GCA  AAA  ACA  AAA  CTT  AAT     624
Thr  Gln  Asn  Ala  Leu  Gly  Phe  Arg  Glu  Asn  Ala  Lys  Thr  Lys  Leu  Asn
          195                      200                      205

AAA  ACA  GAT  GAA  CTA  TTG  CAA  AGA  GTG  GCA  GCT  ATG  ATA  GAA  GAG  GCA     672
Lys  Thr  Asp  Glu  Leu  Leu  Gln  Arg  Val  Ala  Ala  Met  Ile  Glu  Glu  Ala
210                      215                      220
```

| | | | | | | | | | | | | | | | | |
|---|---|---|---|---|---|---|---|---|---|---|---|---|---|---|---|---|
| AAG | GCA | CAT | AAG | AAC | AAT | ATT | GAC | ATA | GCT | TTA | GAA | GAT | GCA | CAA | ATA | 720 |
| Lys | Ala | His | Lys | Asn | Asn | Ile | Asp | Ile | Ala | Leu | Glu | Asp | Ala | Gln | Ile | |
| 225 | | | | 230 | | | | 235 | | | | | 240 | | | |
| GAT | ACG | GAG | GTA | AGC | AAA | ATT | GAA | CAA | ATT | AAT | CGT | GAA | ATT | ATG | AAT | 768 |
| Asp | Thr | Glu | Val | Ser | Lys | Ile | Glu | Gln | Ile | Asn | Arg | Glu | Ile | Met | Asn | |
| | | | | 245 | | | | 250 | | | | | 255 | | | |
| AAA | AAA | GAT | GAA | ATT | AAA | TCC | TAT | TTA | AGT | GAA | ATA | AAA | GAA | TAT | AAA | 816 |
| Lys | Lys | Asp | Glu | Ile | Lys | Ser | Tyr | Leu | Ser | Glu | Ile | Lys | Glu | Tyr | Lys | |
| | | | 260 | | | | 265 | | | | 270 | | | | | |
| GAC | AAA | TGC | ACA | ACC | GAA | ATC | AGT | AAT | TCA | AAA | AGA | GGA | AAA | GAT | AAA | 864 |
| Asp | Lys | Cys | Thr | Thr | Glu | Ile | Ser | Asn | Ser | Lys | Arg | Gly | Lys | Asp | Lys | |
| | | 275 | | | | 280 | | | | | 285 | | | | | |
| ATT | GAG | TTC | TTG | GAA | AAA | TTT | AAG | CCT | AAT | GAG | GAA | AGC | AAT | TCG | AAT | 912 |
| Ile | Glu | Phe | Leu | Glu | Lys | Phe | Lys | Pro | Asn | Glu | Glu | Ser | Asn | Ser | Asn | |
| 290 | | | | 295 | | | | | 300 | | | | | | | |
| AAG | GTT | AAC | ATT | AAT | GAA | ATA | AAT | GAA | AAT | ATA | AGA | AAT | TCT | GAA | CAA | 960 |
| Lys | Val | Asn | Ile | Asn | Glu | Ile | Asn | Glu | Asn | Ile | Arg | Asn | Ser | Glu | Gln | |
| 305 | | | | | 310 | | | | 315 | | | | | 320 | | |
| TAC | TTA | AAA | GAT | ATA | GAA | GAC | GCA | GAA | AAA | CAA | GCT | AGT | ACA | AAA | GTA | 1008 |
| Tyr | Leu | Lys | Asp | Ile | Glu | Asp | Ala | Glu | Lys | Gln | Ala | Ser | Thr | Lys | Val | |
| | | | | 325 | | | | 330 | | | | | 335 | | | |
| GAA | CTA | TTC | CAT | AAA | CAT | GAA | ACA | ACT | ATC | AGT | AAT | ATT | TTC | AAG | GAA | 1056 |
| Glu | Leu | Phe | His | Lys | His | Glu | Thr | Thr | Ile | Ser | Asn | Ile | Phe | Lys | Glu | |
| | | | 340 | | | | | 345 | | | | 350 | | | | |
| TCT | GAA | ATT | TTA | GGA | GTG | GAA | ACT | AAA | TCC | CAA | AAA | AAA | ATT | AAT | AAA | 1104 |
| Ser | Glu | Ile | Leu | Gly | Val | Glu | Thr | Lys | Ser | Gln | Lys | Lys | Ile | Asn | Lys | |
| | | 355 | | | | | 360 | | | | | 365 | | | | |
| GCA | GAA | GAC | ATA | ATG | AAA | GAA | ATT | GAG | CGT | CAC | AAT | TCT | GAA | ATT | CAA | 1152 |
| Ala | Glu | Asp | Ile | Met | Lys | Glu | Ile | Glu | Arg | His | Asn | Ser | Glu | Ile | Gln | |
| | 370 | | | | | 375 | | | | | 380 | | | | | |
| ACA | CAG | GTG | AAA | GGT | TTC | CAA | GAA | AAT | CTA | AAT | AAA | CTG | AAC | GAG | CCC | 1200 |
| Thr | Gln | Val | Lys | Gly | Phe | Gln | Glu | Asn | Leu | Asn | Lys | Leu | Asn | Glu | Pro | |
| 385 | | | | | 390 | | | | | 395 | | | | | 400 | |
| CAT | AAT | TAT | GAC | AAC | GCA | GAA | GAT | GAA | CTT | AAT | AAT | GAT | AAA | TCT | ACG | 1248 |
| His | Asn | Tyr | Asp | Asn | Ala | Glu | Asp | Glu | Leu | Asn | Asn | Asp | Lys | Ser | Thr | |
| | | | | 405 | | | | 410 | | | | | 415 | | | |
| AAT | GCA | AAG | GTA | CTT | ATA | GAA | ACT | AAC | CTA | GAA | AGT | GTA | AAA | CAT | AAT | 1296 |
| Asn | Ala | Lys | Val | Leu | Ile | Glu | Thr | Asn | Leu | Glu | Ser | Val | Lys | His | Asn | |
| | | | 420 | | | | | 425 | | | | | 430 | | | |
| TTA | TCA | GAA | ATT | ACT | AAT | ATT | AAA | CAG | GGA | GGA | GAA | AAA | ATA | TAC | AGT | 1344 |
| Leu | Ser | Glu | Ile | Thr | Asn | Ile | Lys | Gln | Gly | Gly | Glu | Lys | Ile | Tyr | Ser | |
| | | | 435 | | | | | 440 | | | | | 445 | | | |
| AAA | GCT | AAA | GAT | ATC | ATG | CAA | AAA | ATA | AAA | GCA | ACT | TCA | GAA | AAT | ACT | 1392 |
| Lys | Ala | Lys | Asp | Ile | Met | Gln | Lys | Ile | Lys | Ala | Thr | Ser | Glu | Asn | Thr | |
| 450 | | | | | 455 | | | | | 460 | | | | | | |
| GCA | GAG | AAA | ACT | TTA | GAG | AAG | GTG | AAA | GAC | GAC | CAA | TCT | AAT | TAT | GTT | 1440 |
| Ala | Glu | Lys | Thr | Leu | Glu | Lys | Val | Lys | Asp | Asp | Gln | Ser | Asn | Tyr | Val | |
| 465 | | | | | 470 | | | | | 475 | | | | | 480 | |
| AAT | TAT | TTA | AAT | CAA | ATA | ACC | ACA | GAA | AGA | AAT | CTT | ATC | GTT | ACG | GAA | 1488 |
| Asn | Tyr | Leu | Asn | Gln | Ile | Thr | Thr | Glu | Arg | Asn | Leu | Ile | Val | Thr | Glu | |
| | | | | 485 | | | | 490 | | | | | 495 | | | |
| AAA | AAT | AGA | CTA | AAT | GGT | ATA | GAT | TCC | ACT | ATT | ACA | AAT | ATA | GAA | GGG | 1536 |
| Lys | Asn | Arg | Leu | Asn | Gly | Ile | Asp | Ser | Thr | Ile | Thr | Asn | Ile | Glu | Gly | |
| | | | 500 | | | | | 505 | | | | | 510 | | | |
| GCA | CTT | AAA | GAA | TCC | AAG | GGA | AAT | TAT | GAA | ATT | GGA | TTT | TTG | GAA | AAG | 1584 |
| Ala | Leu | Lys | Glu | Ser | Lys | Gly | Asn | Tyr | Glu | Ile | Gly | Phe | Leu | Glu | Lys | |
| | | 515 | | | | | 520 | | | | | 525 | | | | |
| TTA | GAA | GAA | ATA | GGT | AAA | AAT | AGA | AAA | TTA | AAG | GTT | GAC | ATA | ACC | AAA | 1632 |
| Leu | Glu | Glu | Ile | Gly | Lys | Asn | Arg | Lys | Leu | Lys | Val | Asp | Ile | Thr | Lys | |
| | | | | 530 | | | | | 535 | | | | | 540 | | |

| | | | | | | | | | | | | | | | | |
|---|---|---|---|---|---|---|---|---|---|---|---|---|---|---|---|---|
| AAA | TCA | ATA | AAT | TCA | ACA | GTG | GGA | AAC | TTT | TCT | TCC | CTC | TTC | AAC | AAT | 1680 |
| Lys | Ser | Ile | Asn | Ser | Thr | Val | Gly | Asn | Phe | Ser | Ser | Leu | Phe | Asn | Asn | |
| 545 | | | | 550 | | | | | 555 | | | | | | 600 | |
| TTT | GAT | TTA | AAT | CAA | TAT | GAC | TTT | AAT | AAA | AAT | ATA | AAT | GAT | TAT | GAA | 1728 |
| Phe | Asp | Leu | Asn | Gln | Tyr | Asp | Phe | Asn | Lys | Asn | Ile | Asn | Asp | Tyr | Glu | |
| | | | | 605 | | | | | 610 | | | | | 615 | | |
| AAT | AAA | ATG | GGA | GAA | ATA | TAT | AAC | GAA | TTT | GAA | GGA | TCA | TTA | AAT | AAA | 1776 |
| Asn | Lys | Met | Gly | Glu | Ile | Tyr | Asn | Glu | Phe | Glu | Gly | Ser | Leu | Asn | Lys | |
| | | | 620 | | | | | 625 | | | | | 630 | | | |
| ATT | AGT | GAA | AAT | TTA | AGA | AAT | GCT | TCG | GAA | AAC | ACT | TCA | GAC | TAT | AAC | 1824 |
| Ile | Ser | Glu | Asn | Leu | Arg | Asn | Ala | Ser | Glu | Asn | Thr | Ser | Asp | Tyr | Asn | |
| | | 635 | | | | | 640 | | | | | 645 | | | | |
| TCA | GCA | AAA | ACA | CTG | AGG | CTA | GAG | GCA | CAG | AAA | GAA | AAA | GTT | AAT | CTA | 1872 |
| Ser | Ala | Lys | Thr | Leu | Arg | Leu | Glu | Ala | Gln | Lys | Glu | Lys | Val | Asn | Leu | |
| | 650 | | | | 655 | | | | | 660 | | | | | | |
| TTA | AAT | AAA | GAA | GAA | GAG | GCA | AAT | AAA | TAT | TTA | AGA | GAT | GTT | AAA | AAA | 1920 |
| Leu | Asn | Lys | Glu | Glu | Glu | Ala | Asn | Lys | Tyr | Leu | Arg | Asp | Val | Lys | Lys | |
| 665 | | | | 670 | | | | | 675 | | | | | 680 | | |
| GTG | GAA | TCA | TTC | AGA | TTT | ATA | TTT | AAT | ATG | AAA | GAA | AGC | TTA | GAT | AAG | 1968 |
| Val | Glu | Ser | Phe | Arg | Phe | Ile | Phe | Asn | Met | Lys | Glu | Ser | Leu | Asp | Lys | |
| | | | | 685 | | | | | 690 | | | | | 695 | | |
| ATT | AAT | GAG | ATG | ATT | AAA | AAA | GAA | CAA | CTA | ACA | GTC | AAT | GAA | GGA | CAC | 2016 |
| Ile | Asn | Glu | Met | Ile | Lys | Lys | Glu | Gln | Leu | Thr | Val | Asn | Glu | Gly | His | |
| | | | 700 | | | | | 705 | | | | | 710 | | | |
| GGT | AAC | GTT | AAA | CAA | CTA | GTT | GAA | AAT | ATT | AAA | GAG | TTA | GTT | GAT | GAA | 2064 |
| Gly | Asn | Val | Lys | Gln | Leu | Val | Glu | Asn | Ile | Lys | Glu | Leu | Val | Asp | Glu | |
| | | 715 | | | | | 720 | | | | | 725 | | | | |
| AAC | AAC | TTA | TCA | GAT | ATA | TTA | AAA | CAA | GCG | ACG | GGC | AAA | AAT | GAG | GAA | 2112 |
| Asn | Asn | Leu | Ser | Asp | Ile | Leu | Lys | Gln | Ala | Thr | Gly | Lys | Asn | Glu | Glu | |
| | 730 | | | | | 735 | | | | | 740 | | | | | |
| ATA | CAG | AAA | ATA | ACG | CAC | TCT | ACG | CTT | AAA | AAT | AAA | GCA | AAA | ACT | ATT | 2160 |
| Ile | Gln | Lys | Ile | Thr | His | Ser | Thr | Leu | Lys | Asn | Lys | Ala | Lys | Thr | Ile | |
| 745 | | | | | 750 | | | | | 755 | | | | | 760 | |
| TTA | GGA | CAC | GTA | GAT | ACT | TCT | GCA | AAA | TAT | GTA | GGC | ATT | AAA | ATA | ACA | 2208 |
| Leu | Gly | His | Val | Asp | Thr | Ser | Ala | Lys | Tyr | Val | Gly | Ile | Lys | Ile | Thr | |
| | | | | 765 | | | | | 770 | | | | | 775 | | |
| CCT | GAG | TTG | GCA | CTA | ACA | GAA | TTG | TTA | GGA | GAT | GCA | AAA | TTG | AAA | ACT | 2256 |
| Pro | Glu | Leu | Ala | Leu | Thr | Glu | Leu | Leu | Gly | Asp | Ala | Lys | Leu | Lys | Thr | |
| | | | 780 | | | | | 785 | | | | | 790 | | | |
| GCA | CAG | GAA | TTA | AAA | TTT | GAG | TCA | AAA | AAT | AAT | GTA | GTA | CTA | GAA | ACA | 2304 |
| Ala | Gln | Glu | Leu | Lys | Phe | Glu | Ser | Lys | Asn | Asn | Val | Val | Leu | Glu | Thr | |
| | | 795 | | | | | 800 | | | | | 805 | | | | |
| GAA | AAT | ATG | TCA | AAG | AAT | ACA | AAC | GAA | TTG | GAT | GTT | CAT | AAA | AAT | ATA | 2352 |
| Glu | Asn | Met | Ser | Lys | Asn | Thr | Asn | Glu | Leu | Asp | Val | His | Lys | Asn | Ile | |
| | 810 | | | | | 815 | | | | | 820 | | | | | |
| CAG | GAT | GCT | TAC | AAG | GTT | GCA | CTG | GAA | ATA | CTT | GCC | CAC | TCA | GAC | GAA | 2400 |
| Gln | Asp | Ala | Tyr | Lys | Val | Ala | Leu | Glu | Ile | Leu | Ala | His | Ser | Asp | Glu | |
| 825 | | | | | 830 | | | | | 835 | | | | | 840 | |
| ATA | GAT | ACA | AAA | CAA | AAA | GAC | AGT | TCT | AAA | TTA | ATA | GAA | ATG | GGA | AAC | 2448 |
| Ile | Asp | Thr | Lys | Gln | Lys | Asp | Ser | Ser | Lys | Leu | Ile | Glu | Met | Gly | Asn | |
| | | | | 845 | | | | | 850 | | | | | 855 | | |
| CAA | ATA | TAT | CTT | AAA | GTT | GTG | CTA | ATA | AAT | CAA | TAC | AAA | AAT | AAA | ATA | 2496 |
| Gln | Ile | Tyr | Leu | Lys | Val | Val | Leu | Ile | Asn | Gln | Tyr | Lys | Asn | Lys | Ile | |
| | | | 860 | | | | | 865 | | | | | 870 | | | |
| AGC | TCT | ATA | AAA | AGT | AAG | GAA | GAA | GCT | GTT | TCA | GTC | AAA | ATA | GGT | AAT | 2544 |
| Ser | Ser | Ile | Lys | Ser | Lys | Glu | Glu | Ala | Val | Ser | Val | Lys | Ile | Gly | Asn | |
| | | 875 | | | | | 880 | | | | | 885 | | | | |
| GTT | TCC | AAG | AAA | CAT | AGT | GAG | TTA | AGC | AAA | ATT | ACA | TGC | AGC | GAT | AAA | 2592 |
| Val | Ser | Lys | Lys | His | Ser | Glu | Leu | Ser | Lys | Ile | Thr | Cys | Ser | Asp | Lys | |
| | 890 | | | | | 895 | | | | | 900 | | | | | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| AGT | TAC | GAT | AAC | ATC | ATA | GCG | TTA | GAG | AAA | CAA | ACT | GAA | TTA | CAA | AAT | 2640 |
| Ser | Tyr | Asp | Asn | Ile | Ile | Ala | Leu | Glu | Lys | Gln | Thr | Glu | Leu | Gln | Asn |      |
| 905 |     |     |     | 910 |     |     |     |     | 915 |     |     |     |     | 920 |     |      |
| CTA | CGC | AAT | TCT | TTC | ACT | CAA | GAA | AAG | ACT | AAC | ACG | AAT | AGC | GAT | TCG | 2688 |
| Leu | Arg | Asn | Ser | Phe | Thr | Gln | Glu | Lys | Thr | Asn | Thr | Asn | Ser | Asp | Ser |      |
|     |     |     |     | 925 |     |     |     |     | 930 |     |     |     |     | 935 |     |      |
| AAG | TTG | GAA | AAA | ATT | AAA | ACA | GAT | TTC | GAA | AGT | TTG | AAA | AAT | GCA | TTA | 2736 |
| Lys | Leu | Glu | Lys | Ile | Lys | Thr | Asp | Phe | Glu | Ser | Leu | Lys | Asn | Ala | Leu |      |
|     |     |     |     | 940 |     |     |     |     | 945 |     |     |     |     | 950 |     |      |
| AAA | ACA | CTA | GAA | GGA | GAA | GTA | AAT | GCT | CTA | AAG | GCA | AGC | TCG | GAC | AAT | 2784 |
| Lys | Thr | Leu | Glu | Gly | Glu | Val | Asn | Ala | Leu | Lys | Ala | Ser | Ser | Asp | Asn |      |
|     |     |     | 955 |     |     |     |     | 960 |     |     |     |     | 965 |     |     |      |
| CAT | GAA | CAT | GTA | CAA | AGT | AAA | AGT | GAA | CCA | GTA | AAT | CCT | GCG | CTA | TCC | 2832 |
| His | Glu | His | Val | Gln | Ser | Lys | Ser | Glu | Pro | Val | Asn | Pro | Ala | Leu | Ser |      |
|     | 970 |     |     |     |     | 975 |     |     |     |     | 980 |     |     |     |     |      |
| GAA | ATT | GAA | AAA | GAA | GAA | ACG | GAC | ATA | GAT | AGT | CTT | AAT | ACG | GCC | CTT | 2880 |
| Glu | Ile | Glu | Lys | Glu | Glu | Thr | Asp | Ile | Asp | Ser | Leu | Asn | Thr | Ala | Leu |      |
| 985 |     |     |     |     | 990 |     |     |     |     | 995 |     |     |     |     | 1000|      |
| GAT | GAG | TTA | TTA | AAA | AAA | GGA | AGG | ACA | TGC | GAA | GTA | TCT | AGG | TAC | AAA | 2928 |
| Asp | Glu | Leu | Leu | Lys | Lys | Gly | Arg | Thr | Cys | Glu | Val | Ser | Arg | Tyr | Lys |      |
|     |     |     |     | 1005|     |     |     |     | 1010|     |     |     |     | 1015|     |      |
| CTG | ATA | AAG | GAT | ACC | GTT | ACC | AAA | GAA | ATA | AGT | GAT | GAC | ACC | GAA | TTA | 2976 |
| Leu | Ile | Lys | Asp | Thr | Val | Thr | Lys | Glu | Ile | Ser | Asp | Asp | Thr | Glu | Leu |      |
|     |     |     | 1020|     |     |     |     | 1025|     |     |     |     | 1030|     |     |      |
| ATC | AAC | ACT | ATA | GAG | AAG | AAT | GTT | AAA | GCA | TAC | TTG | GCA | TAT | ATT | AAA | 3024 |
| Ile | Asn | Thr | Ile | Glu | Lys | Asn | Val | Lys | Ala | Tyr | Leu | Ala | Tyr | Ile | Lys |      |
|     |     | 1035|     |     |     |     | 1040|     |     |     |     | 1045|     |     |     |      |
| AAA | AAT | TAT | GAA | GAC | ACA | GTG | CAA | GAT | GTT | CTT | ACA | TTA | AAT | GAG | CAT | 3072 |
| Lys | Asn | Tyr | Glu | Asp | Thr | Val | Gln | Asp | Val | Leu | Thr | Leu | Asn | Glu | His |      |
|     | 1050|     |     |     |     | 1055|     |     |     |     | 1060|     |     |     |     |      |
| TTC | AAT | ACA | AAA | CAG | GTA | AGT | AAT | CAC | GAG | CCA | ACT | AAT | TTT | GAT | AAA | 3120 |
| Phe | Asn | Thr | Lys | Gln | Val | Ser | Asn | His | Glu | Pro | Thr | Asn | Phe | Asp | Lys |      |
| 1065|     |     |     |     | 1070|     |     |     |     | 1075|     |     |     |     | 1080|      |
| TCA | AAT | AAG | TCA | TCC | GAA | GAG | TTA | ACT | AAA | GCT | GTT | ACT | GAC | TCA | AAA | 3168 |
| Ser | Asn | Lys | Ser | Ser | Glu | Glu | Leu | Thr | Lys | Ala | Val | Thr | Asp | Ser | Lys |      |
|     |     |     |     | 1085|     |     |     |     | 1090|     |     |     |     | 1095|     |      |
| ACA | ATA | ATA | AGT | AAA | CTA | AAA | GGT | GTA | ATT | ATA | GAA | GTT | AAC | GAA | AAC | 3216 |
| Thr | Ile | Ile | Ser | Lys | Leu | Lys | Gly | Val | Ile | Ile | Glu | Val | Asn | Glu | Asn |      |
|     |     |     | 1100|     |     |     |     | 1105|     |     |     |     | 1110|     |     |      |
| ACT | GAA | ATG | AAC | ACT | ATA | GAA | AGC | AGT | GCA | AAA | GAA | ATT | GAA | GCT | CTC | 3264 |
| Thr | Glu | Met | Asn | Thr | Ile | Glu | Ser | Ser | Ala | Lys | Glu | Ile | Glu | Ala | Leu |      |
|     |     | 1115|     |     |     |     | 1120|     |     |     |     | 1125|     |     |     |      |
| TAT | AAC | GAA | TTA | AAA | AAT | AAA | AAA | ACA | TCA | TTA | AAC | GAA | ATT | TAT | CAA | 3312 |
| Tyr | Asn | Glu | Leu | Lys | Asn | Lys | Lys | Thr | Ser | Leu | Asn | Glu | Ile | Tyr | Gln |      |
|     | 1130|     |     |     |     | 1135|     |     |     |     | 1140|     |     |     |     |      |
| ACA | TCA | AAT | GAA | GTT | AAA | TTG | CAA | GAA | ATG | AAA | TCA | AAT | GCT | GAT | AAA | 3360 |
| Thr | Ser | Asn | Glu | Val | Lys | Leu | Gln | Glu | Met | Lys | Ser | Asn | Ala | Asp | Lys |      |
| 1145|     |     |     |     | 1150|     |     |     |     | 1155|     |     |     |     | 1160|      |
| TAC | ATC | GAT | GTA | TCT | AAA | ATA | TTT | AAC | ACT | GTA | TTA | GAC | ACT | CAA | AAG | 3408 |
| Tyr | Ile | Asp | Val | Ser | Lys | Ile | Phe | Asn | Thr | Val | Leu | Asp | Thr | Gln | Lys |      |
|     |     |     |     | 1165|     |     |     |     | 1170|     |     |     |     | 1175|     |      |
| TCA | AAT | ATA | GTA | ACT | AAT | CAA | CAT | AGC | ATA | AAC | AAT | GTT | AAA | GAC | AAA | 3456 |
| Ser | Asn | Ile | Val | Thr | Asn | Gln | His | Ser | Ile | Asn | Asn | Val | Lys | Asp | Lys |      |
|     |     |     | 1180|     |     |     |     | 1185|     |     |     |     | 1190|     |     |      |
| TTA | AAA | GGA | AAG | CTA | CAG | GAA | TTA | ATT | GAC | GCT | GAC | AGT | TCA | TTT | ACA | 3504 |
| Leu | Lys | Gly | Lys | Leu | Gln | Glu | Leu | Ile | Asp | Ala | Asp | Ser | Ser | Phe | Thr |      |
|     |     |     | 1195|     |     |     |     | 1200|     |     |     |     | 1205|     |     |      |
| TTA | GAG | TCC | ATT | AAA | AAG | TTT | AAC | GAA | ATA | TAT | AGT | CAT | ATT | AAG | ACT | 3552 |
| Leu | Glu | Ser | Ile | Lys | Lys | Phe | Asn | Glu | Ile | Tyr | Ser | His | Ile | Lys | Thr |      |
|     | 1210|     |     |     |     | 1215|     |     |     |     | 1220|     |     |     |     |      |

-continued

```
AAT ATA GGT GAA CTA GAA CAG TTA CAA CAA ACT AAT AAA AGT GAA CAT    3600
Asn Ile Gly Glu Leu Glu Gln Leu Gln Gln Thr Asn Lys Ser Glu His
1225             1230                 1235                 1240

GAT AAT GTC GCA AAG CAC AAA GAA AAA ATT GTA CAT TTA ATA AAC AGG    3648
Asp Asn Val Ala Lys His Lys Glu Lys Ile Val His Leu Ile Asn Arg
             1245                 1250                 1255

GTA GAA AGT TTG AAA GGT GAT GTG AAA AAT CAT GAT GAT GAC CAA TAT    3696
Val Glu Ser Leu Lys Gly Asp Val Lys Asn His Asp Asp Asp Gln Tyr
         1260                 1265                 1270

ATG AAA AAA TTA AAT GCT AGT CTA TTA AAT GAT AAT ATT AAA AAT ACA    3744
Met Lys Lys Leu Asn Ala Ser Leu Leu Asn Asp Asn Ile Lys Asn Thr
     1275                 1280                 1285

ACG AAT TCC TGC AGC CCG G                                          3763
Thr Asn Ser Cys Ser Pro
     1290
```

( 2 ) INFORMATION FOR SEQ ID NO:2:

( i ) SEQUENCE CHARACTERISTICS:
        ( A ) LENGTH: 1985 base pairs
        ( B ) TYPE: Nucleic acid
        ( C ) STRANDEDNESS: double
        ( D ) TOPOLOGY: linear ( i i ) MOLECULE TYPE: Genomic DNA
        ( A ) DESCRIPTION:

( i i i ) HYPOTHETICAL: No ( i v ) ANTI-SENSE: No ( v ) FRAGMENT TYPE:

( v i ) ORIGINAL SOURCE:
        ( A ) ORGANISM: P.vivax
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY: Lambda gt 11 native P.vivax
            DNA expression library
        ( B ) CLONE: 7.2

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION: This sequence corresponds to
            Figure 1B (sheets 1 and 2) in
            the application, as filed.

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:2:

| | | | | | | | | | | | | | | | | |
|---|---|---|---|---|---|---|---|---|---|---|---|---|---|---|---|---|
| CTC | AAA | ACT | AAA | ATT | GAA | AAA | TTG | ATA | CAG | GAA | ACA | AGT | GAT | GAT | TCA | 48 |
| Leu | Lys | Thr | Lys | Ile | Glu | Lys | Leu | Ile | Gln | Glu | Thr | Ser | Asp | Asp | Ser | |
| 1 | | | | 5 | | | | | 10 | | | | | 15 | | |
| CAA | AAT | GAA | TTA | GTC | ACA | ACG | AGT | ATT | ACA | AAA | CAT | TTA | GAG | AAT | GCA | 96 |
| Gln | Asn | Glu | Leu | Val | Thr | Thr | Ser | Ile | Thr | Lys | His | Leu | Glu | Asn | Ala | |
| | | | | 20 | | | | | 25 | | | | | 30 | | |
| AAG | GGG | TAT | GAG | GAT | GTA | ATA | AAA | CGA | AAT | GAA | GAA | GAT | TCA | ATT | CAG | 144 |
| Lys | Gly | Tyr | Glu | Asp | Val | Ile | Lys | Arg | Asn | Glu | Glu | Asp | Ser | Ile | Gln | |
| | | | 35 | | | | | 40 | | | | | 45 | | | |
| TTG | AGG | GAG | AAG | GCG | AAA | AGT | CTG | GAG | ACA | TTG | GAT | GAA | ATG | AAA | AAA | 192 |
| Leu | Arg | Glu | Lys | Ala | Lys | Ser | Leu | Glu | Thr | Leu | Asp | Glu | Met | Lys | Lys | |
| | 50 | | | | | 55 | | | | | 60 | | | | | |
| CTA | GTT | CAG | CAG | GTT | AAC | ATG | AAT | TTG | CAA | AGT | GCT | ATA | CAA | GGC | AAT | 240 |
| Leu | Val | Gln | Gln | Val | Asn | Met | Asn | Leu | Gln | Ser | Ala | Ile | Gln | Gly | Asn | |
| 65 | | | | | 70 | | | | | 75 | | | | | 80 | |
| GCT | GGT | ATA | AGC | AAA | GAG | CTG | AAT | GAG | CTT | AAA | GGC | GTT | ATC | GAA | TTG | 288 |
| Ala | Gly | Ile | Ser | Lys | Glu | Leu | Asn | Glu | Leu | Lys | Gly | Val | Ile | Glu | Leu | |
| | | | | 85 | | | | | 90 | | | | | 95 | | |
| TTG | ATA | TCA | ACG | AAT | TAT | AGC | AGC | ATT | TTA | GAA | TAT | GTA | AAG | AAA | AAT | 336 |
| Leu | Ile | Ser | Thr | Asn | Tyr | Ser | Ser | Ile | Leu | Glu | Tyr | Val | Lys | Lys | Asn | |
| | | | 100 | | | | | 105 | | | | | 110 | | | |
| TCC | AGC | GAG | TCT | GTC | CGT | TTT | AGT | CAG | CTA | GCC | AAT | GGG | GAA | TTT | ACA | 384 |
| Ser | Ser | Glu | Ser | Val | Arg | Phe | Ser | Gln | Leu | Ala | Asn | Gly | Glu | Phe | Thr | |
| | | 115 | | | | | 120 | | | | | 125 | | | | |
| AAG | GCT | GAA | GGT | GAA | GAG | AAA | AAC | GCA | AGT | GCC | AGA | TTA | GCG | GAG | GCA | 432 |
| Lys | Ala | Glu | Gly | Glu | Glu | Lys | Asn | Ala | Ser | Ala | Arg | Leu | Ala | Glu | Ala | |
| | 130 | | | | | 135 | | | | | 140 | | | | | |
| GAG | AAG | TTA | AAG | GAA | CAA | ATT | GTC | AAA | GAT | TTA | GAC | TAC | AGT | GAC | ATA | 480 |
| Glu | Lys | Leu | Lys | Glu | Gln | Ile | Val | Lys | Asp | Leu | Asp | Tyr | Ser | Asp | Ile | |
| 145 | | | | | 150 | | | | | 155 | | | | | 160 | |
| GAT | GAT | AAG | GTA | AAA | AAA | ATT | GAG | GGA | ATC | AAA | AGA | GAA | ATT | TTA | AAG | 528 |
| Asp | Asp | Lys | Val | Lys | Lys | Ile | Glu | Gly | Ile | Lys | Arg | Glu | Ile | Leu | Lys | |
| | | | | 165 | | | | | 170 | | | | | 175 | | |
| ATG | AAA | GAA | AGT | GCA | CTA | ACA | TTT | TGG | GAA | GAG | TCA | GAG | AAG | TTT | AAA | 576 |
| Met | Lys | Glu | Ser | Ala | Leu | Thr | Phe | Trp | Glu | Glu | Ser | Glu | Lys | Phe | Lys | |
| | | | 180 | | | | | 185 | | | | | 190 | | | |
| CAA | ATG | TGC | TCT | TCA | CAT | ATG | GAA | AAT | GCT | AAA | GAG | GGG | AAG | AAA | AAA | 624 |
| Gln | Met | Cys | Ser | Ser | His | Met | Glu | Asn | Ala | Lys | Glu | Gly | Lys | Lys | Lys | |
| | | 195 | | | | | 200 | | | | | 205 | | | | |
| ATT | GAG | TAT | TTA | AAA | AAT | AAT | GGG | GAT | GGA | GGA | AAG | GCC | AAC | ATA | ACG | 672 |
| Ile | Glu | Tyr | Leu | Lys | Asn | Asn | Gly | Asp | Gly | Gly | Lys | Ala | Asn | Ile | Thr | |
| | 210 | | | | | 215 | | | | | 220 | | | | | |
| GAT | AGC | CAA | ATG | GAG | GAG | GTA | GGT | AAC | TAT | GTT | AGC | AAA | GCT | GAG | CAC | 720 |
| Asp | Ser | Gln | Met | Glu | Glu | Val | Gly | Asn | Tyr | Val | Ser | Lys | Ala | Glu | His | |
| 225 | | | | | 230 | | | | | 235 | | | | | 240 | |
| GCC | TTT | CAC | ACA | GTA | GAA | GCA | CAG | GTA | GAC | AAA | ACT | AAA | GCC | TTT | TGC | 768 |
| Ala | Phe | His | Thr | Val | Glu | Ala | Gln | Val | Asp | Lys | Thr | Lys | Ala | Phe | Cys | |
| | | | | 245 | | | | | 250 | | | | | 255 | | |
| GAA | TCC | ATC | GTA | GCT | TAT | GTA | ACG | AAG | ATG | GAC | AAC | CTG | TTT | AAC | GAA | 816 |
| Glu | Ser | Ile | Val | Ala | Tyr | Val | Thr | Lys | Met | Asp | Asn | Leu | Phe | Asn | Glu | |
| | | | 260 | | | | | 265 | | | | | 270 | | | |
| TCG | TTA | ATG | AAA | GAA | GTG | AAA | GTG | AAG | TGT | GAA | AAA | AAG | AAT | GAT | GAA | 864 |
| Ser | Leu | Met | Lys | Glu | Val | Lys | Val | Lys | Cys | Glu | Lys | Lys | Asn | Asp | Glu | |
| | | 275 | | | | | 280 | | | | | 285 | | | | |
| GCG | GAG | AAA | TAT | TCG | GCC | AAA | TTA | AAA | CCG | TAC | GAT | GGT | AGA | ATT | AAA | 912 |
| Ala | Glu | Lys | Tyr | Ser | Ala | Lys | Leu | Lys | Pro | Tyr | Asp | Gly | Arg | Ile | Lys | |
| | 290 | | | | | 295 | | | | | 300 | | | | | |
| GCG | CGA | GTG | AGT | GAG | AAT | GAA | AGA | AAA | ATA | AGC | GAA | TTG | AAG | GAA | AAA | 960 |
| Ala | Arg | Val | Ser | Glu | Asn | Glu | Arg | Lys | Ile | Ser | Glu | Leu | Lys | Glu | Lys | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| 305 |     |     |     | 310 |     |     |     | 315 |     |     |     | 320 |     |     |     |      |
| GCC | AAA | GTT | GAG | AAA | AAG | GAA | TCC | TCG | CAA | CTT | AAC | GAT | GTT | TCC | ACG | 1008 |
| Ala | Lys | Val | Glu | Lys | Lys | Glu | Ser | Ser | Gln | Leu | Asn | Asp | Val | Ser | Thr |      |
|     |     |     |     | 325 |     |     |     | 330 |     |     |     | 335 |     |     |     |      |
| AAG | TCG | TTA | TTA | CAA | ATA | GAT | AAT | TGC | AGA | CAA | CAG | CTT | GAC | AGC | GTT | 1056 |
| Lys | Ser | Leu | Leu | Gln | Ile | Asp | Asn | Cys | Arg | Gln | Gln | Leu | Asp | Ser | Val |      |
|     |     |     | 340 |     |     |     | 345 |     |     |     | 350 |     |     |     |     |      |
| TTG | TCA | AAC | ATT | GGA | AGG | GTG | AAA | CAA | AAT | GCA | CTT | CAA | TAT | TTC | GAT | 1104 |
| Leu | Ser | Asn | Ile | Gly | Arg | Val | Lys | Gln | Asn | Ala | Leu | Gln | Tyr | Phe | Asp |      |
|     |     | 355 |     |     |     | 360 |     |     |     | 365 |     |     |     |     |     |      |
| TCG | GCT | GAT | AAA | TCG | ATG | AAG | TCC | GTT | TTG | CCT | ATA | AGC | GAA | TTG | GGT | 1152 |
| Ser | Ala | Asp | Lys | Ser | Met | Lys | Ser | Val | Leu | Pro | Ile | Ser | Glu | Leu | Gly |      |
|     | 370 |     |     |     | 375 |     |     |     | 380 |     |     |     |     |     |     |      |
| GCC | GAA | AAA | TCG | CTA | GAC | AAA | GTA | AAA | GCG | GCT | AAG | GAA | AGT | TAT | GAG | 1200 |
| Ala | Glu | Lys | Ser | Leu | Asp | Lys | Val | Lys | Ala | Ala | Lys | Glu | Ser | Tyr | Glu |      |
| 385 |     |     |     | 390 |     |     |     | 395 |     |     |     |     |     |     | 400 |      |
| AAA | AAT | TTG | GAA | ACC | GTT | CAA | AAT | GAA | ATG | AGT | CGT | ATT | AAT | GTG | GAA | 1248 |
| Lys | Asn | Leu | Glu | Thr | Val | Gln | Asn | Glu | Met | Ser | Arg | Ile | Asn | Val | Glu |      |
|     |     |     |     | 405 |     |     |     | 410 |     |     |     | 415 |     |     |     |      |
| GAA | GGA | AGT | CTG | ACC | GAC | ATA | GAC | AAA | AAA | ATA | ACT | GAC | ATA | GAA | AAT | 1296 |
| Glu | Gly | Ser | Leu | Thr | Asp | Ile | Asp | Lys | Lys | Ile | Thr | Asp | Ile | Glu | Asn |      |
|     |     |     | 420 |     |     |     | 425 |     |     |     | 430 |     |     |     |     |      |
| GAC | TTG | CTA | AAA | ATG | AAG | AAA | CAA | TAT | GAA | GAA | GGG | TTA | CTA | CAA | AAG | 1344 |
| Asp | Leu | Leu | Lys | Met | Lys | Lys | Gln | Tyr | Glu | Glu | Gly | Leu | Leu | Gln | Lys |      |
|     |     | 435 |     |     |     | 440 |     |     |     | 445 |     |     |     |     |     |      |
| ATT | AAA | GAA | AAT | GCG | GAT | AAG | AGG | AAG | AGT | AAT | TTC | GAA | TTA | GTA | GGA | 1392 |
| Ile | Lys | Glu | Asn | Ala | Asp | Lys | Arg | Lys | Ser | Asn | Phe | Glu | Leu | Val | Gly |      |
|     | 450 |     |     |     | 455 |     |     |     | 460 |     |     |     |     |     |     |      |
| AGC | GAA | ATA | AAC | GCC | TTG | CTG | GAT | CCA | AGC | ACG | TCT | ATT | TTT | ATT | AAA | 1440 |
| Ser | Glu | Ile | Asn | Ala | Leu | Leu | Asp | Pro | Ser | Thr | Ser | Ile | Phe | Ile | Lys |      |
| 465 |     |     |     | 470 |     |     |     | 475 |     |     |     |     |     |     | 480 |      |
| TTA | AAA | TTA | AAG | GAA | TAT | GAC | ATG | ACC | GGC | GAT | TTA | AAA | AAT | TAC | GGT | 1488 |
| Leu | Lys | Leu | Lys | Glu | Tyr | Asp | Met | Thr | Gly | Asp | Leu | Lys | Asn | Tyr | Gly |      |
|     |     |     |     | 485 |     |     |     | 490 |     |     |     | 495 |     |     |     |      |
| GTT | AAA | ATG | AAT | GAA | ATT | CAT | GGT | GAA | TTT | ACC | AAA | TCG | TAC | AAT | TTG | 1536 |
| Val | Lys | Met | Asn | Glu | Ile | His | Gly | Glu | Phe | Thr | Lys | Ser | Tyr | Asn | Leu |      |
|     |     |     | 500 |     |     |     | 505 |     |     |     | 510 |     |     |     |     |      |
| ATA | GAA | ACC | CAT | TTG | TCC | AAT | GCT | ACA | GAT | TAT | TCT | GTG | ACG | TTT | GAG | 1584 |
| Ile | Glu | Thr | His | Leu | Ser | Asn | Ala | Thr | Asp | Tyr | Ser | Val | Thr | Phe | Glu |      |
|     |     | 515 |     |     |     | 520 |     |     |     | 525 |     |     |     |     |     |      |
| AAG | GCC | CAA | AGT | TTA | AGG | GAA | CTA | GCA | GAG | AAG | GAA | GAA | GAA | CAT | CTC | 1632 |
| Lys | Ala | Gln | Ser | Leu | Arg | Glu | Leu | Ala | Glu | Lys | Glu | Glu | Glu | His | Leu |      |
|     | 530 |     |     |     | 535 |     |     |     | 540 |     |     |     |     |     |     |      |
| AGA | AGA | AGA | GAG | GAG | GAA | GCG | ATC | TTT | CTG | CTG | AAT | GAT | ATT | AAA | AAG | 1680 |
| Arg | Arg | Arg | Glu | Glu | Glu | Ala | Ile | Phe | Leu | Leu | Asn | Asp | Ile | Lys | Lys |      |
| 545 |     |     |     | 550 |     |     |     | 555 |     |     |     |     |     |     | 560 |      |
| GTG | GAA | TCG | TTA | AAA | CTG | CTA | AAA | GAA | ATG | ATG | AAA | AAG | GTG | AGT | GCC | 1728 |
| Val | Glu | Ser | Leu | Lys | Leu | Leu | Lys | Glu | Met | Met | Lys | Lys | Val | Ser | Ala |      |
|     |     |     |     | 565 |     |     |     | 570 |     |     |     | 575 |     |     |     |      |
| GAA | TAT | GAA | GGT | ATG | AAA | AGA | GAC | CAT | ACG | AGT | GTT | AGT | CAG | CTT | GTA | 1776 |
| Glu | Tyr | Glu | Gly | Met | Lys | Arg | Asp | His | Thr | Ser | Val | Ser | Gln | Leu | Val |      |
|     |     |     | 580 |     |     |     | 585 |     |     |     | 590 |     |     |     |     |      |
| CAG | GAT | ATG | AAG | ACA | ATT | GTT | GAT | GAG | CTG | AAA | ACA | CTG | AAT | GAT | ATA | 1824 |
| Gln | Asp | Met | Lys | Thr | Ile | Val | Asp | Glu | Leu | Lys | Thr | Leu | Asn | Asp | Ile |      |
|     |     | 595 |     |     |     | 600 |     |     |     | 605 |     |     |     |     |     |      |
| AGC | GAA | TGT | TCG | AGC | GTG | CTA | AAC | AAT | GTA | GTT | AGT | ATA | GTT | AAA | AAG | 1872 |
| Ser | Glu | Cys | Ser | Ser | Val | Leu | Asn | Asn | Val | Val | Ser | Ile | Val | Lys | Lys |      |
|     | 610 |     |     |     | 615 |     |     |     | 620 |     |     |     |     |     |     |      |
| GTT | AAA | GAG | TCG | AAA | CAT | GCA | GAC | TAT | AGG | AGA | GAC | GCG | AAT | AGC | ATG | 1920 |
| Val | Lys | Glu | Ser | Lys | His | Ala | Asp | Tyr | Arg | Arg | Asp | Ala | Asn | Ser | Met |      |

```
625                   630                        635                        640
TAT GAA AGT ATG GTA ACT CTG GCA AAT TAT TTC CTA AGC GAT GAG GCT    1968
Tyr Glu Ser Met Val Thr Leu Ala Asn Tyr Phe Leu Ser Asp Glu Ala
                645                      650                 655

AAA ATT TCA TCA GGA AT                                              1985
Lys Ile Ser Ser Gly Xaa
            660
```

( 2 ) INFORMATION FOR SEQ ID NO:3:

( i ) SEQUENCE CHARACTERISTICS:
        ( A ) LENGTH: 1769 base pairs
        ( B ) TYPE: Nucleic acid
        ( C ) STRANDEDNESS: double
        ( D ) TOPOLOGY: linear ( i i ) MOLECULE TYPE: Genomic DNA
        ( A ) DESCRIPTION:

( i i i ) HYPOTHETICAL: No ( i v ) ANTI-SENSE: No ( v ) FRAGMENT TYPE:

( v i ) ORIGINAL SOURCE:
        ( A ) ORGANISM: P.vivax
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION: This sequence corresponds to
        Figure 12 (sheets 1-4) in the
        application, as filed.

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:3:

```
TCC GTG CAA CCT TTA CTT GGA TCG AAA TCT CGA CAA GGG GAT TAC CAA     48
Ser Val Gln Pro Leu Leu Gly Ser Lys Ser Arg Gln Gly Asp Tyr Gln
 1               5                  10                  15

ACG GGT GGC GCA TTC ACA AAT GGA TAT GCA CAA ATG GAT ATG CAC ATG     96
Thr Gly Gly Ala Phe Thr Asn Gly Tyr Ala Gln Met Asp Met His Met
             20                  25                  30

GAA GAC GAC GAC GAG GAT GAT GGT GGA GGA GAG CCC AAA GAC TTA AAT    144
```

|  |  |  |  |  |  |  |  |  |  |  |  |  |  |  |  |
|---|---|---|---|---|---|---|---|---|---|---|---|---|---|---|---|
| Glu | Asp | Asp<br>35 | Asp | Glu | Asp | Asp | Gly<br>40 | Gly | Gly | Glu | Pro | Lys<br>45 | Asp | Leu | Asn |

| TTC | CCG | GGC | ATG | ATA | CGA | AAT | AAC | CCC | ATG | ATG | GAT | TTT | TTA | AAT | ACA | 192 |
|---|---|---|---|---|---|---|---|---|---|---|---|---|---|---|---|---|
| Phe | Pro<br>50 | Gly | Met | Ile | Arg | Asn<br>55 | Asn | Pro | Met | Met | Asp<br>60 | Phe | Leu | Asn | Thr | |

| CCT | ATC | ATG | AAT | GAA | AAC | GGA | GAA | CCA | ATT | ATC | ACG | AAC | AAG | TGT | TTG | 240 |
|---|---|---|---|---|---|---|---|---|---|---|---|---|---|---|---|---|
| Pro<br>65 | Ile | Met | Asn | Glu | Asn<br>70 | Gly | Glu | Pro | Ile | Ile<br>75 | Thr | Asn | Lys | Cys | Leu<br>80 | |

| AAC | GAA | ACG | AGG | AAA | GTA | GTT | CCC | CTT | CCT | AAT | GAA | TCG | TTC | TCG | AGT | 288 |
|---|---|---|---|---|---|---|---|---|---|---|---|---|---|---|---|---|
| Asn | Glu | Thr | Arg | Lys<br>85 | Val | Val | Pro | Leu | Pro<br>90 | Asn | Glu | Ser | Phe | Ser<br>95 | Ser | |

| CAT | CAG | GTC | GAC | ATG | GGA | GAG | CAC | CAC | TTA | CTT | GTG | AAG | GAC | ACG | AGC | 336 |
|---|---|---|---|---|---|---|---|---|---|---|---|---|---|---|---|---|
| His | Gln | Val | Asp<br>100 | Met | Gly | Glu | His | His<br>105 | Leu | Leu | Val | Lys | Asp<br>110 | Thr | Ser | |

| AAA | ACG | AAC | GAG | GCA | ACC | TCC | ACA | CAC | ACA | AAC | GAC | TTT | CAT | CAA | CCT | 384 |
|---|---|---|---|---|---|---|---|---|---|---|---|---|---|---|---|---|
| Lys | Thr | Asn<br>115 | Glu | Ala | Thr | Ser | Thr<br>120 | His | Thr | Asn | Asp | Phe<br>125 | His | Gln | Pro | |

| CAC | ATG | AAC | GCA | GAA | ATA | AGT | GGG | AAA | GAG | GTG | AAG | GAA | GAG | CGA | TGG | 432 |
|---|---|---|---|---|---|---|---|---|---|---|---|---|---|---|---|---|
| His | Met | Asn | Ala<br>130 | Glu | Ile | Ser | Gly | Lys<br>135 | Glu | Val | Lys | Glu | Glu<br>140 | Arg | Trp | |

| ATA | AAA | TGT | AAT | TCC | TTC | ATT | TAT | GAG | CCT | AGT | GCT | AAT | TAT | GCG | CAA | 480 |
|---|---|---|---|---|---|---|---|---|---|---|---|---|---|---|---|---|
| Ile<br>145 | Lys | Cys | Asn | Ser | Phe<br>150 | Ile | Tyr | Glu | Pro | Ser<br>155 | Ala | Asn | Tyr | Ala | Gln<br>160 | |

| AAA | AAT | ATG | AGG | GAG | GAT | CAT | CCT | TGT | GAA | GTT | CCA | AAT | GAT | CCA | TGT | 528 |
|---|---|---|---|---|---|---|---|---|---|---|---|---|---|---|---|---|
| Lys | Asn | Met | Arg | Glu<br>165 | Asp | His | Pro | Cys | Glu<br>170 | Val | Pro | Asn | Asp | Pro<br>175 | Cys | |

| AAG | AAT | GAA | GAA | AAT | TGT | CTC | CAC | GGA | AAT | GGA | GTT | CTC | CAC | CAC | TCC | 576 |
|---|---|---|---|---|---|---|---|---|---|---|---|---|---|---|---|---|
| Lys | Asn | Glu | Glu<br>180 | Asn | Cys | Leu | His | Gly<br>185 | Asn | Gly | Val | Leu | His<br>190 | His | Ser | |

| AGT | GAA | CAG | AAC | GAT | TCG | GTT | GCC | CAT | TCA | CAA | GTT | CAC | GAC | TGT | TAC | 624 |
|---|---|---|---|---|---|---|---|---|---|---|---|---|---|---|---|---|
| Ser | Glu | Gln | Asn<br>195 | Asp | Ser | Val | Ala | His<br>200 | Ser | Gln | Val | His | Asp<br>205 | Cys | Tyr | |

| AAC | TAT | AGG | TTC | ATT | AAG | AAT | TAC | GTA | GAT | GAA | ATG | ACG | AAC | AAG | CCA | 672 |
|---|---|---|---|---|---|---|---|---|---|---|---|---|---|---|---|---|
| Asn | Tyr | Arg<br>210 | Phe | Ile | Lys | Asn | Tyr<br>215 | Val | Asp | Glu | Met | Thr<br>220 | Asn | Lys | Pro | |

| AGA | AGC | AAA | AAG | AAC | GAG | GAG | GAA | CTC | ACT | TTG | GGT | GAT | AAA | TCA | TTT | 720 |
|---|---|---|---|---|---|---|---|---|---|---|---|---|---|---|---|---|
| Arg<br>225 | Ser | Lys | Lys | Asn | Glu<br>230 | Glu | Glu | Leu | Thr | Leu<br>235 | Gly | Asp | Lys | Ser | Phe<br>240 | |

| GAT | GTG | GAA | AGG | TAT | TTG | AAA | AAG | GGG | CCC | CTT | CCG | AAG | GAT | GAT | ACA | 768 |
|---|---|---|---|---|---|---|---|---|---|---|---|---|---|---|---|---|
| Asp | Val | Glu | Arg | Tyr<br>245 | Leu | Lys | Lys | Gly | Pro<br>250 | Leu | Pro | Lys | Asp | Asp<br>255 | Thr | |

| CTG | CGG | GGT | GAT | TCT | TAT | GGT | ATA | CCC | GTG | TTC | GCA | ACT | GGG | GAA | GGA | 816 |
|---|---|---|---|---|---|---|---|---|---|---|---|---|---|---|---|---|
| Leu | Arg | Gly | Asp<br>260 | Ser | Tyr | Gly | Ile | Pro<br>265 | Val | Phe | Ala | Thr | Gly<br>270 | Glu | Gly | |

| TCA | ACC | GAT | CAA | ACG | AAT | GTA | CAG | GTG | AAT | GTG | CAG | GCG | AAT | GCG | CTT | 864 |
|---|---|---|---|---|---|---|---|---|---|---|---|---|---|---|---|---|
| Ser | Thr | Asp | Gln | Thr<br>275 | Asn | Val | Gln | Val | Asn<br>280 | Val | Gln | Ala | Asn | Ala<br>285 | Leu | |

| ATG | CCT | GTG | CAG | AGT | CAT | CTA | CAG | GGA | GGA | GTA | GAA | AAC | CCA | GAG | CCT | 912 |
|---|---|---|---|---|---|---|---|---|---|---|---|---|---|---|---|---|
| Met | Pro | Val | Gln<br>290 | Ser | His | Leu | Gln | Gly<br>295 | Gly | Val | Glu | Asn | Pro<br>300 | Glu | Pro | |

| CTC | CCC | AAT | GGT | GAC | AAT | CAC | AAG | AAG | AGT | TCC | ACC | CTC | TGT | GGC | CAA | 960 |
|---|---|---|---|---|---|---|---|---|---|---|---|---|---|---|---|---|
| Leu | Pro<br>305 | Asn | Gly | Asp | Asn | His<br>310 | Lys | Lys | Ser | Ser | Thr<br>315 | Leu | Cys | Gly | Gln<br>320 | |

| TTG | AAT | AAT | TAC | GGC | AAC | GTT | AGC | AAT | GAA | GAA | TCC | GCA | AAT | GAG | GTA | 1008 |
|---|---|---|---|---|---|---|---|---|---|---|---|---|---|---|---|---|
| Leu | Asn | Asn | Tyr | Gly<br>325 | Asn | Val | Ser | Asn | Glu<br>330 | Glu | Ser | Ala | Asn | Glu<br>335 | Val | |

| TTG | AAC | AAG | GGA | GTC | GAA | AGA | TGT | ATT | GAT | AAC | TGT | AAA | TAC | GAT | TTA | 1056 |
|---|---|---|---|---|---|---|---|---|---|---|---|---|---|---|---|---|
| Leu | Asn | Lys | Gly<br>340 | Val | Glu | Arg | Cys | Ile<br>345 | Asp | Asn | Cys | Lys | Tyr<br>350 | Asp | Leu | |

| GCT | AGC | CAT | TCA | CAA | AGT | ATA | AAT | ATT | CTG | CGA | AAT | GAG | GAT | TCT | AAC | 1104 |
|---|---|---|---|---|---|---|---|---|---|---|---|---|---|---|---|---|

| | | | | | | | | | | | | | | | |
|---|---|---|---|---|---|---|---|---|---|---|---|---|---|---|---|
| Ala | Ser | His 355 | Ser | Gln | Ser | Ile 360 | Ile | Leu | Arg | Asn | Glu 365 | Asp | Ser | Asn | |
| CAA Gln | TTG Leu 370 | TCT Ser | CTA Leu | CAG Gln | ACT Thr | GAA Glu 375 | AAT Asn | GAA Glu | TCC Ser | AAG Lys | GGT Gly 380 | GAG Glu | GAA Glu | CAG Gln | AAC Asn | 1152 |
| GCA Ala 385 | GAT Asp | CAA Gln | GTC Val | TTT Phe | AAA Lys 390 | AAT Asn | ATT Ile | GCA Ala | ATG Met | AAG Lys 395 | ATA Ile | CAA Gln | AAC Asn | TAT Tyr | TTA Leu 400 | 1200 |
| AGA Arg | AAT Asn | TAC Tyr | AGA Arg | AAG Lys 405 | AAG Lys | ATG Met | ATT Ile | ATC Ile | GAG Glu 410 | GAG Glu | GGA Gly | AAG Lys | CAT His | CTT Leu 415 | AAT Asn | 1248 |
| GTT Val | GGT Gly | CCG Pro | ATT Ile 420 | CAT His | GGC Gly | GTA Val | GCA Ala | AGG Arg 425 | GAG Glu | TGT Cys | CCA Pro | CCA Pro | TCG Ser 430 | CAC His | GCT Ala | 1296 |
| ATG Met | GCT Ala | ACC Thr 435 | ACC Thr | AGT Ser | GCG Ala | GGT Gly | AAT Asn 440 | TAC Tyr | ATG Met | TCA Ser | ACT Thr | TGT Cys 445 | CTT Leu | GGC Gly | TCC Ser | 1344 |
| CCC Pro | CTC Leu 450 | AGC Ser | AAC Asn | CAT His | ATG Met | CAC His 455 | GTG Val | TAC Tyr | CCC Pro | GAC Asp | CAT His 460 | ATG Met | AAC Asn | AAC Asn | TCC Ser | 1392 |
| TTC Phe 465 | GCT Ala | ACT Thr | TGT Cys | TCT Ser | TTG Leu 470 | AAG Lys | GAA Glu | AAC Asn | GCA Ala | AAC Asn 474 | CTC Leu | AAG Lys | GGG Gly | AGT Ser | ATC Ile 480 | 1440 |
| AAA Lys | ATA Ile | ACT Thr | GTC Val | CCG Pro 485 | CTA Leu | TTT Phe | CTC Leu | CTG Leu | TAC Tyr 490 | ATA Ile | ACC Thr | AAT Asn | GCC Ala | TAT Tyr 495 | GCC Ala | 1488 |
| ACT Thr | GTT Val | GAT Asp | GTC Val 500 | AGT Ser | GGA Gly | AGC Ser | AAC Asn | ACC Thr 505 | AAG Lys | AGT Ser | GCG Ala | CAT His | GCG Ala 510 | ATG Met | CGT Arg | 1536 |
| TGG Trp | AAA Lys | AAG Lys 515 | CTG Leu | AAA Lys | AAA Lys | AAA Lys | ATT Ile 520 | ATG Met | AAC Asn | GAA Glu | ATA Ile | ATT Ile 525 | TTT Phe | GGA Gly | TTT Phe | 1584 |
| ACC Thr | TAT Tyr 530 | GCA Ala | GAT Asp | GCG Ala | GAT Asp | AAA Lys 535 | TAC Tyr | GTA Val | GAG Glu | CAA Gln | CTT Leu 540 | CTA Leu | TGT Cys | AAT Asn | ATT Ile | 1632 |
| AAA Lys 545 | AAG Lys | TGC Cys | TTC Phe | ATT Ile | CAA Gln 550 | GTA Val | TTG Leu | GAT Asp | TAC Tyr | TTG Leu 555 | AAG Lys | GAA Glu | TAT Tyr | AAC Asn | CCT Pro 560 | 1680 |
| CAA Gln | TGG Trp | GTC Val | TGT Cys | AGC Ser 565 | AAG Lys | CCT Pro | GGG Gly | GAT Asp | GCA Ala 570 | TAC Tyr | TTT Phe | TAT Tyr | CAT His | TTT Phe 575 | CGG Arg | 1728 |
| AAA Lys | ATT Ile | ATG Met | GCA Ala 580 | ATC Ile | AAC Asn | AGC Ser | TCC Ser | TAC Tyr 585 | GTG Val | GAT Asp | GTG Val | AAT Asn | TC Ser | | | 1769 |

What is claimed is:

1. A purified, isolated antigen immunochemically reactive with antibodies raised against native merozoite apical end protein (MAEP), wherein said antigen comprises an amino acid sequence encoded by a nucleic acid sequence selected from the group consisting of SEQ I.D. No. 1 and SEQ I.D. No. 2.

2. A purified, isolated protein comprising the amino acid sequence encoded by the nucleic acid sequence SEQ I.D. No. 1.

3. A purified, isolated protein comprising the amino acid sequence encoded by the nucleic acid sequence SEQ I.D. No. 2.

4. A purified, isolated antigen according to claim 1 immunochemically reactive with antibodies raised against native merozoite apical end protein of *P. vivax* origin.

* * * * *